(12) United States Patent
Cass et al.

(10) Patent No.: US 9,079,893 B2
(45) Date of Patent: Jul. 14, 2015

(54) UREIDO-PYRAZOLE DERIVATIVES FOR USE IN THE TREATMENT OF RESPIRATORY SYNCITIAL VIRUS (RSV) INFECTION

(75) Inventors: Lindsey Cass, London (GB); Kazuhiro Ito, London (GB); William Garth Rapeport, London (GB); Peter Strong, London (GB)

(73) Assignee: Respivert, Ltd., Buckinghamshire (GB)

( * ) Notice: Subject to any disclaimer, the term of this patent is extended or adjusted under 35 U.S.C. 154(b) by 25 days.

(21) Appl. No.: 13/805,552

(22) PCT Filed: Jun. 17, 2011

(86) PCT No.: PCT/GB2011/051136
§ 371 (c)(1),
(2), (4) Date: Dec. 19, 2012

(87) PCT Pub. No.: WO2011/158039
PCT Pub. Date: Dec. 22, 2011

(65) Prior Publication Data
US 2013/0102607 A1    Apr. 25, 2013

(30) Foreign Application Priority Data

Jun. 17, 2010  (GB) .................................. 1010193.9
Dec. 10, 2010  (WO) ................ PCT/GB2010/052066

(51) Int. Cl.
| | |
|---|---|
| *C07D 401/02* | (2006.01) |
| *C07D 413/14* | (2006.01) |
| *A61K 31/415* | (2006.01) |
| *A61K 31/4439* | (2006.01) |
| *A61K 31/496* | (2006.01) |
| *A61K 31/5377* | (2006.01) |
| *C07D 401/12* | (2006.01) |
| *C07D 401/14* | (2006.01) |
| *C07D 403/12* | (2006.01) |
| *C07D 405/14* | (2006.01) |

(52) U.S. Cl.
CPC ............ *C07D 413/14* (2013.01); *A61K 31/415* (2013.01); *A61K 31/4439* (2013.01); *A61K 31/496* (2013.01); *A61K 31/5377* (2013.01); *C07D 401/12* (2013.01); *C07D 401/14* (2013.01); *C07D 403/12* (2013.01); *C07D 405/14* (2013.01)

(58) Field of Classification Search
None
See application file for complete search history.

(56) References Cited

U.S. PATENT DOCUMENTS

| | | | | |
|---|---|---|---|---|
| 8,293,748 B2 * | 10/2012 | Ito et al. | ..................... | 514/253.09 |
| 8,293,771 B2 * | 10/2012 | Ito et al. | ..................... | 514/340 |
| 8,299,073 B2 * | 10/2012 | Ito et al. | ..................... | 514/236.5 |
| 8,299,074 B2 * | 10/2012 | Ito et al. | ..................... | 514/236.5 |
| 8,618,140 B2 * | 12/2013 | Ito et al. | ..................... | 514/341 |
| 8,642,773 B2 * | 2/2014 | Ito et al. | ..................... | 546/268.4 |
| 2011/0212962 A1 | 9/2011 | Ito et al. | | |
| 2011/0269800 A1 | 11/2011 | Ito et al. | | |
| 2011/0294812 A1 | 12/2011 | Ito et al. | | |
| 2011/0312963 A1 | 12/2011 | Ito et al. | | |
| 2012/0136031 A1 | 5/2012 | Ito et al. | | |
| 2012/0244120 A1 | 9/2012 | Charron et al. | | |

FOREIGN PATENT DOCUMENTS

| | | |
|---|---|---|
| EP | 1 609 789 A1 | 12/2005 |
| WO | WO 01/19322 A2 | 3/2001 |
| WO | WO 2010/038085 A2 | 4/2010 |
| WO | WO 2010/038086 A2 | 4/2010 |
| WO | WO 2010/067130 A1 | 6/2010 |
| WO | WO 2010/067131 A1 | 6/2010 |
| WO | WO 2010/112936 A1 | 10/2010 |
| WO | WO 2011/070368 A1 | 6/2011 |
| WO | WO 2011/121366 | 10/2011 |
| WO | WO 2011/124923 | 10/2011 |
| WO | WO 2011/124930 | 10/2011 |
| WO | WO 2011/158042 A2 | 12/2011 |
| WO | WO 2011/158044 A2 | 12/2011 |

OTHER PUBLICATIONS

International Search Report, PCT/GB2011/051136, Dated Aug. 3, 2011.
Bont L., "Nosocomial RSV infection control and outbreak management", Paediatric Respiratory Review, 2009, 10, Suppl 1:16-17.
Collins P.L., and Graham B.S., "Vial and Host Factors in Human Respiratory Syncytial Virus Pathogenesis", Journal of Virology, 2008, 82:2040-2055.
Bitko V., Musiyenko A. And Barik S., "Viral Infection of the Lungs through the Eye", Journal of Virology, 2007, 81:783-790.
Bauer G., Bossie L. et al., "Impacto de un programa de prevencion de infecciones respiratorias en lactanted prematuros de alto risgo: studio prospective y multicentrico", Arch. Argent. Pediatr., 2009, 107:111-118.
Mailaparambil B., Grychtol R. et al., "Respiratory Syncytial Virus Bronchiolitis and Asthma—Insights from Recent Studies and Implications for Therapy" Inflammation & Allergy Drug Targets, 2009, 8: 202-207.
Caram L. B., Chen J. et al., "Respiratory Syncytial Virus Outbreak in a Long-Term Facility Detected Using Reverse Transcriptase Polymerase Chain Reaction: An Argument for Real-Time Detection Methods", The American Geriatric Society, 2009, 57:482-485.
Wilkinson T. M., "Respivatory Syncytial Virus, Airway Inflammation, and $FEV_1$, Decline in Patients with Chronic Obstructive Pulmonary Disease" Donaldson G. C. et al., Am. J. Respir. Crit. Care, 2006, 173:871-876.
Hansbro N. G., Horvat J. C. et al., "Understanding the mechanisms of viral induced asthma: New therapeutic directions", Pharmacology and Therapeutics, 2008, 117:313-353.

(Continued)

*Primary Examiner* — Kamal Saeed
(74) *Attorney, Agent, or Firm* — Brian C. Carey

(57) ABSTRACT

Medicinal use The disclosure relates to compounds of formula (I) for use in the treatment or prophylaxis of respiratory syncitial virus (RSV) infection in particular viral exacerbation of a respiratory disorder such as bronchitis, asthma, COPD and/or cystic fibrosis, methods of treating or preventing RSV infection employing said compounds or pharmaceutical composition comprising the same.

1 Claim, 1 Drawing Sheet

(56) References Cited

OTHER PUBLICATIONS

Estripeaut D., Torres J. P. et al., "Respiratory Syncytial Virus Persistence in the Lungs Correlates with Airway Hyperreactivity in the Mouse Model", Journal of Infectious Disease, 2008, 198:1435-1443.

Spann K. M., et al., "Effects of Nonstructural Proteins NS1 and NS2 of Human Respiratory Syncytial Virus on Interferon Regulatory Factor 3, NF-$_K$B, and Proinflammatory Cytokines", Journal of Virology 2005, 79:5353-5362.

Oshansky C. M. et al., "Respiratory Syncytial Virus Proteins Modulate Suppressors of Cytokine Signaling 1 and 3 and the Type I Interferon Response to Infection by a Toll-Like Receptor Pathway", Viral Immunol., 2009, 2:147-161.

Swedan S. et al., "Respiratory syncytial Virus Nonstructural Proteins Decrease Levels of Multiple Members of the Cellular Interferon Pathways", Journal of Virology, 2009, 83:9682-9693.

Kong et al., "Respiratory syncytial virus infection activates STAT signaling in human epithelial cells" BBRC 2003, 306:616-622.

Jamaluddin M. et al., ."Respiratory Syncytial Virus-Infection Induces a Reactive Oxygen SpeciesMSK1—Phospho—Ser—276 RelA Pathway Required for Cytokine Expression", Journal of Virology, 2009, 83:10605-10615.

Mochizuki H. et al., "RS Virus-Induced Inflammation and the Intracellular Glutathione Redoz State in Cultured Human Airway Epithelial Cells", Inflammation, 2009, 32:252-264.

Kong X., et al., "ERL—1/2 activity is required for efficient RSV infection", Febs Lett., 2004, 559:33-38.

Signh D., et al., "Mapk and heat shock protein 27 activation are associated with respiratory syncytial virus induction of human bronchial epithelial monolayer disruption", Am. J. Physiol. Lung Cell. Mol. Physiol., 2007 293(2):L436-45.

Ennaciri J. et al., "Interaction of monocytic cells with respiratory syncytial virus results in an activation of NF-$_K$B and PKC—$\alpha/\beta$ leading to up-regulation of IL-15 gene expression", Journal of Leukocyte Biology, 2007, 81:625-631.

Thomas K.W. et al., "Respiratory Syncytial Virus Inhibits Apoptosis and Induces NF-$_K$B Activity through a Phosphatidylinositol 3—Kinase—dependent Pathway", Journal of Biological Chemistry, 2002, 277:492-501.

* cited by examiner

UREIDO-PYRAZOLE DERIVATIVES FOR USE IN THE TREATMENT OF RESPIRATORY SYNCITIAL VIRUS (RSV) INFECTION

This application is a National Stage application under 35 U.S.C. 371 of PCT International Application No. PCT/GB2011/051136, filed Jun. 17, 2011, which claims priority from Patent Application Nos. GB 1010193.9, filed Jun. 17, 2010 and PCT/GB2010/052066 filed Dec. 10, 2010, the contents of which are hereby incorporated by reference in their entirety.

The disclosure relates to compounds of formula (I) for use in the treatment or prophylaxis of respiratory syncitial virus (RSV) infection in particular viral exacerbation of respiratory disorders such as bronchitis, asthma, COPD and/or cystic fibrosis and to methods of treating or preventing RSV infection employing said compounds or pharmaceutical compositions comprising the same.

BACKGROUND

RSV infection is known to be transmitted through direct contact with an infection source but not through inhalation (Bont L., *Paediatr. Respir. Rev.*, 2009, 10, Suppl 1:16-17). Consistent with this mechanism, the inoculation of RSV to the human nose or eyes has been reported to result in viral replication, during an incubation period of 4 to 5 days, which may then spread infection to the lower respiratory tract (Collins P. L., and Graham B. S., *J. Virol.*, 2008, 82:2040-2055). In BALB/c mice instillation of RSV into the eye leads to an eye infection, followed by inflammation and subsequently to eye-to-lung viral transmission, resulting in respiratory pathology (Bitko V., Musiyenko A. and Bark S. *J. Virol.*, 2007, 81:783-790).

Infection by RSV is a well known cause of respiratory disease in both infants and young children and has the potential to cause severe lung disease, including bronchiolitis and death. RSV infection has been cited as a central concern in the care of high-risk, pre-term infants (Bauer G., Bossie L. et al., *Arch. Argent. Pediatr.*, 2009, 107:111-118). It remains unclear and controversial whether severe RSV infection in early infancy precipitates the development of asthma in later life or whether RSV bronchiolitis precedes asthma in children who are susceptible to becoming asthmatic (Mailaparambil B., Grychtol R. et al., *Inflamm. Allergy Drug Targets*, 2009, 8: 202-207). Recently the standard of care for treating RSV disease has been re-defined by the licensing and introduction of a monoclonal antibody therapeutic, palivizumab, a humanized mAb against the RSV F protein, which provides passive immunity against the virus.

Much more uncertainty exists regarding the prevalence and significance of RSV infections in the elderly. This arises, not least, because of the difficulty of differentiating infection by RSV from infection by influenza and the fact that both diseases show a similar prevalence by season. However, the recent development of new methods for detecting viruses has allowed research workers to investigate whether RSV infection is present in adults. This work has led to the conclusion that a significant proportion of upper respiratory tract infections (URTI) in adults is caused specifically by RSV (Caram L. B., Chen J. et al., *J. Am. Geriatr. Soc.*, 2009, 57:482-485). Furthermore, in patients diagnosed with COPD, persistent RSV detection was associated with airway inflammation and accelerated decline in FEV(1) (Wilkinson T. M., Donaldson G. C. et al., *Am. J. Respir. Crit. Care*, 2006, 173:871-876). In addition RSV infection is also commonly regarded as being a significant cause of exacerbations in patients who suffer from asthma (Hansbro N. G., Horvat J. C. et al., *Pharmacol. Ther.*, 2008, 117:313-353). Consistent with these clinical observations, RSV infection has been reported to produce airways hyper-responsiveness in mice and the persistence of RSV RNA correlated significantly with pulmonary function abnormalities (Estripeaut D., Torres J. P. et al., *J. Infect. Dis.*, 2008, 198:1435-1443).

In addition to the established view that RSV is a significant cause of morbidity and mortality in young children, recently work suggests that it is also an important factor contributing to unwanted effects in patients suffering from chronic respiratory diseases. While the introduction of palivizumab has established a new standard of care, such therapy, using monoclonal antibodies, remains very expensive and effective new medicines to treat RSV-induced lung disease are still urgently required. Furthermore, given the mode of transmission of the pathogen, there is a significant opportunity to develop therapies that prevent and/or treat viral infection by targeting those mucosal surfaces which it attacks.

RSV exploits a variety of mechanisms to suppress innate cellular immunity responses and to maintain optimal growth in the infected host cells, represented by the suppression of type I interferon (IFN) and of interferon α and interferon β induction (Spann K. M., et al., *J. Virol.* 2005, 79:5353-5362). In this regard, RSV viral surface proteins have been implicated in the reduction of Type 1 interferon expression by signalling through the Toll-like receptor pathway (Oshansky C. M. et al., *Viral Immunol.*, 2009, 2:147-161). In addition, RSV infection has been reported to decrease the cellular levels of key members of the interferon signalling pathway, including IKKε and TRAF3 (Sweden S. et al., *J. Virol.*, 2009, 83:9682-9693).

Infection by RSV has been documented to up-regulate the expression of IL-1β, IL-6, IL-8, TNF-α, MIP1a, RANTES, and ICAM-1 in epithelial cells: the main targets of RSV in vivo. The elevated expression of these inflammatory molecules during RSV infection has been attributed to the activation of nuclear factor-κ B (Kong et al., *BBRC* 2003, 306: 616-622). In this regard, RSV infection is believed to induce a time-dependent RelA phosphorylation during which reactive oxygen species are produced in parallel (Jamaluddin M. et al., *J. Virol.*, 2009, 83:10605-10615) that are potent oxidative stressors of the intracellular glutathione redox state. In human airway epithelial cells this activates signals that increase the production of cytokines and chemokines (Mochizuki H. et al., *Inflammation*, 2009, 32:252-264). In A549 cells RSV has been reported to activate both ERK-1 and ERK-2 pathways within 5 min of infection, leading to the inhibition of pathways that decrease RSV infection (Kong X., et al., *FEBS Lett.*, 2004, 559:33-38). P38MAPK activation by RSV was also confirmed in primary bronchial epithelial cells (Signh D., et al., *Am. J. Physiol. Lung Cell. Mol. Physiol.*, 2007 293(2):L436-45.). Furthermore, RSV infection has been reported to increase the phosphorylation of PKC α/β in monocytic cells (Ennaciri J. et al., *J. Leukoc. Biol.*, 2007, 81:625-631) and is associated with the induction of anti-apoptotic effects through a PI3 kinase-dependent mechanism (Thomas K. W. et al., *J. Biol. Chem.*, 2002, 277:492-501).

BRIEF DESCRIPTION OF THE INVENTION

According to the invention, there is provided a compound of formula (I):

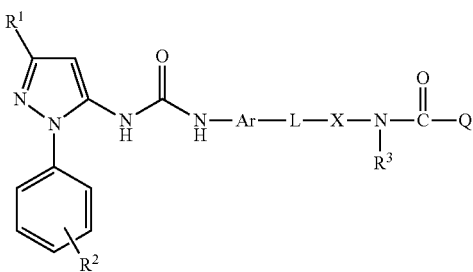

(I)

wherein $R^1$ is $C_{1-6}$ alkyl optionally substituted by a hydroxyl group;
$R^2$ is H or $C_{1-6}$ alkyl optionally substituted by a hydroxyl group;
$R^3$ is H, $C_{1-6}$ alkyl or $C_{0-3}$ alkyl$C_{3-6}$ cycloalkyl;
Ar is a naphthyl or a phenyl ring either of which may be optionally substituted by one or more groups (for example 1 to 3, such as 1, 2 or 3 groups) independently selected from $C_{1-6}$ alkyl, $C_{1-6}$ alkoxy, amino, $C_{1-4}$ mono or di-alkyl amino;
L is a saturated or unsaturated branched or unbranched $C_{1-8}$ alkylene chain, wherein one or more carbons (for example 1 to 3, such as 1, 2 or 3 carbons) are optionally replaced by —O— and the chain is optionally substituted by one or more halogen atoms (for example 1 to 6);
X is 5 or 6 membered heteroaryl group containing at least one nitrogen atom and optionally including 1 or 2 further heteroatoms selected from O, S and N;
Q is selected from:
a) a saturated or unsaturated, branched or unbranched $C_{1-10}$ alkyl chain, wherein at least one carbon (for example 1, 2 or 3 carbons, suitably 1 or 2, in particular 1 carbon) is replaced by a heteroatom selected from O, N, S(O)$_p$, wherein said chain is optionally, substituted by one or more groups (for example 1, 2 or 3 groups) independently selected from oxo, halogen, an aryl group, a heteroaryl group, a heterocyclyl group or a $C_{3-8}$ cycloalkyl group,
   each aryl, heteroaryl, heterocyclyl or $C_{3-8}$ cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)$C_{1-6}$ alkyl or $C_{0-6}$ alkylC(O)$C_{1-6}$ heteroalkyl,
   with the proviso that the atom linked directly to the carbonyl in —NR$^3$C(O)— is not an oxygen or a sulfur atom; and
b) a $C_{0-8}$ alkyl-heterocycle said heterocyclyl group comprising at least one heteroatom (for example 1, 2 or 3, suitably 1 or 2, in particular 1 heteroatom) selected from O, N, and S, and which is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, $S(O)_q C_{1-6}$ alkyl, $C_{0-6}$ alkylC(O)$C_{1-6}$ alkyl, $C_{0-6}$ alkylC(O)N$C_{0-6}$ alkyl $C_{0-6}$ alkyl or $C_{0-6}$ alkylC(O)$C_{0-6}$ heteroalkyl; and
p is 0, 1 or 2;
q is 0, 1 or 2; or
a pharmaceutically acceptable salt thereof, including all stereoisomers, tautomers and isotopic derivatives thereof for use in the treatment or prophylaxis of RSV infection and/or exacerbation of a respiratory disorder for example a chronic respiratory disorder such as asthma or COPD by RSV infection.

DETAILED DESCRIPTION OF THE INVENTION

Figure 1:
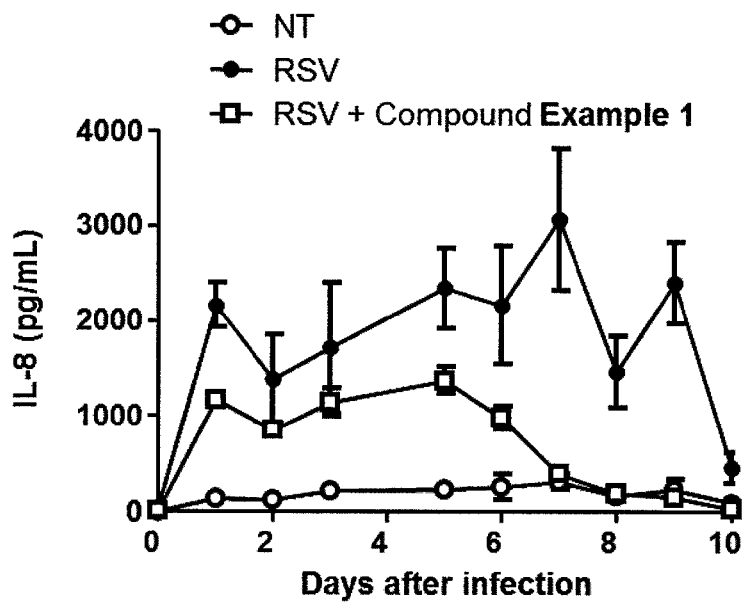
FIG. 1 shows the effects of compound Example 1 on RSV Memphis 37 induced IL-8 release in primary 3D cultured nasal epithelial cells.

In one embodiment Q is selected from:
a) a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, S(O)$_p$, wherein said chain is optionally, substituted by one or more groups independently selected from oxo, halogen, an aryl group, a heteroaryl group or a heterocyclyl group,
   each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino,
   with the proviso that the atom linked directly to the carbonyl in —NR$^3$C(O)— is not an oxygen or a sulfur atom; and
b) a $C_{0-8}$ alkyl$C_{5-6}$ heterocycle said heterocyclyl group comprising at least one heteroatom (for example 1, 2 or 3, suitably 1 or 2, in particular 1 heteroatom) selected from O, N and S, and is optionally substituted by one, two or three groups independently selected from halogen, $C_{1-6}$ alkyl, $C_{1-6}$ alkoxy, $C_{1-6}$ haloalkyl, amino, $C_{1-4}$ mono and di-alkyl amino $C_{1-4}$ mono or di-acyl amino.

For example, Q is selected from:
a) a saturated or unsaturated, branched or unbranched $C_{1-10}$ alkyl chain, wherein at least one carbon (for example 1, 2 or 3 carbons,) is replaced by a heteroatom selected from O, N, S(O)$_p$, wherein said chain is optionally, substituted by one or more groups independently selected from oxo, halogen, an aryl group, a heteroaryl group or a heterocyclyl group,
   each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, and $C_{1-4}$ mono or di-alkyl amino,
   with the proviso that the atom linked directly to the carbonyl in —NR$^3$C(O)— is not an oxygen or a sulfur atom; and
b) a $C_{0-8}$ alkyl$C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from halogen, $C_{1-6}$ alkyl, $C_{1-6}$ alkoxy, $C_{1-6}$ haloalkyl, amino, and $C_{1-4}$ mono or di-alkyl amino.

In further embodiment there is provided a compound of formula (IA):

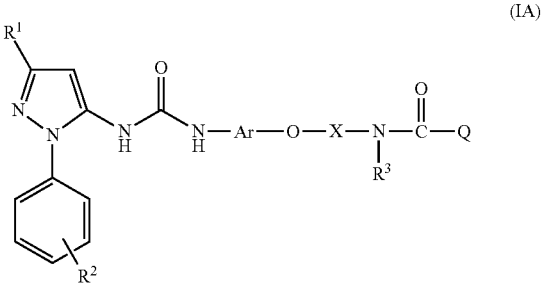

(IA)

wherein $R^1$ is $C_{1-6}$ alkyl optionally substituted by a hydroxyl group;

$R^2$ is H or $C_{1-6}$ alkyl optionally substituted by a hydroxyl group;

$R^3$ is H, $C_{1-6}$ alkyl or $C_{0-3}$ alkyl$C_{3-6}$ cycloalkyl;

Ar is a naphthyl or a phenyl ring either of which may be optionally substituted by one or more (for example 1 or 2) groups independently selected from $C_{1-6}$ alkyl, $C_{1-6}$ alkoxy, amino, $C_{1-4}$ mono or di-alkyl amino;

X is 5 or 6 membered heteroaryl group containing at least one nitrogen atom and optionally including 1 or 2 further heteroatoms selected from O, S and N;

Q is selected from:

a) a saturated or unsaturated, branched or unbranched $C_{1-10}$ alkyl chain, wherein at least one carbon (for example 1, 2 or 3 carbons, suitably 1 or 2, in particular 1 carbon) is replaced by a heteroatom selected from O, N, $S(O)_p$, wherein said chain is optionally, substituted by one or more groups (for example 1, 2 or 3 groups) independently selected from oxo, halogen, an aryl group, a heteroaryl group, a heterocyclyl group or a $C_{3-8}$ cycloalkyl group, each aryl, heteroaryl, heterocyclyl or $C_{3-8}$ cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkyl$C(O)C_{1-6}$ alkyl or $C_{0-6}$ alkyl$C(O)C_{1-6}$ heteroalkyl, with the proviso that the atom linked directly to the carbonyl in —$NR^3C(O)$— is not an oxygen or a sulfur atom; and b) a $C_{0-8}$ alkyl-heterocycle said heterocyclyl group comprising at least one heteroatom (for example 1, 2 or 3, suitably 1 or 2, in particular 1 heteroatom) selected from O, N, and S, and is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, $S(O)_q C_{1-6}$ alkyl, $C_{0-6}$ alkyl$C(O)C_{1-6}$ alkyl or $C_{0-6}$ alkyl$C(O)C_{1-6}$ heteroalkyl; and p is 0, 1 or 2;

q is 0, 1 or 2 a pharmaceutically acceptable salt thereof, including all stereoisomers, tautomers and isotopic derivatives thereof for use in the treatment or prophylaxis of RSV infection and/or exacerbation of a respiratory disorder for example a chronic respiratory disorder such as asthma or COPD by RSV infection.

In one embodiment Q is:

a) a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups (for example 1, 2 or 3) independently selected from oxo, halogen, an aryl group, a heteroaryl group, a heterocyclyl group or a $C_{3-8}$ cycloalkyl, at least one of said aryl, heteroaryl or heterocyclyl groups (such as each group) bears a substituents $C_{1-4}$ mono or di-acyl amino and optionally 1 or 2 further substituents independently selected from the relevant list of substituents above for compounds of formula (I); or b) a $C_{0-8}$ alkyl$C_{5-6}$ heterocycle said heterocyclyl group comprising at least one heteroatom (for example 1, 2 or 3, suitably 1 or 2, in particular 1 heteroatom) selected from O, N, and S, substituted by a $C_{1-4}$ mono or di-acyl amino and optionally 1 or 2 further substituents independently selected from the relevant list of substituents above for compounds of formula (I).

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$C_{1-3}$ alkyl$OC_{1-3}$ alkyl, such as —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example —$C_0$ alkyl$OC_{1-6}$ alkyl. In one embodiment the disclosure relates to straight chain alkoxy.

Heteroalkyl as employed herein is intended to refer to a branched or straight chain alkyl wherein one or more, such as 1, 2 or 3 carbons are replaced by a heteroatom, selected from N, O or $S(O)_q$, wherein q represents 0, 1 or 2. The heteroatom may replace a primary, secondary or tertiary carbon, that is, for example, SH, OH or $NH_2$ for $CH_3$, or NH or O or $SO_2$ for —$CH_2$— or N for a —CH— or a branched carbon group, as technically appropriate.

Haloalkyl as employed herein refers to alkyl groups having 1 to 6 halogen atoms, for example 1 to 5 halogens, such as per haloalkyl, in particular perfluoroalkyl, more specifically —$CF_2CF_3$ or $CF_3$.

$C_{1-4}$ mono or di-acyl amino is intended to refer to —$NHC(O)C_{1-3}$ alkyl and to (—$NC(O)C_{1-3}$ alkyl) $C(O)C_{1-3}$ alkyl) respectively.

$C_{1-4}$ mono or di-alkyl amino is intended to refer to —$NHC_{1-4}$ alkyl and —$N(C_{1-4}$ alkyl)($C_{1-4}$ alkyl) respectively.

Aryl as used herein refers to, for example $C_{6-14}$ mono or polycyclic groups having from 1 to 3 rings wherein at least one ring is aromatic including phenyl, naphthyl, anthracenyl, 1,2,3,4-tetrahydronaphthyl and the like, such as phenyl and naphthyl.

Heteroaryl is a 6 to 10 membered aromatic monocyclic ring or bicyclic ring system wherein at least one ring is an aromatic nucleus comprising one or more, for example 1, 2, 3 or 4 heteroatoms independently selected from O, N and S. Examples of heteroaryls include: pyrrole, oxazole, thiazole, isothiazole, imidazole, pyrazole, isoxazole, pyridine, pyridazine, pyrimidine, pyrazine, benzothiophene, benzofuran, or 1, 2, 3 and 1, 2, 4 triazole.

Heterocyclyl as employed herein refers to a 5 to 6 membered saturated or partially unsaturated non-aromatic ring comprising one or more, for example 1, 2, 3 or 4 heteroatoms independently selected from O, N and S optionally one or two carbons in the ring may bear an oxo substitutent. The definition of $C_{5-6}$ heterocycle as employed herein refers to a is a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substitutent. Clearly any valancies of a heteroatom not employed in forming or retaining the ring structure may be filled by hydrogen or a substituent, as appropriate. Thus substituents on heterocycles may be on carbon or on a heteroatom, such as N as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

Halogen includes fluoro, chloro, bromo or iodo, in particular fluoro, chloro or bromo, especially fluoro or chloro.

Oxo as used herein refers to C=O and will usually be represented as C(O).

$C_{3-8}$ cycloalkyl as employed herein is intended to refer to a saturated or partially unsaturated non-aromatic ring containing 3 to 8 carbon atoms.

$C_{1-10}$ alkyl includes $C_2$, $C_3$, $C_4$, $C_5$, $C_6$, $C_7$, $C_8$ or $C_9$ as well as $C_1$ and $C_{10}$.

$C_{0-8}$ alkyl includes $C_1$, $C_2$, $C_3$, $C_4$, $C_5$, $C_6$, or $C_7$ as well as $C_0$ and $C_8$.

In relation to a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo, halogen, an aryl group, a heteroaryl group or a heterocyclyl group, it will be clear to persons skilled in the art that the heteroatom may replace a primary, secondary or tertiary carbon, that is $CH_3$, $—CH_2—$ or a $—CH—$ or a branched carbon group, as technically appropriate.

In one embodiment of the disclosure there is provided compounds of formula (I), wherein $R^1$ is methyl, ethyl, propyl, iso-propyl, butyl or tert-butyl, in particular tert-butyl.

In one embodiment $R^1$ is $—C(CH_3)_2CH_2OH$.

In one embodiment $R^2$ is methyl, ethyl, n-propyl, iso-propyl, n-butyl or tert-butyl, in particular methyl.

In one embodiment $R^2$ is $—CH_2OH$.

In one embodiment $R^2$ is in the 2, 3, or 4 position (i.e. ortho, meta or para position), in particular the para (4) position.

In one embodiment Ar is naphthyl.

In one embodiment Ar is not substituted with optional substituents.

In one embodiment Ar is substituted with 1 or 2 groups.

In one embodiment Ar is phenyl optionally substituted by 1 or 2 substituents independently selected from $C_{1-3}$ alkyl or $C_{1-3}$ alkoxy, for example tolyl, xylyl, anisoyl, di-methoxybenzene or methoxy-methylbenzene. The phenyl ring may, for example, be linked to the nitrogen of the urea through carbon 1 and to the group L through carbon 4. In such a case the optional one or two substituents selected from $C_{1-3}$ alkyl or $C_{1-3}$ alkoxy may be located in any of the unoccupied positions in the aromatic ring, for example in position 2 or in position 3 or in positions 2 and 3 or in positions 2 and 6 or in positions 3 and 5. Embodiments encompassing other possible regioisomers also form an aspect of the present disclosure.

In one embodiment L is a straight chain linker, for example:
—$(CH_2)_n$— wherein n is 1, 2, 3, 4, 5, 6, 7 or 8; or
—$(CH_2)_n$—O—$(CH_2)_m$— wherein n and m are independently 0, 1, 2, 3, 4, 5, 6 or 7, with the proviso that n+m is zero or an integer from 1 to 7, for example where n is 0 and m is 1 or 2 or alternatively, for example, where n is 1 or 2 and m is 0.

In one embodiment L is $—OCH_2—$, $—OCH_2CH_2—$, $—CH_2O—$ or $—CH_2CH_2O—$.

In one embodiment L is a branched chain linker $R^aO(CH_2)_m$ wherein m is zero or an integer 1, 2, 3, 4 or 5 and $R^a$ is a $C_{2-7}$ branched alkyl, with the proviso that the number of carbons in $R^a$+m is an integer from 2 to 7, especially where m is zero, such as $—CH(CH_3)O—$, $—C(CH_3)_2O—$, $—CH_2CH(CH_3)O—$, $—CH(CH_3)CH_2O—$, $—C(CH_3)_2CH_2O—$ or $—CH_2C(CH_3)_2O$, in particular $—CH(CH_3)O—$.

In one embodiment L is a branched chain linker $(CH_2)_nOR^b$ wherein n is zero or an integer 1, 2, 3, 4 or 5 and $R^b$ is a $C_{2-7}$ branched alkyl, with the proviso that the number of carbons in $R^b$+n is an integer from 2 to 7, for example n is zero, such as $—OCH(CH_3)—$, $—OC(CH_3)_2—$, $—OCH_2CH(CH_3)—$, $—OCH(CH_3)CH_2—$, $—OC(CH_3)_2CH_2—$ or $—OCH_2C(CH_3)_2$ in particular $—OCH(CH_3)—$ or $—OC(CH_3)_2CH_2—$.

In one embodiment L is a branched chain linker $R^aOR^b$ wherein $R^a$ and $R^b$ are independently selected from a $C_{2-7}$ branched alkylene with the proviso that the number of carbons in $R^a$+$R^b$ is an integer from 4 to 7.

In one embodiment L is a saturated unbranched $C_1$-$C_8$ alkylene chain or a saturated branched or unbranched $C_{2-8}$ alkylene chain.

In one embodiment at least one carbon in L is replaced by $—O—$.

In one embodiment L is $—O—$.

Alkylene as employed herein refers to branched or unbranched carbon radicals, such as methylene ($—CH_2—$) or chains thereof. In the context of the present specification where alkyl is a linker then the latter is used interchangeably with the term alkylene.

In one embodiment the chain L includes 1, 2 or 3 halogen atom substituents, independently selected from fluoro, chloro, and bromo, for example an alkylene carbon may incorporate one or two chlorine atoms or one or two fluorine atoms and a terminal carbon atom, for example of a branch of an alkylene chain, may be bonded to one, two or three fluorine atoms or one, two or three chlorine atoms to provide a radical such as a trifluoromethyl or a trichloromethyl group.

In one embodiment the chain L does not include a halogen atom or atoms.

In one embodiment $R^3$ is H.

In one embodiment $R^3$ is methyl, ethyl, n-propyl or iso-propyl.

In one embodiment $R^3$ is cyclopropyl.

In one embodiment X is selected from, pyrrole, oxazole, thiazole, isothiazole, imidazole, pyrazole, isoxazole, oxadiazole, pyridazine, pyrimidine, pyrazine, or 1,2,3 and 1,2,4 triazole, such as pyrazole, isoxazole, oxadiazole, pyridine, pyridazine, pyrimidine, pyrazine, or 1,2,3 and 1,2,4 triazole, in particular, pyrimidine, imidazole or pyridine, and especially pyridine or pyrimidine, more specifically pyridine.

In one embodiment 1, 2, 3 or 4 carbon atoms are replaced in the alkyl chain of Q by heteroatoms independently selected from O, N, $S(O)_p$.

In one embodiment the heteroatom(s) replacing carbon(s) in the alkyl chain fragment of Q are selected from N and O.

In one embodiment Q is a saturated or unsaturated, branched or unbranched $C_{1-8}$ alkyl chain or a $C_{1-6}$ alkyl chain, wherein at least one carbon is replaced by a heteroatom selected from $—O—$, $—N—$, $S(O)_p$. Alternatively, in this embodiment the alkyl chain may be a $C_{2-8}$ alkyl or a $C_{3-6}$ alkyl group, such as a $C_4$ alkyl or a $C_5$ alkyl group.

In one embodiment a nitrogen atom in the alkyl chain is directly bonded to the carbonyl of the fragment $—NR^3C(O)$ and additionally may, for example, be a terminal amino group.

In one embodiment Q represents $C_{1-6}$ alkylNH$_2$ or NH$_2$.

In one embodiment Q represents $—NHC_{1-6}$ alkyl such as $—NHCH_3$ or $—NHCH_2CH_3$ or $—NHCH(CH_3)_2$.

In one embodiment the fragment Q is a saturated or unsaturated, branched or unbranched $C_{1-10}$ alkyl chain wherein at least one carbon (for example 1, 2, 3 or 4 carbons, in particular 1 or 2 carbons) is replaced by a heteroatom selected from O, N, $S(O)_p$, for example in such a manner as to provide a stable N-acyl group, $NR^3C(O)Q$, wherein said chain is optionally substituted by one or more groups selected from oxo, halogen, an aryl group, a heteroaryl group, a heterocyclyl group, or $C_{3-8}$ cycloalkyl each aryl, heteroaryl or heterocyclyl or $C_{3-8}$ cycloalkyl group bearing 0 to 3 substituents independently selected from a relevant substituent listed above for compounds of formula (I).

In one embodiment the fragment Q is a saturated or unsaturated, branched or unbranched $C_{1-10}$ alkyl chain wherein at least one carbon (for example 1, 2, 3 or 4 carbons, in particular 1 or 2 carbons) is replaced by a heteroatom selected from O, N, S(O)$_p$, for example in such a manner as to provide a stable N-acyl group, NR$^3$C(O)Q, wherein said chain is optionally substituted by one or more groups selected from oxo, halogen, an aryl group, a heteroaryl group or a heterocyclyl group, each aryl, heteroaryl or heterocyclyl group bearing 0 to 3 substituents independently selected from a relevant substituent listed above for compounds of formula (I), for example halogen, $C_{1-6}$ alkyl, $C_{1-6}$ alkoxy, $C_{1-6}$ haloalkyl, amino, $C_{1-4}$ mono or di-alkyl amino and $C_{1-4}$ mono or di-acyl amino.

In one embodiment the latter chain is optionally substituted by one or more groups selected from oxo, halogen, an aryl group, a heteroaryl group or a heterocyclyl group, each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, and $C_{1-4}$ mono or di-alkyl amino.

In one embodiment Q is $C_{1-4}$alkyl-V—R$^4$, such as $C_{1-3}$alkyl-V—R$^4$ wherein:
V is a heteroatom selected from NR$^V$, O or S(O)$_p$;
R$^V$ represents H or $C_{1-3}$ alkyl;
R$^4$ is H or —$C_{1-3}$ alkyl, and p is as defined above,
with the proviso that the total alkyl chain length is not more than 10 carbon atoms, including replacement heteroatoms and that the resulting radical Q is a stable group, for example —CH$_2$SCH$_3$, —CH$_2$SO$_2$CH$_3$, —CH$_2$NHCH$_3$, —CH$_2$N(CH$_3$)$_2$—C(CH$_3$)$_2$NHCH$_3$, —CH(CH$_3$)N(CH$_3$)$_2$, —(CH$_2$)$_3$CHNHCH$_3$, —(CH$_2$)$_3$N(CH$_3$)$_2$, —CH$_2$OH, —CH$_2$OCH$_3$, —CH(CH$_3$)OCH$_3$, or —(CH$_2$)$_2$OCH$_3$.

In one embodiment Q is $C_{1-3}$ alkyl-V—($C_{1-3}$ alkyl-Z—R$^5$)$_k$ such as $C_{1-3}$ alkyl-V—($C_{2-3}$ alkyl-Z—R$^5$)$_k$ wherein:
V is a heteroatom selected from N, NH, O or S(O)$_p$, such as N or NH
(V is N in the case where k=2, or will be selected from NH, O or S(O)$_p$, in the case where k=1, in particular NH);
Z is independently selected from NH, O or S(O)$_p$;
R$^5$ is H or —$C_{1-3}$alkyl;
k is an integer 1 or 2 (such as 1); and
p is as defined above,
with the proviso that the total alkyl chain length is not more than 10 carbon atoms, including replacement heteroatoms and that the resulting radical Q is a stable group. Suitably Q is $C_{1-3}$alkyl-V—$C_{1-3}$alkyl-OCH$_3$ for example $C_{1-3}$alkyl-V—$C_{2-3}$alkyl-OCH$_3$ such as $C_{1-3}$alkyl-V—(CH$_2$)$_2$OCH$_3$, in particular —CH$_2$O(CH$_2$)$_2$OCH$_3$ and CH$_2$S(CH$_2$)$_2$OCH$_3$, or —CH$_2$NH(CH$_2$)$_2$OCH$_3$, $C_{1-3}$alkyl-V—($C_{1-3}$alkyl-OCH$_3$)$_k$ wherein k represents 2, for example $C_{1-3}$alkyl-V—($C_{2-3}$ alkyl-OCH$_3$)$_k$ such as —CH$_2$N[(CH$_2$)$_2$OCH$_3$]$_2$.

In one embodiment Q is $C_{1-3}$ alkyl-V—$C_{1-2}$ alkyl-Z—$C_{1-2}$ alkyl-Y—R$^6$, or $C_{1-3}$ alkyl-V—$C_{2-3}$ alkyl-Z—$C_{2-3}$ alkyl-Y—R$^6$, wherein V, Z and Y are independently a heteroatom selected from NH, O or S(O)$_p$,
R$^6$ is H or methyl, and
p is as defined above,
with the proviso that the total alkyl chain length is not more than 10 carbon atoms, including replacement heteroatoms and that the resulting radical Q is a stable group. Suitably Q is —CH$_2$V(CH$_2$)$_2$O(CH$_2$)$_2$OCH$_3$, such as —CH$_2$O(CH$_2$)$_2$O(CH$_2$)$_2$OCH$_3$, —CH$_2$NH(CH$_2$)$_2$O(CH$_2$)$_2$OCH$_3$, or —CH$_2$S(CH$_2$)$_2$O(CH$_2$)$_2$OCH$_3$.

In one embodiment Q represents —NR$^7$R$^8$ and —NR$^3$C(O)Q forms a urea, where R$^7$ and R$^8$ independently represent hydrogen or a $C_{1-9}$ saturated or unsaturated, branched or unbranched alkyl chain, wherein one or more carbons, such as 1, 2 or 3 are optionally replaced by a heteroatom selected from O, N or S(O)$_p$. Said chain is optionally substituted by one or more groups independently selected from oxo, halogen, an aryl group, a heteroaryl group, a heterocyclyl or $C_{3-8}$ cycloalkyl group, each aryl, heteroaryl or heterocyclyl group bearing 0 to 3 substituents independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono or di-alkyl amino and $C_{1-4}$ mono or di-acyl amino with the proviso that the total alkyl chain length is not more than 10 carbon atoms, including replacement heteroatoms and that the resulting radical Q is a stable group.

In one embodiment Q represents —NR$^7$R$^8$ and —NR$^3$C(O)Q forms a urea, where R$^7$ and R$^8$ independently represent hydrogen or a $C_{1-9}$ saturated or unsaturated, branched or unbranched alkyl chain, wherein one or more carbons, such as 1, 2 or 3 are optionally replaced by a heteroatom selected from O, N or S(O)$_p$. Said chain is optionally substituted by one or more groups independently selected from oxo, halogen, an aryl group, a heteroaryl group or a heterocyclyl group, each aryl, heteroaryl or heterocyclyl group bearing 0 to 3 substituents independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono or di-alkyl amino and $C_{1-4}$ mono or di-acyl amino with the proviso that the total alkyl chain length is not more than 10 carbon atoms, including replacement heteroatoms and that the resulting radical Q is a stable group.

In this urea embodiment in one sub-embodiment R$^7$ represents hydrogen.

Examples of ureas include those in which R$^7$ and R$^8$ are both hydrogen and Q is —NH$_2$, or where Q is —NHCH$_3$ or —N(CH$_3$)$_2$ to provide, for example, a fragment —NR$^3$C(O)NH$_2$ or —NR$^3$C(O)NHCH$_3$ or —NR$^3$C(O)N(CH$_3$)$_2$.

Examples of ureas containing a heteroatom in the alkyl chain include those in which Q is —NH(CH$_2$)$_2$OCH$_3$ or —N[(CH$_2$)$_2$OCH$_3$]$_2$. In one embodiment Q represents —NHC$_{2-6}$alkylOC$_{1-3}$alkyl, such as —NHCH$_2$CH$_2$OCH$_3$.

Examples of ureas containing an oxo substituent include those in which Q is NHCH$_2$C(O)NH—$C_{2-3}$alkyl-X$^1$—$C_{1-3}$ alkyl, wherein X$^1$ is a heteroatom selected from N, O or S(O)$_p$ and p is defined as above. Examples of the latter include those wherein Q is —NHCH$_2$C(O)NHCH$_2$CH$_2$OCH$_3$. Thus in one embodiment Q represents —NHC$_{1-4}$ alkylC(O)NHC$_2$alkylOCH$_3$ such as —NHCH$_2$C(O)NHCH$_2$CH$_2$OCH$_3$.

In one embodiment Q represents —NHC$_{1-4}$alkylC(O)R$^Q$ wherein R$^Q$ is selected from OH or —NR'R'' where R' is hydrogen or $C_{1-3}$ alkyl and R'' is hydrogen or $C_{1-3}$ alkyl, for example —NHCH$_2$C(O)OH, —NHCH$_2$C(O)NH$_2$ or —NHCH$_2$C(O)NHCH$_3$ such as —NHCH$_2$C(O)OH or —NHCH$_2$C(O)NHCH$_3$.

In one embodiment Q represents —NHC$_{1-4}$alkylC(O)OC$_{1-3}$alkyl, such as —NHCH$_2$C(O)OCH$_2$CH$_3$.

In a further urea sub-embodiment Q represents —N—R$^9$C$_{1-3}$ alkyl-V—($C_{1-3}$ alkyl-Z—R$^{10}$)$_k$ for example —N—R$^9$C$_{2-3}$ alkyl-V—($C_{2-3}$ alkyl-Z—R$^{10}$)$_k$ wherein:
V represents N, NH, O, S(O)$_p$;
Z represents NH, O, S(O)$_p$;
k is an integer 1 or 2;
p is an integer 0, 1 or 2
R$^9$ represents H or $C_{1-3}$ alkyl-V—($C_{1-3}$ alkyl-Z—R$^{10}$)$_k$ such as $C_{2-3}$ alkyl-V—($C_{2-3}$ alkyl-Z—R$^{10}$)$_k$; and
R$^{10}$ is H or $C_{1-3}$ alkyl such as $C_{1-3}$ alkyl;

with the proviso that the total alkyl chain length is not more than 10 carbon atoms, including replacement heteroatoms and that the resulting radical Q is a stable group.

In one embodiment Q is a saturated or unsaturated, branched or unbranched $C_{1-10}$ alkyl chain, wherein at least one carbon is replaced by a heteroatom selected from O, N, and $S(O)_p$, wherein said chain is substituted by an aryl group bearing 0 to 3 substituents, for example 1, 2 or 3, such as 1 or 2 substituents independently selected from the relevant substituents listed above for compounds of formula (I), for example from halogen, $C_{1-6}$ alkyl, $C_{1-6}$ alkoxy, $C_{1-6}$ haloalkyl, amino and $C_{1-4}$ mono or di-alkyl amino and $C_{1-4}$ mono or di-acyl amino, such as a saturated or unsaturated, branched or unbranched $C_{1-10}$ alkyl chain, wherein at least one carbon is replaced by a heteroatom selected from O, N, and $S(O)_p$, wherein said chain is substituted by an aryl group bearing 0 to 3 substituents, for example 1, 2 or 3, such as 1 or 2 substituents independently selected from halogen, $C_{1-6}$ alkyl, $C_{1-6}$ alkoxy, $C_{1-6}$ haloalkyl, amino and $C_{1-4}$ mono or di-alkyl amino. In one embodiment the said aryl group is phenyl, for example substituted phenyl or unsubstituted phenyl.

In one embodiment Q represents —$NHC_{0-6}$ alkylphenyl, such as —NHphenyl or NHbenzyl.

Examples of the fragment —$NR^3C(O)Q$ wherein Q comprises substituted benzyl include: —$NR^3C(O)CH_2NHCH_2C_6H_4(OCH_3)$ such as —$NHC(O)CH_2NHCH_2C_6H_4(OCH_3)$, for example where the methoxy substituent is in the ortho, meta or para position, such as the para position.

In one embodiment Q is a saturated or unsaturated, branched or unbranched $C_{1-10}$ alkyl chain, wherein at least one carbon is replaced by a heteroatom selected from O, N, and $S(O)_p$, wherein said chain is substituted by a heteroaryl group bearing 0 to 3 substituents (for example 1, 2 or 3, such as 1 or 2 substituents) independently selected from the relevant substituents listed above for compounds of formula (I), for example halogen, $C_{1-6}$ alkyl, $C_{1-6}$ alkoxy, $C_{1-6}$ alkyl amino, $C_{1-4}$ mono or di-alkyl amino and $C_{1-4}$ mono or di-acyl amino, such as a saturated or unsaturated, branched or unbranched $C_{1-10}$ alkyl chain, wherein at least one carbon is replaced by a heteroatom selected from O, N, and $S(O)_p$, wherein said chain is substituted by a heteroaryl group bearing 0 to 3 substituents for example 1, 2 or 3, such as 1 or 2 substituents selected from halogen, $C_{1-6}$ alkyl, $C_{1-6}$ alkoxy, $C_{1-6}$ alkyl amino, $C_{1-4}$ mono or di-alkyl amino. In one embodiment the said heteroaryl group is selected from, thiophene, oxazole, thiazole, isothiazole, imidazole, pyrazole, isoxazole, isothiazole, oxadiazole, 1,2,3 or 1,2,4 triazole, pyridine, pyridazine, pyrimidine, pyrazine and, in particular pyridine and pyrimidine, especially pyridine.

In one embodiment Q represents —$NHC_{1-6}$ alkylheteroaryl, for example —$NH(CH_2)_3$imidazolyl or —$NHCH_2$ isoxazole wherein the isoxazole is optionally substituted such as —$NHCH_2$ isoxazole($CH_3$).

In one embodiment Q represents —$NHC_{1-4}$ alkylC(O) $NHC_{1-3}$alkylheteroaryl, for example a nitrogen containing heteroaryl group or a nitrogen and oxygen containing heteroaryl, more specifically —$NHCH_2C(O)NHCH_2CH_2$pyridinyl, in particular where pyridinyl is linked through carbon, for example pyridin-4-yl or —$NHCH_2C(O)NHCH_2CH_2CH_2$imidazolyl, in particular where imidazolyl is linked through nitrogen.

In one embodiment Q is a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents (for example 1, 2 or 3, such as 1 or 2 substituents) independently selected from the relevant substituents listed above for compounds of formula (I), for example halogen, $C_{1-6}$ alkyl, $C_{1-6}$ alkoxy, $C_{1-6}$ haloalkyl amino, $C_{1-4}$ mono or di-alkyl amino and $C_{1-4}$ mono or di-acyl amino, such as a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents, for example 1, 2 or 3, such as 1 or 2 substituents selected from halogen, $C_{1-6}$ alkyl, $C_{1-6}$ alkoxy, $C_{1-6}$ haloalkyl amino, $C_{1-4}$ mono or di-alkyl amino.

In one embodiment said heterocyclyl is selected, from a 5 or 6 membered saturated or partially unsaturated ring system comprising one or more (for example 1, 2 or 3 in particular 1 or 2) heteroatoms independently selected from O, N and S, for example pyrrolidine, tetrahydrofuran, tetrahydrothiophene, piperidine, piperazine, morpholine, 1,4-dioxane, pyrrolidine and oxoimidazolidine such as pyrrolidine, tetrahydrofuran, tetrahydrothiophene, piperidine, piperazine, morpholine, and 1,4-dioxane, in particular piperidine, piperazine, and morpholine.

A heterocyclic group may be linked to the alkyl chain of Q or to the carbonyl of —$NR^3C(O)$— through carbon or nitrogen, in particular a nitrogen atom.

In one embodiment Q is —$C_{0-3}$alkylheterocycle (for example —$C_{0-1}$alkylheterocycle) said heterocyclyl group comprising at least one heteroatom (for example 1, 2 or 3, in particular 1 or 2, heteroatoms) selected from O, N and S, and is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino and $C_{1-4}$ mono or di-acyl amino.

In one embodiment Q is —$C_0$alkylheterocycle, for example a tetrahydropyranyl or a pyrrolidinyl or a morpholinyl or a piperazinyl or an oxoimidazolinyl group, such as 2-oxoimidazolidinyl group.

In one embodiment in which Q is —$C_0$alkylheterocycle, the heterocycle is linked through carbon, and is, for example, a C-linked tetrahydropyran or a C-linked piperidine or a C-linked morpholine or a C-linked piperazine.

In one embodiment in which Q is —$C_0$alkylheterocycle, the heterocyclic group containing one or more N atoms is linked through N. This embodiment provides for ureas in which one of the urea nitrogens is embedded within a heterocyclic ring. Examples of this embodiment include, but are not limited to, an N-linked morpholine or an N-linked piperidine or an N-linked piperazine, said N-linked piperizinyl group optionally bearing an additional C- or N-substituent (such as an N-methyl group or N—$CH_2CH_2OCH_3$ group. In one embodiment Q is a heterocyclyl linked through nitrogen such as piperidinyl, in particular 4-hydroxypiperidinyl or piperazinyl, such as 4-methyl piperazinyl.

In one embodiment Q represents a heterocyclyl group, for example a nitrogen containing heterocyclyl group, in particular linked through N, such as morpholinyl or piperazinyl optionally substituted by methyl, especially 4-methyl, or piperidinyl.

In one embodiment Q is a —$C_1$alkylheterocycle, for example tetrahydropyranylmethyl or a C- or N-linked piperazinylmethyl optionally bearing a substituent (for example a $C_{1-6}$ alkyl substitutent such as methyl or a $C_{1-6}$ alkoxy substituent such as —$CH_2CH_2OCH_3$). Additional examples include a C- or N-linked pyrrolidinylmethyl, or a C- or N-linked oxoimidazolinylmethyl (such as 2-oxoimidazolidinylmethyl, said heterocycle optionally bearing a substituent (such as N-methyl or N—$SO_2CH_3$).

In one embodiment Q represents —NHheterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or di-alkyl amino, —$S(O)_q C_{1-6}$ alkyl, $C_{1-4}$ mono or di-acyl amino, $C_{0-6}$ alkylC(O)$C_{1-6}$ alkyl or $C_{0-6}$ alkylC(O)$C_{1-6}$ heteroalkyl), such as where the ring is linked through carbon, for example 2-piperidinyl or 3-piperidinyl or 4-piperidinyl, in particular 1-acetylpiperidin-4-yl, 1-methylpiperidin-4-yl, 1-(methylsulfonyl)piperidin-4-yl or 1-(2-(2-methoxyethoxy)acetyl)piperidin-4-yl In one embodiment Q represents —NH$C_{1-6}$ alkylheterocyclyl for example a nitrogen containing heterocyclyl group, in particular one linked through nitrogen, such as —NH$CH_2CH_2$morpholine, —NH$(CH_2)_3$morpholine or —NH$(CH_2)_4$morpholine.

In one embodiment Q represents —NH$C_{1-6}$ alkylC(O)heterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $C_{0-6}$ alkylC(O) $C_{1-6}$ alkyl or $C_{0-6}$ alkylC(O)$C_{1-6}$ heteroalkyl) for example a nitrogen containing heterocyclyl group, in particular one linked through nitrogen, such as —NH$CH_2$C(O)-1-pyrrolindinyl, NH$CH_2$C(O)-1-piperidinyl, —NH$CH_2$C(O)-4-morpholinyl or —NH$CH_2$C(O)piperazinyl such as —NH$CH_2$C(O)-4-methyl-1-piperazinyl.

In one embodiment Q represents —NH$C_{1-4}$ alkylC(O) NH$C_{1-3}$alkylheterocyclyl for example a nitrogen containing heterocyclyl group or a nitrogen and/or oxygen containing heterocyclyl, such as —NH$CH_2$C(O) NH$CH_2CH_2$morpholinyl, in particular where morpholinyl is linked through nitrogen.

In one embodiment Q represents —N($C_{1-3}$ alkyl)$C_{1-6}$ alkylheterocyclyl, for example a nitrogen containing heterocyclyl group, in particular linked through nitrogen, such as —N($CH_3$)$CH_2CH_2$morpholine, —N($CH_3$)$(CH_2)_3$morpholine or —N($CH_3$)$(CH_2)_4$morpholine.

In one embodiment Q is —$C_{1-3}$alkyl-G-$C_{1-3}$alkylheterocycle wherein G is a heteroatom selected from NH, O or $S(O)_p$ said heterocyclyl group comprising at least one heteroatom (for example 1, 2 or 3, in particular 1 or 2, heteroatoms) selected from O, N, and S, and is optionally substituted by one or two or three groups independently selected from relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino and $C_{1-4}$ mono or di-acyl amino such as one or two or three groups halogen, $C_{1-6}$ alkyl, $C_{1-6}$ alkoxy, $C_{1-6}$ haloalkyl, amino, $C_{1-4}$ mono and di-alkyl amino. Suitably Q is —$CH_2$G$(CH_2)_2$heterocycle for example —$CH_2$G$(CH_2)_2$tetrahydropyranyl; or —$CH_2$G$(CH_2)_2$morpholinyl in which the heterocyclyl is linked through nitrogen or carbon; or $CH_2$G$(CH_2)_2$piperazinyl in which the heterocyclyl is linked through nitrogen or carbon and optionally bearing a further C- or N-substituent (for example a $C_{1-6}$ alkyl substituent such as methyl or a $C_{1-6}$ alkoxy substituent such as —$CH_2CH_2OCH_3$); or —$CH_2$G $(CH_2)_2$pyrrolidinyl, in which the heterocyclyl is linked through nitrogen or carbon, for example linked through nitrogen; or —$CH_2$G$(CH_2)_2$oxoimidazolinyl (such as 2-oxoimidazolidinyl) for example linked through N and optionally bearing an additional C- or N-substituent (such as N-methyl or N—$SO_2CH_3$), and in which G is O or NH.

In one embodiment G is O.

In one embodiment G is NH.

In one embodiment Q is a saturated or unsaturated $C_{1-10}$ alkyl chain wherein at least one carbon (for example 1, 2 or 3 carbons) is replaced by a heteroatom selected from O, N, $S(O)_p$ wherein said chain is substituted by a $C_{3-8}$ carbocyclyl group and said alkyl chain is optionally substituted by one or more (for example 1 or 2) groups selected from oxo and halogen. In one embodiment said $C_{3-8}$ carbocyclyl group bears one or more groups (for example 1, 2 or 3 groups) independently selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)$C_{1-6}$ alkyl or $C_{0-6}$ alkylC(O)$C_{1-6}$ heteroalkyl.

In one embodiment Q represents —NH$C_{3-6}$ cycloalkyl, such as —NHcyclopropyl, —NHcyclopentyl or —NHcyclohexyl.

In one embodiment the aryl, heteroaryl or heterocyclyl group bears at least one —$S(O)_q C_{1-6}$ alkyl substitutent and optionally bears one or two further relevant substituents independently selected from the list of substituents defined above for compounds of formula (I).

In one embodiment the $C_{5-6}$ heterocycle bears at least one —$S(O)_q C_{1-6}$ alkyl substituent and optionally bears one or two further substituents independently selected from the relevant list of substituents defined above for compounds of formula (I).

In one embodiment the aryl, heteroaryl or heterocyclyl group bears at least one hydroxyl substituent and optionally bears one or two further substituents independently selected from the relevant list of substituents defined above for compounds of formula (I).

In one embodiment the $C_{5-6}$heterocycle bears at least one hydroxyl substituent and optionally bears one or two further substituents independently selected from the relevant list of substituents defined above for compounds of formula (I).

In one embodiment the aryl, heteroaryl or heterocyclyl group bears at least one $C_{1-4}$ mono and/or di-acyl amino substituent and optionally bears one or two further substituents independently selected from the relevant list defined above for compounds of formula (I).

In one embodiment the $C_{5-6}$heterocycle bears at least one $C_{1-4}$ mono and/or di-acyl amino substituent and optionally bears one or two further substituents independently selected from the relevant list defined above for compounds of formula (I).

In one embodiment the aryl, heteroaryl or heterocyclyl group bears at least one $C_{0-6}$ alkylC(O)$C_{1-6}$ heteroalkyl substituent and optionally bears one or two further substituents independently selected from the relevant list defined above for compounds of formula (I).

In one embodiment the $C_{5-6}$heterocycle bears at least one $C_{0-6}$ alkylC(O)$C_{1-6}$ heteroalkyl substituent and optionally bears one or two further substituents independently selected from the relevant list defined above for compounds of formula (I).

In one embodiment the aryl, heteroaryl or heterocyclyl group bears at least one $C_{0-6}$ alkylC(O)$C_{1-6}$ alkyl substituent and optionally bears one or two further substituents independently selected from the relevant list defined above for compounds of formula (I).

In one embodiment the $C_{5-6}$heterocycle bears at least one $C_{0-6}$ alkylC(O)$C_{1-6}$ alkyl substituent and optionally bears one or two further substituents independently selected from the relevant substituents defined above for compounds of formula (I).

In one embodiment Q represents tetrahydrofuranyl, morpholinyl, piperidinyl such as piperidinyl bearing one hydroxyl substituent, piperazinyl such as piperazinyl bearing one methyl substituent or pyrrolidinyl such a pyrrolidinyl bearing one di-methyl amino substituent. The ring may be linked through the heteroatom, such as nitrogen. Alternatively, the ring may be linked through carbon. The substituent may, for example be para relative to the atom through which the ring is linked to the remainder of the molecule.

In one embodiment the alkyl chain fragment of Q does not bear any optional substituents.

In one embodiment the alkyl chain is saturated.

In one embodiment the alkyl chain is unbranched.

In one embodiment the alkyl chain fragment of Q bears 1, 2, or 3, for example 1 or 2, in particular 1 optional substituent.

It will be clear to persons skilled in the art that the heteroatom may replace a primary, secondary or tertiary carbon, that is a $CH_3$, —$CH_2$— or a —CH—, group, as technically appropriate.

In one embodiment p is 0 or 2.

In one embodiment p is 1.

In one embodiment compounds of the disclosure include those in which the fragment Q is:
- —$CH_2OH$;
- —$CH_2OC_{1-6}$ alkyl, in particular —$CH_2OCH_3$;
- —$CH_2CH_2OCH_3$;
- —$CH_2$—O—$(CH_2)_2OCH_3$;
- —$CH(CH_3)OCH_3$;
- —$CH_2NHCH_3$ or $CH_2N(OH_3)_2$
- —$CH_2NHCH_2CH_2OCH_3$ or —$CH_2NHC(O)CH_2OCH_3$;
- —$CH_2SCH_3$, —$CH_2S(O)_2CH_3$ or —$CH_2NHC(O)CH_2S(O)_2CH_3$; or
- —$CH_2NHC(O)CH_2$.

In one embodiment compounds of the disclosure include those in which the fragment —$NR^3C(O)Q$ in formula (I) is represented by:
- —$NR^3C(O)CH_2OH$, in particular —$NHC(O)CH_2OH$;
- —$NR^3C(O)CH_2OC_{1-6}$ alkyl, in particular —$NR^3C(O)CH_2OCH_3$, especially —$NHC(O)CH_2OCH_3$;
- —$NR^3C(O)CH_2O(CH_2)_2OCH_3$, in particular —$NHC(O)CH_2O(CH_2)_2OCH_3$;
- —$NR^3C(O)CH(CH_3)OCH_3$ in particular —$NHC(O)CH(CH_3)OCH_3$;
- —$NR^3C(O)CH(CH_3)NHC_{1-3}$alkyl in particular $NHC(O)CH(CH_3)NHCH_3$;
- —$NR^3C(O)CH(CH_3)N(C_{1-3}alkyl)_2$ in particular $NHC(O)CH(CH_3)N(OH_3)_2$;
- —$NR^3C(O)C(CH_3)_2NHCH_3$ in particular $NHC(O)C(CH_3)_2NHCH_3$;
- —$NR^3C(O)(CH_2)_2OC_{1-6}$alkyl, such as —$NR^3C(O)(CH_2)_2OCH_3$, in particular —$NHC(O)(CH_2)_2OCH_3$;
- —$NR^3C(O)(CH_2)_3NHC_{1-3}$alkyl in particular —$NHC(O)(CH_2)_3NHCH_3$;
- —$NR^3C(O)(CH_2)_3N(C_{1-3}alkyl)_2$ in particular —$NHC(O)(CH_2)_3N(CH_3)_2$;
- —$NR^3C(O)CH_2NHC_{1-3}$alkyl in particular —$NHC(O)CH_2NHCH_3$;
- —$NR^3C(O)CH_2NH(CH_2)_2OCH_3$ in particular —$NHC(O)CH_2NH(CH_2)_2OCH_3$;
- —$NR^3C(O)CH_2SCH_3$, in particular —$NHC(O)CH_2SCH_3$;
- —$NR^3C(O)CH_2S(CH_2)_2OCH_3$, in particular —$NHC(O)CH_2S(CH_2)_2OCH_3$;
- —$NR^3C(O)CH_2S(CH_2)_2O(CH_2)_2OCH_3$, in particular —$NHC(O)CH_2S(CH_2)_2O(CH_2)_2OCH_3$
- —$NR^3C(O)CH_2SOCH_3$, in particular —$NHC(O)CH_2SOCH_3$
- —$NR^3C(O)CH_2S(O)_2CH_3$, in particular —$NHC(O)CH_2S(O)_2CH_3$;
- —$NR^3C(O)CH_2N[(CH_2)_2OCH_3]_2$ in particular —$NHC(O)CH_2N[(CH_2)_2OCH_3]_2$;
- —$NR^3C(O)NH_2$ in particular —$NHC(O)NH_2$;
- —$NR^3C(O)NHC_{1-9}$ alkyl, such as $NR^3C(O)NHC_{1-7}$ alkyl, in particular —$NHC(O)NHCH_3$
- —$NR^3C(O)N(C_{1-4}$ alkyl$)C_{1-5}$ alkyl in particular —$NHC(O)N(CH_3)_2$; or
- —$NR^3C(O)NHCH_2CONH(CH_2)_2OCH_3$ in particular —$NHC(O)NHCH_2CONH(CH_2)_2OCH_3$.

In one embodiment compounds of the disclosure include compounds of formula (I) in which the fragment —$NR^3C(O)C_{0-8}$alkylheterocyclyl is represented by:
- —$NHC(O)$-(tetrahydropyranyl), such as —$NHC(O)$-(tetrahydro-2H-pyran-4-yl):
- —$NHC(O)$-(morpholinyl) such as —$NHC(O)$-(4-morpholinyl) or —$NHC(O)$-(3-morpholinyl);
- —$NHC(O)$-(pyrrolidinyl), such as —$NHC(O)$-(pyrrolidin-1-yl);
- —$NHC(O)$-(piperazinyl), such as —$NHC(O)$-(piperazin-1-yl);
- —$NHC(O)$-(methylpiperazinyl), such as —$NHC(O)$-(4-methylpiperazin-1-yl);
- —$NHC(O)$-[(methoxyethyl)piperazinyl], such as —$NHC(O)$-[4-(2-methoxyethyl)piperazin-1-yl];
- —$NHC(O)$-(oxoimidazolidinyl) such as —$NHC(O)$-(2-oxoimidazolidinyl), in particular —$NHC(O)$-(2-oxoimidazolidin-1-yl);
- —$NHC(O)CH_2$-(tetrahydropyranyl), such as —$NHC(O)CH_2$-(tetrahydro-2H-pyran-4-yl);
- —$NHC(O)CH_2$-(morpholinyl), such as —$NHC(O)CH_2$-(4-morpholinyl);
- —$NHC(O)CH_2$-(pyrrolidinyl), such as —$NHC(O)CH_2$-(pyrrolidin-1-yl);
- —$NHC(O)CH_2$-(piperazinyl), such as —$NHC(O)CH_2$-(piperazin-1-yl);
- —$NHC(O)CH_2$-(methylpiperazinyl), such as —$NHC(O)CH_2$-(4-methylpiperazin-1-yl);
- —$NHC(O)CH_2$-[(methoxyethyl)piperazinyl], such as —$NHC(O)CH_2$-[4-(2-methoxyethyl)piperazin-1-yl];
- —$NHC(O)CH_2SCH_2CH_2$-(morpholinyl), such as —$NHC(O)CH_2SCH_2CH_2$-(4-morpholinyl), or —$NHC(O)CH_2SCH_2CH_2$-(3-morpholinyl); and
- —$NHC(O)CH_2SO_2CH_2CH_2$-(morpholinyl), such as —$NHC(O)CH_2SO_2CH_2CH_2$-(4-morpholinyl), or —$NHC(O)CH_2SO_2CH_2CH_2$-(3-morpholinyl).

In one embodiment compounds of the disclosure include compounds of formula (I) in which Q is:
- -(tetrahydropyranyl), such as -(tetrahydro-2H-pyran-4-yl);
- -(morpholinyl) such as (4-morpholinyl);
- -(pyrrolidinyl), such as (pyrrolidin-1-yl);
- -(piperazinyl), such as -(piperazin-1-yl);
- -(methylpiperazinyl), such as -(4-methylpiperazin-1-yl);
- -(methoxyethyl)piperazinyl, such as -4-(2-methoxyethyl)piperazin-1-yl;
- —$CH_2$-(tetrahydropyranyl), such as —$CH_2$-(tetrahydro-2H-pyran-4-yl);
- —$CH_2$—(morpholinyl), such as —$CH_2$-(4-morpholinyl);
- —$CH_2$-(pyrrolidinyl), such as —$CH_2$-(pyrrolidin-1-yl);
- —$CH_2$-(piperazinyl), such as —$CH_2$-(piperazin-1-yl);
- —$CH_2$-(methylpiperazinyl), such as —$CH_2$-(4-methylpiperazin-1-yl);
- —$CH_2$-[(methoxyethyl)piperazinyl], such as —$CH_2$-[4-(2-methoxyethyl)piperazin-1-yl];
- —$CH_2NHC(O)$-tetrahydrofuran such as —$CH_2NHC(O)$-(tetrahydro-2H-pyran-4-yl);

—CH₂NHC(O)-morpholinyl such as —CH₂NHC(O)-(4-morpholinyl) —CH₂NHC(O)-(piperazinyl), such as —CH₂NHC(O)-(piperazin-1-yl); and —CH₂NHC(O)-(methylpiperazinyl), such as —CH₂NHC(O)-(4-methylpiperazin-1-yl).

In one embodiment of the fragment Q, the saturated or unsaturated, branched or unbranched $C_{1-10}$ alkyl chain, wherein at least one carbon is replaced by a heteroatom selected from —O, —N, $S(O)_p$ is selected from: —CH₂OCH₂—, —CH₂NHCH₂—, —CH₂NH— and —CH₂OCH₂CH₂—. These fragments may optionally terminate in an aryl group, a heteroaryl group a heterocyclyl group or $C_{3-8}$ cycloalkyl group, such as an aryl group, a heteroaryl group a heterocyclyl group as defined for fragment Q above.

In one embodiment the disclosure relates to compounds of formula (IB):

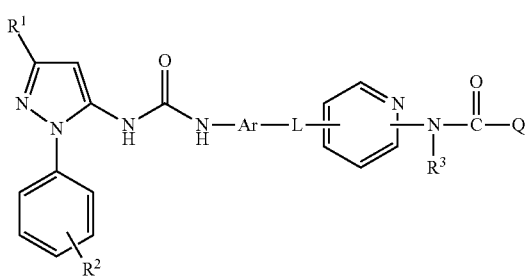

(IB)

wherein $R^1$, $R^2$, Ar, L, $R^3$ and Q are as defined above.

In one embodiment of the compounds of formula (IB) the substituent —NR³C(O)Q is in the 2 or 3 position.

In a further embodiment the disclosure relates to compounds of formula (IC):

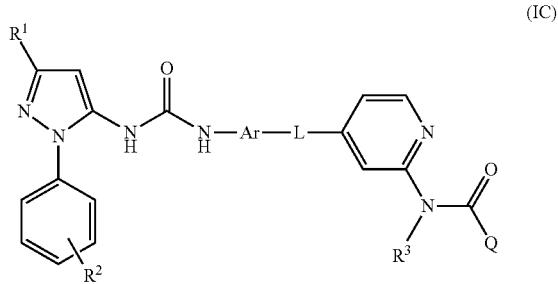

(IC)

wherein $R^1$, $R^2$, Ar, L, $R^3$ and Q are as defined above.

In yet another embodiment the disclosure relates to compounds of formula (ID):

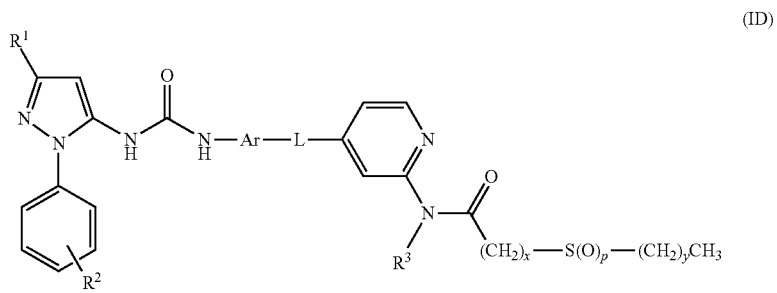

(ID)

wherein $R^1$, $R^2$, Ar, L and $R^3$ are as defined above and p is 0, 1 or 2, in particular 0 or 2, and x is an integer from 1 to 6 (including 2, 3, 4 and 5) and y is zero or an integer from 1 to 5 (including 2, 3 and 4) with the proviso that x+y is an integer from 1 to 8 such as 1 to 6, for example x is 1 and y is 1.

In one embodiment the disclosure relates to compounds of formula (IE):

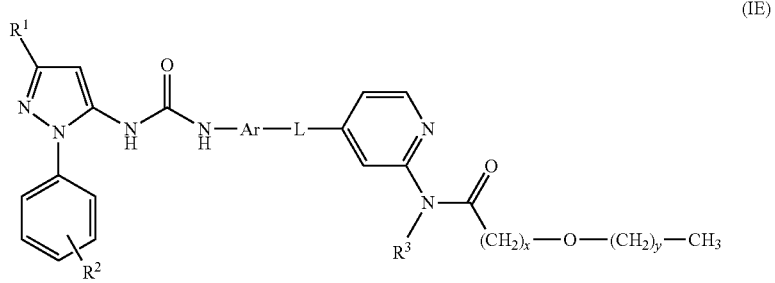

(IE)

wherein R¹, R², Ar, L and R³ are as defined above
x is an integer from 1 to 6 (including 2, 3, 4 and 5) and y is zero or an integer from 1 to 5 (including 2, 3 and 4), with the proviso that x+y is an integer from 1 to 6, for example x is 1 and y is 0.

In one embodiment of the compounds of formula (IE) the fragment represented by —NR³C(O)(CH₂)ₓO(CH₂)ᵧCH₃ is: —NR³C(O)CH₂OCH₃, especially —NHC(O)CH₂OCH₃.

In one embodiment the disclosure relates to compounds of formula (IF):

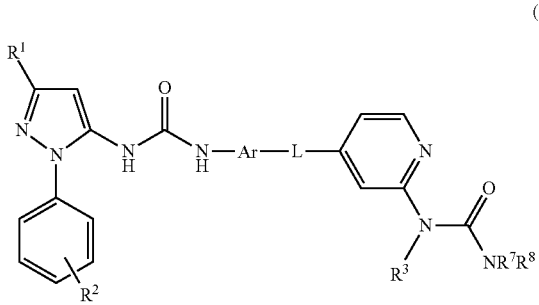

(IF)

wherein R¹, R², Ar, L, R³, R⁷ and R⁸ are as defined above.

In one embodiment the disclosure relates to compounds of formula (IG):

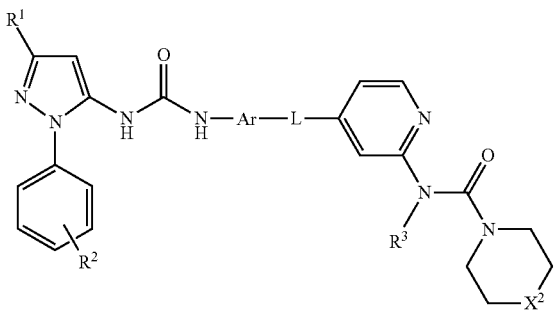

(IG)

wherein R¹, R², Ar, L and R³ are as defined above and X² represents O, CH₂, NH, NCH₃ or NCH₂CH₂OCH₃.

In one aspect there is provided a compound of formula (IH):

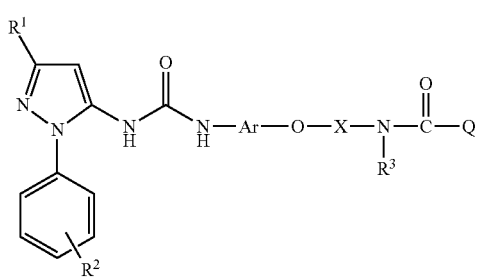

(IH)

wherein R¹ is $C_{1-6}$ alkyl optionally substituted by a hydroxyl group;

R² is H or $C_{1-6}$ alkyl optionally substituted by a hydroxyl group;

R³ is H, $C_{1-6}$ alkyl or $C_{0-3}$ alkyl$C_{3-6}$ cycloalkyl;

Ar is a naphthyl or a phenyl ring either of which may be optionally substituted by one or more groups independently selected from $C_{1-6}$ alkyl, $C_{1-6}$ alkoxy, amino, $C_{1-4}$ mono or di-alkyl amino;

X is 5 or 6 membered heteroaryl group containing at least one nitrogen atom and optionally including 1 or 2 further heteroatoms selected from O, S and N;

Q is selected from:

a) a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, S(O)ₚ, wherein said chain is optionally, substituted by one or more groups (for example 1, 2 or 3) independently selected from oxo, halogen, an aryl group, a heteroaryl group, a heterocyclyl group or a $C_{3-8}$ cycloalkyl, each aryl, heteroaryl or heterocyclyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, S(O)_q$C_{1-6}$ alkyl, $C_{0-6}$ alkylC(O)$C_{1-6}$ alkyl or $C_{0-6}$ alkylC(O)$C_{1-6}$ heteroalkyl, with the proviso that the atom linked directly to the carbonyl in —NR³C(O)— is not an oxygen or a sulfur atom; and b) a $C_{0-8}$ alkyl$C_{5-6}$ heterocycle or said heterocyclyl group comprising at least one heteroatom (for example 1, 2 or 3, suitably 1 or 2, in particular 1 heteroatom) selected from O, N, and S, and is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, S(O)_q$C_{1-6}$ alkyl, $C_{0-6}$ alkylC(O)$C_{1-6}$ alkyl or $C_{0-6}$ alkylC(O)$C_{1-6}$ heteroalkyl; and p is 0, 1 or 2;

or a pharmaceutically acceptable salt thereof, including all stereoisomers, tautomers and isotopic derivatives thereof.

In one embodiment the disclosure relates to compounds of formula (IJ):

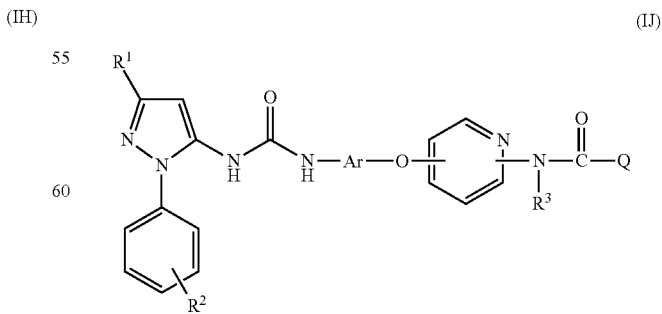

(IJ)

wherein R¹, R², Ar, R³ and Q are as defined above.

In a further embodiment the disclosure relates to compounds of formula (IK):

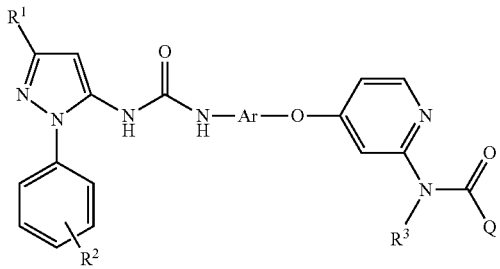

(IK)

wherein $R^1$, $R^2$, Ar, $R^3$ and Q are as defined above.

In yet another embodiment the disclosure relates to compounds of formula (IL):

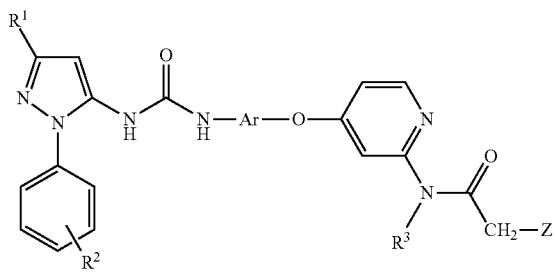

(IL)

wherein $R^1$, $R^2$, Ar and $R^3$ are as defined above and

Z represents a saturated or unsaturated, branched or unbranched $C_{1-9}$ alkyl chain, wherein at least one carbon (for example 1, 2 or 3 carbons, suitably 1 or 2, in particular 1) is replaced by a heteroatom selected from O, N, S(O)$_p$, or a $C_{0-7}$ alkyl$C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino.

In one embodiment of formula (IL) Z is —OCH$_3$ or —OCH$_2$CH$_2$OCH$_3$.

In one embodiment of formula (IL) Z is —SO$_2$CH$_3$.

In one embodiment of formula (IL) Z is —NR$^A$R$^B$ wherein R$^A$ and R$^B$ are independently selected from hydrogen, $C_{1-6}$ alkyl, and $C_{3-6}$ alkoxy such that for example Z represents —NH$_2$, —NHCH$_3$, —N(CH$_3$)$_2$ or —NHCH$_2$CH$_2$OCH$_3$.

In one embodiment of formula (IL) Z is —S(O)$_q$CH$_3$ wherein n is 0, 1 or 2, such as 0 or 2.

In one embodiment of formula (IL) Z represents a —C$_{5-6}$ heterocycle said heterocyclyl group comprising at least one heteroatom (for example 1, 2 or 3, suitably 1 or 2, in particular 1 heteroatom) selected from O, N and S, and is optionally substituted by one, two or three groups independently selected from the relevant substituents listed above for compounds of formula (I) for example halogen, $C_{1-6}$ alkyl, $C_{1-6}$ alkoxy, $C_{1-6}$ haloalkyl, amino, $C_{1-4}$ mono and di-alkyl amino, for example:

morpholinyl (in particular linked through nitrogen) or tetrahydropyranyl, or
piperazinyl (in particular linked through nitrogen) optionally substituted on the second nitrogen by —CH$_3$ or —CH$_2$CH$_2$OCH$_3$.

In one embodiment the disclosure relates to compounds of formula (IM):

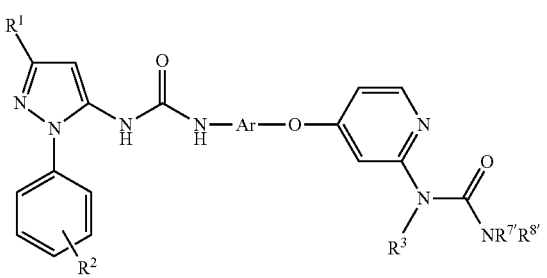

(IM)

wherein $R^1$, $R^2$, Ar and $R^3$ are as defined above and $R^{7'}$ and $R^{8'}$ independently represent hydrogen, $C_{1-6}$ alkyl, or $R^{7'}$ and $R^{8'}$ together with the nitrogen to which they are attached represent a 5 or 6 membered heterocycle optionally comprising a further heteroatom selected from O, N and S, wherein said heterocycle is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino.

In one embodiment of compounds of formula (IM) the group —NR$^{7'}$R$^{8'}$ represents —NH$_2$, —NHCH$_3$ or NHCH$_2$CH$_3$.

In one embodiment of compounds of formula (IM) —NR$^{7'}$R$^{8'}$ represents morpholinyl or piperazinyl.

In an alternative embodiment the disclosure relates to compounds of formula (IN):

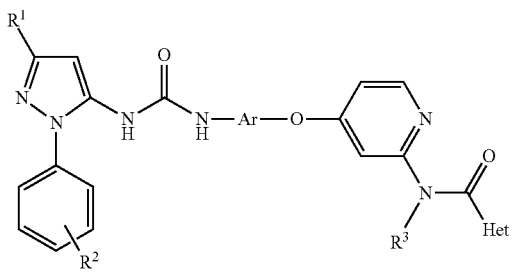

(IN)

wherein $R^1$, $R^2$, Ar and $R^3$ are as defined above and Het represents a $C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from the relevant substituents listed above for compounds of formula (I) for example halogen, $C_{1-6}$ alkyl, $C_{1-6}$ alkoxy, $C_{1-6}$ haloalkyl, amino, $C_{1-4}$ mono and di-alkyl amino.

In one embodiment of compounds of formula (IM) Het is morpholinyl or tetrahydropyranyl.

In one embodiment the compound is not: N-(4-((4-(3-(3-tert-Butyl-1-p-tolyl-1H-pyrazol-5-yl)ureido)naphthalen-1-yloxy)methyl)pyridin-2-yl)-2-methoxyacetamide.

In one embodiment the compound is not: N-(4-((4-(3-(3-tert-Butyl-1-p-tolyl-1H-pyrazol-5-yl)ureido)naphthalen-1-yloxy)) pyridin-2-yl)-2-methoxyacetamide.

In one embodiment the compound is: N-(4-((4-(3-(3-tert-Butyl-1-p-tolyl-1H-pyrazol-5-yl)ureido)naphthalen-1-yloxy)methyl)pyridin-2-yl)-2-methoxyacetamide.

In one embodiment the compound is: N-(4-((4-(3-(3-tert-Butyl-1-p-tolyl-1H-pyrazol-5-yl)ureido)naphthalen-1-yloxy)) pyridin-2-yl)-2-methoxyacetamide.

In one embodiment the compound is:

Methyl 4-((4-(3-(3-tert-butyl-1-p-tolyl-1H-pyrazol-5-yl)ureido)naphthalen-1-yloxy)methyl)pyridin-2-ylurea;

N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide;

(S)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;

(R)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;

N-(4-((4-(3-(3-tert-Butyl-1-p-tolyl-1H-pyrazol-5-yl)ureido)naphthalen-1-yloxy)methyl)pyridin-2-yl)-2-(methylthio)acetamide;

N-(4-((4-(3-(3-tert-Butyl-1-p-tolyl-1H-pyrazol-5-yl)ureido)naphthalen-1-yloxy)methyl)pyridin-2-yl)-2-morpholinoacetamide;

N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide;

N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide;

N-(4-((4-(3-(3-tert-Butyl-1-p-tolyl-1H-pyrazol-5-yl)ureido)naphthalen-1-yloxy)methyl)pyridin-2-yl)-2-(methylamino)acetamide;

N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide;

1-(4-((3-Methylureidopyridin-4-yl)methoxy)naphthalen-1-yl)-3-(3-tert-butyl-1-p-tolyl-1H-pyrazol-5-yl)urea;

N-(4-((4-(3-(3-tert-Butyl-1-p-tolyl-1H-pyrazol-5-yl)ureido)naphthalen-1-yloxy)methyl)pyridin-3-yl)-2-methoxyacetamide;

N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide;

N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide;

4-(2-(4-(3-(3-tert-Butyl-1-p-tolyl-1H-pyrazol-5-yl)ureido)naphthalen-1-yloxy)ethyl)-1-methyl-3-(pyridin-2-yl)urea;

4-(2-(4-(3-(3-tert-Butyl-1-p-tolyl-1H-pyrazol-5-yl)ureido)naphthalen-1-yloxy)ethyl)-3-(pyridin-2-yl)urea;

N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide;

N-(4-((4-(3-(3-tert-Butyl-1-p-tolyl-1H-pyrazol-5-yl)ureido)naphthalen-1-yloxy)methyl)pyrimidin-2-yl)-2-methoxyacetamide;

N-(1-(2-(4-(3-(3-tert-butyl-1-p-tolyl-1H-pyrazol-5-yl)ureido)naphthalen-1-yloxy)ethyl)-1H-imidazol-4-yl)-2-methoxyacetamide;

N-(4-((4-(3-(3-tert-Butyl-1-p-tolyl-1H-pyrazol-5-yl)ureido)naphthalen-1-yloxy)methyl)pyridin-2-yl)-2-(methylsulfonyl)acetamide;

N-(4-((4-(3-(3-tert-Butyl-1-p-tolyl-1H-pyrazol-5-yl)ureido)naphthalen-1-yloxy)methyl)pyridin-2-yl)-2-hydroxyacetamide;

N-(4-((4-(3-(3-tert-Butyl-1-p-tolyl-1H-pyrazol-5-yl)ureido)naphthalen-1-yloxy)methyl)pyridin-2-yl)-2-methyl-2-(methylamino)propanamide;

(S)—N-(4-((4-(3-(3-tert-Butyl-1-p-tolyl-1H-pyrazol-5-yl)ureido)naphthalen-1-yloxy)methyl)pyridin-2-yl)-2-(methylamino)propanamide;

(R)—N-(4-((4-(3-(3-tert-Butyl-1-p-tolyl-1H-pyrazol-5-yl)ureido)naphthalen-1-yloxy)methyl)pyridin-2-yl)morpholine-3-carboxamide;

(S)—N-(4-((4-(3-(3-tert-Butyl-1-p-tolyl-1H-pyrazol-5-yl)ureido)naphthalen-1-yloxy)methyl)pyridin-2-yl)morpholine-3-carboxamide;

N-(4-((4-(3-(3-tert-Butyl-1-p-tolyl-1H-pyrazol-5-yl)ureido)naphthalen-1-yloxy)methyl)pyridin-2-yl)-4-methylpiperazine-1-carboxamide;

N-(4-((4-(3-(3-tert-Butyl-1-p-tolyl-1H-pyrazol-5-yl)ureido)naphthalen-1-yloxy)methyl)pyridin-2-yl)morpholine-4-carboxamide;

N-(4-((4-(3-(3-tert-Butyl-1-p-tolyl-1H-pyrazol-5-yl)ureido)naphthalen-1-yloxy)methyl)pyridin-2-yl)-3-methoxypropanamide;

2-(3-(4-((4-(3-(3-tert-Butyl-1-p-tolyl-1H-pyrazol-5-yl)ureido)naphthalen-1-yloxy)methyl)pyridin-2-yl)ureido)-N-(2-methoxyethyl)acetamide;

N-(4-((4-(3-(3-tert-Butyl-1-p-tolyl-1H-pyrazol-5-yl)ureido)naphthalen-1-yloxy)methyl)pyridin-2-yl)-4-(dimethylamino)butanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)propanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)-2-oxoimidazolidine-1-carboxamide;

N-(4-((4-(3-(3-tert-Butyl-1-p-tolyl-1H-pyrazol-5-yl)ureido)naphthalen-1-yloxy)methyl)pyridin-2-yl)-2-(methylsulfinyl)acetamide;

N-(4-((4-(3-(3-tert-Butyl-1-p-tolyl-1H-pyrazol-5-yl)ureido)naphthalen-1-yloxy)methyl)pyridin-2-yl)-2-(2-methoxyethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-(2-methoxyethoxy)ethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylsulfonyl)acetamide;

2-(Bis(2-methoxyethyl)amino)-N-(4-((4-(3-(3-tert-butyl-1-p-tolyl-1H-pyrazol-5-yl)ureido) naphthalen-1-yloxy)methyl)pyridin-2-yl)acetamide;

N-(4-(2-(4-(3-(3-tert-Butyl-1-p-tolyl-1H-pyrazol-5-yl)ureido)naphthalen-1-yloxy)ethyl)pyridin-3-yl)-2-methoxyacetamide;

N-(4-(2-(4-(3-(3-tert-butyl-1-p-tolyl-1H-pyrazol-5-yl)ureido)naphthalen-1-yl)ethoxy)pyridin-2-yl)-2-methoxyacetamide;

N-(4-(1-(4-(3-(3-tert-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)-2-methylpropyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)propyl)pyridin-2-yl)-2-methoxyacetamide;

N-(4-(1-(4-(3-(3-tert-Butyl-1-p-tolyl-1H-pyrazol-5-yl)ureido)naphthalen-1-yloxy)propan-2-yl)pyridin-2-yl)-2-methoxyacetamide;

N-(4-(1-(4-(3-(3-tert-Butyl-1-p-tolyl-1-pyrazol-5-yl)ureido)naphthalen-1-yloxy)-2-methyl propan-2-yl)pyridin-2-yl)-2-methoxyacetamide;

N-(4-((4-(3-(3-tert-Butyl-1-(4-(hydroxymethyl)phenyl)-1H-pyrazol-5-yl)ureido)naphthalen-1-yloxy)methyl)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-(methylsulfonyl)acetamide, N-(4-(4-(3-(3-tert-Butyl-1-p-tolyl-1H-pyrazol-5-yl)ureido)naphthalen-1-yloxy)pyridin-2-yl)-2-(2-methoxyethoxy)acetamide;

N-(4-(4-(3-(3-tert-Butyl-1-p-tolyl-1H-pyrazol-5-yl)ureido)naphthalen-1-yloxy)pyridin-2-yl)tetrahydro-2H-pyran-4-carboxamide;

N-(4-(4-(3-(3-tert-Butyl-1-p-tolyl-1H-pyrazol-5-yl)ureido)naphthalen-1-yloxy)pyridin-2-yl)-2-(methylthio)acetamide;

N-(4-(4-(3-(3-tert-Butyl-1-p-tolyl-1H-pyrazol-5-yl)ureido)naphthalen-1-yloxy)pyridin-2-yl)-3-methoxypropanamide;

N-(4-(4-(3-(3-tert-Butyl-1-p-tolyl-1H-pyrazol-5-yl)ureido)naphthalen-1-yloxy)pyridin-2-yl)-2-hydroxyacetamide;

N-(4-(4-(3-(3-Isopropyl-1-p-tolyl-1H-pyrazol-5-yl)ureido)naphthalen-1-yloxy)pyridin-2-yl)-2-methoxyacetamide;

N-(4-(4-(3-(3-Ethyl-1-p-tolyl-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-methoxyacetamide;

N-(4-(4-(3-(3-(1-Hydroxy-2-methylpropan-2-yl)-1-p-tolyl-1H-pyrazol-5-yl)ureido)naphthalen-1-yloxy)pyridin-2-yl)-2-methoxyacetamide;

N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-morpholinoacetamide;

N-(4-(4-(3-(3-tert-Butyl-1-p-tolyl-1H-pyrazol-5-yl)ureido)naphthalen-1-yloxy)pyridin-2-yl)-(dimethylamino)acetamide;

N-(4-(4-(3-(3-tert-Butyl-1-p-tolyl-1H-pyrazol-5-yl)ureido)naphthalen-1-yloxy)pyridin-2-yl)-2-(2-methoxyethylamino)acetamide;

N-(4-(4-(3-(3-tert-Butyl-1-p-tolyl-1H-pyrazol-5-yl)ureido)naphthalen-1-yloxy)pyridin-2-yl)-2-ureidoacetamide;

N-(4-(4-(3-(3-tert-Butyl-1-p-tolyl-1H-pyrazol-5-yl)ureido)naphthalen-1-yloxy)pyridin-2-yl)-2-(2-methoxyacetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)tetrahydro-2H-pyran-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)isonicotinamide;

N-(4-(4-(3-(3-tert-Butyl-1-p-tolyl-1H-pyrazol-5-yl)ureido)naphthalen-1-yloxy)pyridin-2-yl)-2-(2-(methylsulfonyl)acetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)morpholine-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide;

N-(4-(4-(3-(3-tert-Butyl-1-p-tolyl-1H-pyrazol-5-yl)ureido)phenoxy)pyridin-2-yl)-2-methoxyacetamide;

N-(4-(4-(3-(3-tert-Butyl-1-p-tolyl-1H-pyrazol-5-yl)ureido)-2-methylphenoxy)pyridin-2-yl)-2-methoxyacetamide;

N-(4-(4-(3-(3-tert-Butyl-1-p-tolyl-1H-pyrazol-5-yl)ureido)-3-methylphenoxy)pyridin-2-yl)-2-methoxyacetamide;

N-(4-(4-(3-(3-tert-Butyl-1-p-tolyl-1H-pyrazol-5-yl)ureido)-2-methoxyphenoxy)pyridin-2-yl)-2-methoxyacetamide;

N-(4-(4-(3-(3-tert-Butyl-1-p-tolyl-1H-pyrazol-5-yl)ureido)-2,3-dimethylphenoxy)pyridin-2-yl)-2-methoxyacetamide;

N-(4-(4-(3-(3-tert-Butyl-1-p-tolyl-1H-pyrazol-5-yl)ureido)-3-methoxyphenoxy)pyridin-2-yl)-2-methoxyacetamide;

N-Ethyl-N'-4-(4-(3-(3-tert-butyl-1-p-tolyl-1H-pyrazol-5-yl)ureido) naphthalen-1-yloxy)pyridin-2-ylurea;

4-(4-(3-(3-tert-Butyl-1-p-tolyl-1H-pyrazol-5-yl)ureido) naphthalen-1-yloxy)pyridin-2-ylurea;

N-Propan-2-yl-N'-4-(4-(3-(3-tert-butyl-1-p-tolyl-1H-pyrazol-5-yl)ureido)naphthalen-1-yloxy)pyridin-2-ylurea;

1-(3-(tert-Butyl)-1-(p-tolyl)-1H-pyrazol-5-yl)-3-(4-((2-(3-phenylureido)pyridin-4-yl)oxy)naphthalen-1-yl)urea;

1-(4-((2-(3-Benzylureido)pyridin-4-yl)oxy)naphthalen-1-yl)-3-(3-(tert-butyl)-1-(p-tolyl)-1H-pyrazol-5-yl)urea;

1-(4-((2-(3-Cyclopropylureido)pyridin-4-yl)oxy)naphthalen-1-yl)-3-(3-(tert-butyl)-1-(p-tolyl)-1H-pyrazol-5-yl) urea;

1-(3-(tert-Butyl)-1-(p-tolyl)-1H-pyrazol-5-yl)-3-(4-((2-(3-(2-methoxyethyl)ureido)pyridin-4-yl)oxy)naphthalen-1-yl)urea;

1-(3-(tert-Butyl)-1-(p-tolyl)-1H-pyrazol-5-yl)-3-(4-((2-(3-cyclopentyl)ureido)pyridin-4-yl)oxy)naphthalen-1-yl) urea;

1-(3-(tert-Butyl)-1-(p-tolyl)-1H-pyrazol-5-yl)-3-(4-((2-(3-methyl)ureido)pyridin-4-yl)oxy)naphthalen-1-yl)urea;

Ethyl 2-(3-(4-((4-(3-(3-(tert-butyl)-1-(p-tolyl)-1H-pyrazol-5-yl)ureido)naphthalen-1-yl)oxy)pyridin-2-yl)ureido)acetate;

4-(3-(4-(4-(3-(3-tert-Butyl-1-p-tolyl-1H-pyrazol-5-yl)ureido)naphthalen-1-yloxy)pyridin-2-yl)ureido)piperidine;

N-Acetyl 4-(3-(4-(4-(3-(3-tert-butyl-1-p-tolyl-1H-pyrazol-5-yl)ureido) naphthalen-1-yloxy)pyridin-2-yl)ureido)piperidine;

2-(2-Methoxyethoxy)-1-(4-(3-(4-(4-(3-(3-tert-butyl-1-p-tolyl-1H-pyrazol-5-yl)ureido)naphthalen-1-yloxy)pyridin-2-yl)ureido)piperidin-1-yl)ethanone;

N-Methylsulfonyl-4-(3-(4-(4-(3-(3-tert-butyl-1-p-tolyl-1H-pyrazol-5-yl)ureido)naphthalen-1-yloxy)pyridin-2-yl)ureido)piperidine;

N-(4-(4-(3-(3-tert-Butyl-1-p-tolyl-1H-pyrazol-5-yl)ureido)naphthalen-1-yloxy)pyridin-2-yl)morpholine-4-carboxamide;

N-(4-((4-(3-(3-(tert-butyl)-1-(p-tolyl)-1H-pyrazol-5-yl)ureido)naphthalen-1-yl)oxy)pyridin-2-yl)-4-methylpiperazine-1-carboxamide;

3-(4-((4-(3-(3-(tert-butyl)-1-(p-tolyl)-1H-pyrazol-5-yl)ureido)naphthalen-1-yl)oxy)pyridin-2-yl)-1,1-dimethylurea;

N-(4-((4-(3-(3-(tert-Butyl)-1-(p-tolyl)-1H-pyrazol-5-yl)ureido)naphthalen-1-yl)oxy)pyridin-2-yl)piperidine-1-carboxamide;

N-Methyl-N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;

N-(4-(morpholin-4-yl)butyl)-N'-4-(4-(3-(3-tert-butyl-1-p-tolyl-1H-pyrazol-5-yl)ureido)naphthalen-1-yloxy)pyridin-2-ylurea;

N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;

N-(3-methylisoxazol-5-yl)methyl-N'-4-(4-(3-(3-tert-butyl-1-p-tolyl-1H-pyrazol-5-yl)ureido)naphthalen-1-yloxy)pyridin-2-ylurea;

N-(1-methyl)piperidin-4-yl-N'-4-(4-(3-(3-tert-butyl-1-p-tolyl-1H-pyrazol-5-yl)ureido)naphthalen-1-yloxy)pyridin-2-ylurea;

N-(4-(4-(3-(3-tert-Butyl-1-p-tolyl-1H-pyrazol-5-yl)ureido)naphthalen-1-yloxy)pyridin-2-yl)-4-hydroxypiperidine-1-carboxamide;

N-(3-(imidazol-1-yl)propyl)-N'-4-(4-(3-(3-tert-butyl-1-p-tolyl-1H-pyrazol-5-yl)ureido)naphthalen-1-yloxy)pyridin-2-ylurea;

N-(2-(3-(4-(4-(3-(3-tert-Butyl-1-p-tolyl-1H-pyrazol-5-yl)ureido)naphthalen-1-yloxy)pyridin-2-yl)ureido)acetyl)pyrrolidine;

(R)—N-(4-(4-(3-(3-tert-Butyl-1-p-tolyl-1H-pyrazol-5-yl)ureido)naphthalen-1-yloxy)pyridin-2-yl)-3-(dimethylamino)pyrrolidine-1-carboxamide;

N-(4-(4-(3-(3-tert-Butyl-1-p-tolyl-1H-pyrazol-5-yl)ureido)naphthalen-1-yloxy)pyridin-2-yl)pyrrolidine-1-carboxamide;

2-(3-(4-(4-(3-(3-tert-Butyl-1-p-tolyl-1H-pyrazol-5-yl)ureido)naphthalen-1-yloxy)pyridin-2-yl)ureido)-N-methylacetamide;

2-(3-(4-(4-(3-(3-tert-Butyl-1-p-tolyl-1H-pyrazol-5-yl)ureido)naphthalen-1-yloxy)pyridin-2-yl)ureido)-N-(2-morpholinoethyl)acetamide;

2-(3-(4-(4-(3-(3-tert-Butyl-1-p-tolyl-1H-pyrazol-5-yl)ureido)naphthalen-1-yloxy)pyridin-2-yl)ureido)acetyl morpholine;

2-(3-(4-(4-(3-(3-tert-Butyl-1-p-tolyl-1H-pyrazol-5-yl)ureido)naphthalen-1-yloxy)pyridin-2-yl)ureido)-N-(2-(pyridin-4-yl)ethyl)acetamide;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;

1-(2-(3-(4-(4-(3-(3-tert-Butyl-1-p-tolyl-1H-pyrazol-5-yl)ureido)naphthalen-1-yloxy)pyridin-2-yl)ureido)acetyl)-4-methylpiperazine;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;

N-(6-(4-(3-(3-tert-Butyl-1-p-tolyl-1H-pyrazol-5-yl)ureido)naphthalen-1-yloxy)pyrimidin-4-yl)-2-methoxyacetamide;

N-(6-(4-(3-(3-tert-Butyl-1-p-tolyl-1H-pyrazol-5-yl)ureido)phenoxy)pyrimidin-4-yl)-2-methoxyacetamide;

N-(4-(4-(3-(3-tert-Butyl-1-p-tolyl-1H-pyrazol-5-yl)ureido)naphthalen-1-yloxy)pyrimidin-2-yl)-2-methoxyacetamide;

3-(4-(4-(3-(3-tert-Butyl-1-p-tolyl-1H-pyrazol-5-yl)ureido)naphthalen-1-yloxy)pyrimidin-2-yl)urea;

1-Methyl-3-(4-(4-(3-(3-tert-butyl-1-p-tolyl-1H-pyrazol-5-yl)ureido)naphthalen-1-yloxy)pyrimidin-2-yl)urea;

1,1-Dimethyl-3-(4-(4-(3-(3-tert-butyl-1-p-tolyl-1H-pyrazol-5-yl)ureido)naphthalen-1-yloxy)pyrimidin-2-yl)urea;

1-Cyclopropyl-3-(4-(4-(3-(3-tert-butyl-1-p-tolyl-1H-pyrazol-5-yl)ureido)naphthalen-1-yloxy)pyrimidin-2-yl)urea;

(4-(4-(3-(3-tert-butyl-1-p-tolyl-1H-pyrazol-5-yl)ureido)naphthalen-1-yloxy)pyrimidin-2-yl) morpholine-4-carboxamide;

3-(6-(4-(3-(3-tert-Butyl-1-p-tolyl-1H-pyrazol-5-yl)ureido)naphthalen-1-yloxy)pyrimidin-4-yl)urea;

2-(3-(4-(4-(3-(3-tert-Butyl-1-p-tolyl-1H-pyrazol-5-yl)ureido)naphthalen-1-yloxy)pyridin-2-yl)ureido)acetic acid or a pharmaceutically acceptable salt thereof, including all stereoisomers, tautomers and isotopic derivatives thereof.

In one embodiment the compound according to the disclosure is:

N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide;

(S)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;

(R)—N-(4-((4-(3-(3-tert-Butyl-1-p-tolyl-1H-pyrazol-5-yl)ureido)naphthalen-1-yloxy)methyl)pyridin-2-yl)-2-methoxypropanamide;

N-(4-((4-(3-(3-tert-Butyl-1-p-tolyl-1H-pyrazol-5-yl)ureido)naphthalen-1-yloxy)methyl)pyridin-2-yl)-2-(methylsulfonyl)acetamide N-(4-((4-(3-(3-tert-Butyl-1-p-tolyl-1H-pyrazol-5-yl)ureido)naphthalen-1-yloxy)methyl)pyridin-2-yl)-2-hydroxyacetamide;

N-(4-((4-(3-(3-tert-Butyl-1-p-tolyl-1H-pyrazol-5-yl)ureido)naphthalen-1-yloxy)methyl)pyridin-2-yl)-2-methyl-2-(methylamino)propanamide;

(S)—N-(4-((4-(3-(3-tert-Butyl-1-p-tolyl-1H-pyrazol-5-yl)ureido)naphthalen-1-yloxy)methyl)pyridin-2-yl)-2-(methylamino)propanamide;

(R)—N-(4-((4-(3-(3-tert-Butyl-1-p-tolyl-1H-pyrazol-5-yl)ureido)naphthalen-1-yloxy)methyl)pyridin-2-yl)morpholine-3-carboxamide;

(S)—N-(4-((4-(3-(3-tert-Butyl-1-p-tolyl-1H-pyrazol-5-yl)ureido)naphthalen-1-yloxy)methyl)pyridin-2-yl)morpholine-3-carboxamide;

N-(4-((4-(3-(3-tert-Butyl-1-p-tolyl-1H-pyrazol-5-yl)ureido)naphthalen-1-yloxy)methyl)pyridin-2-yl)-4-methylpiperazine-1-carboxamide;

N-(4-((4-(3-(3-tert-Butyl-1-p-tolyl-1H-pyrazol-5-yl)ureido)naphthalen-1-yloxy)methyl)pyridin-2-yl)morpholine-4-carboxamide;

N-(4-((4-(3-(3-tert-Butyl-1-p-tolyl-1H-pyrazol-5-yl)ureido)naphthalen-1-yloxy)methyl)pyridin-2-yl)-3-methoxypropanamide;

2-(3-(4-((4-(3-(3-tert-Butyl-1-p-tolyl-1H-pyrazol-5-yl)ureido)naphthalen-1-yloxy)methyl)pyridin-2-yl)ureido)-N-(2-methoxyethyl)acetamide;

N-(4-((4-(3-(3-tert-Butyl-1-p-tolyl-1H-pyrazol-5-yl)ureido)naphthalen-1-yloxy)methyl)pyridin-2-yl)-4-(dimethylamino)butanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)propanamide;

N-(4-((4-(3-(3-tert-Butyl-1-p-tolyl-1H-pyrazol-5-yl)ureido) naphthalen-1-yloxy)methyl)pyridin-2-yl)-3-(methylsulfonyl)-2-oxoimidazolidine-1-carboxamide;

N-(4-((4-(3-(3-tert-Butyl-1-p-tolyl-1H-pyrazol-5-yl)ureido) naphthalen-1-yloxy)methyl)pyridin-2-yl)-2-(methylthio) acetamide;

N-(4-((4-(3-(3-tert-Butyl-1-p-tolyl-1H-pyrazol-5-yl)ureido) naphthalen-1-yloxy)methyl)pyridin-2-yl)-2-(methylsulfinyl)acetamide;

N-(4-((4-(3-(3-tert-Butyl-1-p-tolyl-1H-pyrazol-5-yl)ureido) naphthalen-1-yloxy)methyl)pyridin-2-yl)-2-morpholinoacetamide;

N-(4-((4-(3-(3-tert-Butyl-1-p-tolyl-1H-pyrazol-5-yl)ureido) naphthalen-1-yloxy)methyl)pyridin-2-yl)-2-(pyrrolidin-1-yl)acetamide;

N-(4-((4-(3-(3-tert-Butyl-1-p-tolyl-1H-pyrazol-5-yl)ureido) naphthalen-1-yloxy)methyl)pyridin-2-yl)-2-(4-methylpiperazin-1-yl)acetamide;

N-(4-((4-(3-(3-tert-Butyl-1-p-tolyl-1H-pyrazol-5-yl)ureido) naphthalen-1-yloxy)methyl)pyridin-2-yl)-2-(4-(2-methoxyethyl)piperazin-1-yl)acetamide;

N-(4-((4-(3-(3-tert-Butyl-1-p-tolyl-1H-pyrazol-5-yl)ureido) naphthalen-1-yloxy)methyl)pyridin-2-yl)-2-(2-methoxyethylamino)acetamide;

N-(4-((4-(3-(3-tert-Butyl-1-p-tolyl-1H-pyrazol-5-yl)ureido) naphthalen-1-yloxy)methyl)pyridin-2-yl)-2-(dimethylamino)acetamide;

N-(4-((4-(3-(3-tert-Butyl-1-p-tolyl-1H-pyrazol-5-yl)ureido) naphthalen-1-yloxy)methyl)pyridin-2-yl)-2-(methylamino)acetamide;

N-(4-((4-(3-(3-tert-Butyl-1-p-tolyl-1H-pyrazol-5-yl)ureido) naphthalen-1-yloxy)methyl)pyridin-2-yl)-2-((4-methoxybenzyl)(methyl)amino)acetamide;

N-(4-((4-(3-(3-tert-Butyl-1-p-tolyl-1H-pyrazol-5-yl)ureido) naphthalen-1-yloxy)methyl)pyridin-2-yl)-2-(2-methoxyethylthio)acetamide;

N-(4-((4-(3-(3-tert-Butyl-1-p-tolyl-1H-pyrazol-5-yl)ureido) naphthalen-1-yloxy)methyl)pyridin-2-yl)-2-(2-(2-methoxyethoxy)ethylthio)acetamide;

N-(4-((4-(3-(3-tert-Butyl-1-p-tolyl-1H-pyrazol-5-yl)ureido) naphthalen-1-yloxy)methyl)pyridin-2-yl)-2-(2-morpholinoethylthio)acetamide;

N-(4-((4-(3-(3-tert-Butyl-1-p-tolyl-1H-pyrazol-5-yl)ureido) naphthalen-1-yloxy)methyl)pyridin-2-yl)-2-(2-morpholinoethylsulfonyl)acetamide;

2-(Bis(2-methoxyethyl)amino)-N-(4-((4-(3-(3-tert-butyl-1-p-tolyl-1H-pyrazol-5-yl)ureido) naphthalen-1-yloxy)methyl)pyridin-2-yl)acetamide;

1-(4-((3-Methylureidopyridin-4-yl)methoxy)naphthalen-1-yl)-3-(3-tert-butyl-1-p-tolyl-1H-pyrazol-5-yl)urea;

N-(4-((4-(3-(3-tert-Butyl-1-p-tolyl-1H-pyrazol-5-yl)ureido) naphthalen-1-yloxy)methyl)pyridin-3-yl)-2-methoxyacetamide;

N-(4-((4-(3-(3-tert-Butyl-1-p-tolyl-1H-pyrazol-5-yl)ureido) naphthalen-1-yloxy)methyl)pyridin-3-yl)-2-(2-methoxyethoxy)acetamide;

N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide;

4-(2-(4-(3-(3-tert-Butyl-1-p-tolyl-1H-pyrazol-5-yl)ureido) naphthalen-1-yloxy)ethyl)-1-methyl-3-(pyridin-2-yl)urea;

4-(2-(4-(3-(3-tert-Butyl-1-p-tolyl-1H-pyrazol-5-yl)ureido) naphthalen-1-yloxy)ethyl)-3-(pyridin-2-yl)urea;

N-(4-(2-(4-(3-(3-tert-Butyl-1-p-tolyl-1H-pyrazol-5-yl)ureido)naphthalen-1-yloxy)ethyl)pyridin-3-yl)-2-methoxyacetamide;

N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide;

N-(4-(2-(4-(3-(3-tert-butyl-1-p-tolyl-1H-pyrazol-5-yl)ureido)naphthalen-1-yl)ethoxy)pyridin-2-yl)-2-methoxyacetamide;

N-(4-(1-(4-(3-(3-tert-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)-2-methyl propyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)propyl)pyridin-2-yl)-2-methoxyacetamide;

N-(4-(1-(4-(3-(3-tert-Butyl-1-p-tolyl-1H-pyrazol-5-yl)ureido)naphthalen-1-yloxy)propan-2-yl)pyridin-2-yl)-2-methoxyacetamide;

N-(4-(1-(4-(3-(3-tert-Butyl-1-p-tolyl-1-pyrazol-5-yl)ureido) naphthalen-1-yloxy)-2-methyl propan-2-yl)pyridin-2-yl)-2-methoxyacetamide;

N-(4-((4-(3-(3-tert-Butyl-1-(4-(hydroxymethyl)phenyl)-1H-pyrazol-5-yl)ureido)naphthalen-1-yloxy)methyl)pyridin-2-yl)-2-methoxyacetamide;

N-(4-((4-(3-(3-tert-Butyl-1-p-tolyl-1H-pyrazol-5-yl)ureido) naphthalen-1-yloxy)methyl)pyrimidin-2-yl)-2-methoxyacetamide;

N-(4-(4-(3-(3-tert-Butyl-1-p-tolyl-1H-pyrazol-5-yl)ureido) naphthalen-1-yloxy)pyridin-2-yl)-2-(methylsulfonyl)acetamide;

N-(4-(4-(3-(3-tert-Butyl-1-p-tolyl-1H-pyrazol-5-yl)ureido) naphthalen-1-yloxy)pyridin-2-yl)-2-methoxyacetamide;

N-(4-(4-(3-(3-tert-Butyl-1-p-tolyl-1H-pyrazol-5-yl)ureido) naphthalen-1-yloxy)pyridin-2-yl)-2-(2-methoxyethoxy) acetamide;

N-(4-(4-(3-(3-tert-Butyl-1-p-tolyl-1H-pyrazol-5-yl)ureido) naphthalen-1-yloxy)pyridin-2-yl)tetrahydro-2H-pyran-4-carboxamide;

N-(4-(4-(3-(3-tert-Butyl-1-p-tolyl-1H-pyrazol-5-yl)ureido) naphthalen-1-yloxy)pyridin-2-yl)-2-(methylthio)acetamide;

N-(4-(4-(3-(3-tert-Butyl-1-p-tolyl-1H-pyrazol-5-yl)ureido) naphthalen-1-yloxy)pyridin-2-yl)-3-methoxypropanamide;

N-(4-(4-(3-(3-tert-Butyl-1-p-tolyl-1H-pyrazol-5-yl)ureido) naphthalen-1-yloxy)pyridin-2-yl)-2-hydroxyacetamide;

N-(4-(4-(3-Isopropyl-1-p-tolyl-1H-pyrazol-5-yl)ureido) naphthalen-1-yloxy)pyridin-2-yl)-2-methoxyacetamide;

N-(4-(4-(3-(3-Ethyl-1-p-tolyl-1H-pyrazol-5-yl)ureido) naphthalen-1-yloxy)pyridin-2-yl)-2-methoxyacetamide;

N-(4-(4-(3-(3-tert-Butyl-1-p-tolyl-1H-pyrazol-5-yl)ureido) naphthalen-1-yloxy)pyridin-2-yl)-2-methoxyacetamide;

N-(4-(4-(3-(3-(1-Hydroxy-2-methylpropan-2-yl)-1-p-tolyl-1H-pyrazol-5-yl)ureido)naphthalen-1-yloxy)pyridin-2-yl)-2-methoxyacetamide;

N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido) naphthalen-1-yloxy)pyridin-2-yl)-2-morpholinoacetamide;

N-(4-(4-(3-(3-tert-Butyl-1-p-tolyl-1H-pyrazol-5-yl)ureido) naphthalen-1-yloxy)pyridin-2-yl)-(dimethylamino)acetamide;

N-(4-(4-(3-(3-tert-Butyl-1-p-tolyl-1H-pyrazol-5-yl)ureido) naphthalen-1-yloxy)pyridin-2-yl)-2-(2-methoxyethylamino)acetamide;

N-(4-(4-(3-(3-tert-Butyl-1-p-tolyl-1H-pyrazol-5-yl)ureido) naphthalen-1-yloxy)pyridin-2-yl)-2-ureidoacetamide;

N-(4-(4-(3-(3-tert-Butyl-1-p-tolyl-1H-pyrazol-5-yl)ureido) naphthalen-1-yloxy)pyridin-2-yl)-2-(2-methoxyacetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl) tetrahydro-2H-pyran-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl) isonicotinamide;

N-(4-(4-(3-(3-tert-Butyl-1-p-tolyl-1H-pyrazol-5-yl)ureido) naphthalen-1-yloxy)pyridin-2-yl)-2-(2-(methylsulfonyl) acetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl) morpholine-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide;

N-(4-(4-(3-(3-tert-Butyl-1-p-tolyl-1H-pyrazol-5-yl)ureido) phenoxy)pyridin-2-yl)-2-methoxy acetamide;

N-(4-(4-(3-(3-tert-Butyl-1-p-tolyl-1H-pyrazol-5-yl)ureido)-2-methylphenoxy)pyridin-2-yl)-2-methoxyacetamide;

N-(4-(4-(3-(3-tert-Butyl-1-p-tolyl-1H-pyrazol-5-yl)ureido)-3-methylphenoxy)pyridin-2-yl)-2-methoxyacetamide;

N-(4-(4-(3-(3-tert-Butyl-1-p-tolyl-1H-pyrazol-5-yl)ureido)-2-methoxyphenoxy)pyridin-2-yl)-2-methoxyacetamide;

N-(4-(4-(3-(3-tert-Butyl-1-p-tolyl-1H-pyrazol-5-yl)ureido)-2,3-dimethylphenoxy)pyridin-2-yl)-2-methoxyacetamide;

N-(4-(4-(3-(3-tert-Butyl-1-p-tolyl-1H-pyrazol-5-yl)ureido)-3-methoxyphenoxy)pyridin-2-yl)-2-methoxyacetamide;

N-Ethyl-N'-4-(4-(3-(3-tert-butyl-1-p-tolyl-1H-pyrazol-5-yl) ureido)naphthalen-1-yloxy)pyridin-2-ylurea;

4-(4-(3-(3-tert-Butyl-1-p-tolyl-1H-pyrazol-5-yl)ureido) naphthalen-1-yloxy)pyridin-2-ylurea;

N-Propan-2-yl-N'-4-(4-(3-(3-tert-butyl-1-p-tolyl-1H-pyrazol-5-yl)ureido)naphthalen-1-yloxy)pyridin-2-ylurea;

1-(3-tert-Butyl-1-p-tolyl-1H-pyrazol-5-yl)-3-(4-((2-(3-phenylureido)pyridin-4-yl)oxy) naphthalen-1-yl)urea;

1-(4-((2-(3-Benzylureido)pyridin-4-yl)oxy)naphthalen-1-yl)-3-(3-(tert-butyl)-1-(p-tolyl)-1H-pyrazol-5-yl)urea;

1-(4-((2-(3-Cyclopropylureido)pyridin-4-yl)oxy)naphthalen-1-yl)-3-(3-tert-butyl-1-p-tolyl-1H-pyrazol-5-yl)urea;

1-(3-tert-Butyl-1-p-tolyl-1H-pyrazol-5-yl)-3-(4-((2-(3-(2-methoxyethyl)ureido)pyridin-4-yl)oxy) naphthalen-1-yl) urea;

1-(3-tert-Butyl-1-p-tolyl-1H-pyrazol-5-yl)-3-(4-((2-(3-cyclopentyl)ureido)pyridin-4-yl)oxy) naphthalen-1-yl)urea;

1-(3-tert-Butyl-1-p-tolyl-1H-pyrazol-5-yl)-3-(4-((2-(3-methyl)ureido)pyridin-4-yl)oxy) naphthalen-1-yl)urea;

Ethyl 2-(3-(4-((4-(3-(3-tert-butyl-1-p-tolyl-1H-pyrazol-5-yl) ureido)naphthalen-1-yl)oxy)pyridin-2-yl)ureido)acetate;

4-(3-(4-(4-(3-(3-tert-Butyl-1-p-tolyl-1H-pyrazol-5-yl)ureido)naphthalen-1-yloxy)pyridin-2-yl)ureido)piperidine;

N-Acetyl 4-(3-(4-(4-(3-(3-tert-butyl-1-p-tolyl-1H-pyrazol-5-yl)ureido)naphthalen-1-yloxy)pyridin-2-yl)ureido)piperidine;

2-(2-Methoxyethoxy)-1-(4-(3-(4-(4-(3-(3-tert-butyl-1-p-tolyl-1H-pyrazol-5-yl)ureido) naphthalen-1-yloxy)pyridin-2-yl)ureido)piperidin-1-yl)ethanone;

N-Methylsulfonyl-4-(3-(4-(4-(3-(3-tert-butyl-1-p-tolyl-1H-pyrazol-5-yl)ureido)naphthalen-1-yloxy)pyridin-2-yl) ureido)piperidine;

N-(4-(4-(3-(3-tert-Butyl-1-p-tolyl-1H-pyrazol-5-yl)ureido) naphthalen-1-yloxy)pyridin-2-yl) morpholine-4-carboxamide;

N-(4-((4-(3-(3-tert-Butyl-1-p-tolyl-1H-pyrazol-5-yl)ureido) naphthalen-1-yl)oxy)pyridin-2-yl)-4-methylpiperazine-1-carboxamide;

3-(4-((4-(3-(3-tert-Butyl-1-p-tolyl-1H-pyrazol-5-yl)ureido) naphthalen-1-yl)oxy)pyridin-2-yl)-1,1-dimethylurea;

N-(4-((4-(3-(3-tert-Butyl-1-p-tolyl-1H-pyrazol-5-yl)ureido) naphthalen-1-yl)oxy)pyridin-2-yl)piperidine-1-carboxamide;

N-Methyl-N-(2-(morpholin-4-yl)ethyl)-N'-4-(4-(3-(3-tert-butyl-1-p-tolyl-1H-pyrazol-5-yl)ureido) naphthalen-1-yloxy)pyridin-2-ylurea;

N-(4-(Morpholin-4-yl)butyl)-N'-4-(4-(3-(3-tert-butyl-1-p-tolyl-1H-pyrazol-5-yl)ureido) naphthalen-1-yloxy)pyridin-2-ylurea;

N-(2-(Morpholin-4-yl)ethyl)-N'-4-(4-(3-(3-tert-butyl-1-p-tolyl-1H-pyrazol-5-yl)ureido) naphthalen-1-yloxy)pyridin-2-ylurea;

N-(3-Methylisoxazol-5-yl)methyl-N'-4-(4-(3-(3-tert-butyl-1-p-tolyl-1H-pyrazol-5-yl)ureido) naphthalen-1-yloxy) pyridin-2-ylurea;

N-(1-Methyl)piperidin-4-yl-N'-4-(4-(3-(3-tert-butyl-1-p-tolyl-1H-pyrazol-5-yl)ureido) naphthalen-1-yloxy)pyridin-2-ylurea;

N-(4-(4-(3-(3-tert-Butyl-1-p-tolyl-1H-pyrazol-5-yl)ureido) naphthalen-1-yloxy)pyridin-2-yl)-4-hydroxypiperidine-1-carboxamide;

N-(3-(Imidazol-1-yl)propyl)-N'-4-(4-(3-(3-tert-butyl-1-p-tolyl-1H-pyrazol-5-yl)ureido) naphthalen-1-yloxy)pyridin-2-ylurea;

N-(2-(3-(4-(4-(3-(3-tert-Butyl-1-p-tolyl-1H-pyrazol-5-yl) ureido)naphthalen-1-yloxy)pyridin-2-yl)ureido)acetyl) pyrrolidine;

(R)—N-(4-(4-(3-(3-tert-Butyl-1-p-tolyl-1H-pyrazol-5-yl) ureido)naphthalen-1-yloxy)pyridin-2-yl)-3-(dimethylamino)pyrrolidine-1-carboxamide;

N-(4-(4-(3-(3-tert-Butyl-1-p-tolyl-1H-pyrazol-5-yl)ureido) naphthalen-1-yloxy)pyridin-2-yl)pyrrolidine-1-carboxamide;

2-(3-(4-(4-(3-(3-tert-Butyl-1-p-tolyl-1H-pyrazol-5-yl)ureido)naphthalen-1-yloxy)pyridin-2-yl)ureido)-N-methylacetamide;

2-(3-(4-(4-(3-(3-tert-Butyl-1-p-tolyl-1H-pyrazol-5-yl)ureido)naphthalen-1-yloxy)pyridin-2-yl)ureido)-N-(2-morpholinoethyl)acetamide;

2-(3-(4-(4-(3-(3-tert-Butyl-1-p-tolyl-1H-pyrazol-5-yl)ureido)naphthalen-1-yloxy)pyridin-2-yl)ureido)acetyl morpholine;

2-(3-(4-(4-(3-(3-tert-Butyl-1-p-tolyl-1H-pyrazol-5-yl)ureido)naphthalen-1-yloxy)pyridin-2-yl)ureido)-N-(2-(pyridin-4-yl)ethyl)acetamide;

N-(3-(1H-Imidazol-1-yl)propyl)-2-(3-(4-(4-(3-(3-tert-butyl-1-p-tolyl-1H-pyrazol-5-yl)ureido) naphthalen-1-yloxy) pyridin-2-yl)ureido)acetamide;

1-(2-(3-(4-(4-(3-(3-tert-Butyl-1-p-tolyl-1H-pyrazol-5-yl) ureido)naphthalen-1-yloxy)pyridin-2-yl)ureido)acetyl)-4-methylpiperazine;

N-(3-(1H-Imidazol-1-yl)propyl)-2-(3-(4-(4-(3-(3-tert-butyl-1-p-tolyl-1H-pyrazol-5-yl)ureido) naphthalen-1-yloxy) pyridin-2-yl)ureido)acetamide;

N-(6-(4-(3-(3-tert-Butyl-1-p-tolyl-1H-pyrazol-5-yl)ureido) naphthalen-1-yloxy)pyrimidin-4-yl)-2-methoxyacetamide;

N-(6-(4-(3-(3-tert-Butyl-1-p-tolyl-1H-pyrazol-5-yl)ureido) phenoxy)pyrimidin-4-yl)-2-methoxy acetamide;

N-(4-(4-(3-(3-tert-Butyl-1-p-tolyl-1H-pyrazol-5-yl)ureido) naphthalen-1-yloxy)pyrimidin-2-yl)-2-methoxyacetamide;

3-(4-(4-(3-(3-tert-Butyl-1-p-tolyl-1H-pyrazol-5-yl)ureido) naphthalen-1-yloxy)pyrimidin-2-yl)urea;

1-Methyl-3-(4-(4-(3-(3-tert-butyl-1-p-tolyl-1H-pyrazol-5-yl)ureido)naphthalen-1-yloxy)pyrimidin-2-yl)urea;

1,1-Dimethyl-3-(4-(4-(3-(3-tert-butyl-1-p-tolyl-1H-pyrazol-5-yl)ureido)naphthalen-1-yloxy)pyrimidin-2-yl)urea;

1-Cyclopropyl-3-(4-(4-(3-(3-tert-butyl-1-p-tolyl-1H-pyrazol-5-yl)ureido)naphthalen-1-yloxy)pyrimidin-2-yl)urea;

(4-(4-(3-(3-tert-butyl-1-p-tolyl-1H-pyrazol-5-yl)ureido) naphthalen-1-yloxy)pyrimidin-2-yl) morpholine-4-carboxamide;

3-(6-(4-(3-(3-tert-Butyl-1-p-tolyl-1H-pyrazol-5-yl)ureido) naphthalen-1-yloxy)pyrimidin-4-yl)urea;

2-(3-(4-(4-(3-(3-tert-Butyl-1-p-tolyl-1H-pyrazol-5-yl)ureido)naphthalen-1-yloxy)pyridin-2-yl)ureido)acetic acid.

or a pharmaceutically acceptable salt thereof, including all stereoisomers, tautomers and isotopic derivatives thereof.

Examples of salts of compound (I) include all pharmaceutically acceptable salts, such as, without limitation, acid addition salts of mineral acids such as HCl and HBr salts and addition salts of organic acids such as a methansulfonic acid salt.

The disclosure herein extends to solvates of compounds of formula (I). Examples of solvates include hydrates.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The compounds described herein may include one or more chiral centres, and the disclosure extends to include racemates, both enantiomers (for example each substantially free of the other enantiomer) and all stereoisomers resulting therefrom. In one embodiment one enantiomeric form is present in a substantially purified form that is substantially free of the corresponding entaniomeric form.

The disclosure also extends to all polymorphic forms of the compounds herein defined.

Pharmaceutical compositions comprising the compounds of formula (I) may also be employed in methods according to the present invention.

In one aspect the compounds are useful in treatment, for example COPD, asthma and/or cystic fibrosis.

The compounds developed to date have typically been intended for oral administration. This strategy involves optimizing compounds which achieve their duration of action by an appropriate pharmacokinetic profile. This ensures that there is a sufficient drug concentration established and maintained after and between doses to provide clinical benefit. The inevitable consequence of this approach is that all body tissues, especially liver and gut, are likely to be exposed to therapeutically active concentrations of the drug, whether or not they are adversely affected by the disease being treated.

An alternative strategy is to design treatment approaches in which the drug is dosed directly to the inflamed organ (topical therapy). Although this approach is not suitable for treating all chronic inflammatory diseases, it has been extensively exploited in lung diseases (asthma, COPD, cystic fibrosis), skin diseases (atopic dermatitis and psoriasis), nasal diseases (allergic rhinitis), ocular disease (allergic conjunctivitis), and gastrointestinal diseases (ulcerative colitis).

In topical therapy, efficacy can be achieved either by (i) ensuring that the drug has a sustained duration of action and is retained in the relevant organ to minimize the risks of systemic toxicity or (ii) producing a formulation which generates a "reservoir" of the active drug which is available to sustain the drug's desired effects. Approach (i) is exemplified by the anticholinergic drug tiotropium (Spiriva), which is administered topically to the lung as a treatment for COPD, and which has an exceptionally high affinity for its target receptor resulting in a very slow off rate and a consequent sustained duration of action.

There is provided according to one aspect of the present disclosure use of a compound of formulation as a p38 MAP kinase inhibitor, for example administered topically to the lung.

In one aspect of the disclosure the compounds herein are particularly suitable for topical delivery, such as topical delivery to the lungs, in particular for the treatment of COPD.

Thus in one aspect there is provided use of compounds of formula (I) for the treatment of COPD and/or asthma, in particular COPD or severe asthma, by inhalation i.e. topical administration to the lung or by intranasal treatment. Advantageously, administration to the lung allows the beneficial effects of the compounds to be realised whilst minimising the side-effects, for patients.

In one aspect the compounds have a longer duration of actions than BIRB 796.

In one embodiment the compounds are suitable for sensitizing patients to treatment with a corticosteroid.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 µm. The formulation will typically contain a topically acceptable diluent such as lactose, usually of large particle size e.g. a mass mean diameter (MMAD) of 100 µm or more. Example dry powder delivery systems include SPINHALER®, DISKHALER®, TURBOHALER®, DISKUS® and CLICKHALER®.

In one embodiment the compounds employed in methods according to the present invention or pharmaceutical compositions comprising the same may suitably be adminstered topically to the lungs, nasal passages and/or eyes.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, allergic conjunctivitis, especially asthma, chronic bronchitis and COPD.

Compounds of the disclosure may also re-sensitise the patient's condition to treatment with a corticosteroid, when the patient's condition has become refractory to the same.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Compounds of the disclosure are believed to be useful as anti-viral agents, for example in the treatment or prevention of respiratory syncitial infection. In particular the compounds of the present disclosure may be suitable for the use in the treatment or prevention of said viral infection and in particular may be capable of reducing viral load and/or ameliorating symptoms after infection.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

An effective amount will be an amount effective to cause reduction in symptoms of respiratory syncitial virus (RSV) infection and/or exacerbation of a respiratory disorder for example a chronic respiratory disorder such as asthma or COPD by RSV infection, for example an amount which causes a reduction in viral load, and may be determined by a skilled person by reference to the severity of the condition in the subject. Typically an amount of 0.1 to 10 e.g. 1 to 5 µg/kg or a dose of 7 to 700 e.g. 70 to 350 µg per day will be suitable.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with corticosteroids (e.g. budesonide, beclomethasone dipropionate, fluticasone propionate, mometasone furoate, fluticasone furoate), beta agonists (e.g. terbutaline, salbutamol, salmeterol, formoterol), anti-muscarinic (e.g. iprotropium bromide, Tiotropium), xanthines (e.g. theophylline), phophodiesterase inhibitors (roflumilast, cilomolast) and/or anti-viral compounds (e.g. Ribavirin, RSV604).

ABBREVIATIONS

Abbreviations used herein are as defined in the table below. Any abbreviations not defined are intended to convey their generally accepted meaning.

aq aqueous
ATP adenosine-5'-triphosphate
BALF bronchoalveolae lavage fluid
BSA bovine serum albumin
CPE cytopathic effect
COPD chronic obstructive pulmonary disease
DMEM Dulbecco's Modified Eagle Medium
Et ethyl
FEV(1) forced expiratory volume in 1 second
FBS foetal bovine serum
hr hour(s)
HRP horseradish peroxidase
JNK c-Jun N-terminal kinase
LHC8 serum-free Lechner and LaVeck media
MAPK mitogen protein activated protein kinase
Me methyl
min minute(s)
mM millimolar
MOI multiplicity of infection
MTT 3-(4,5-dimethylthiazol-2-yl)-2,5-diphenyltetrazolium bromide
NHBEC normal human bronchial epithelial cells
nm nanometer(s)
OD optical density
PBS phosphate buffered saline
PI3K PI3 kinase
PKC protein kinase C
RSV respiratory syncitial virus
RT room temperature
SDS sodium dodecyl sulphate
$TCID_{50}$ 50% tissue culture infectious dose
TMB 3,3',5,5'-tetramethylbenzidine
TNFα tumor necrosis factor alpha
URTI upper respiratory tract infection(s)
VPSSM very low protein cell culture media

COMPOUND EXAMPLES

Those compound examples of the invention listed below (Table 1) were prepared as previously disclosed [Ito K. et al., WO 2010/067131, PCT/GB2009/051703, 17 Jun. 2010].

TABLE 1

| Ex. No. | Structure | Name |
|---|---|---|
| 1 | 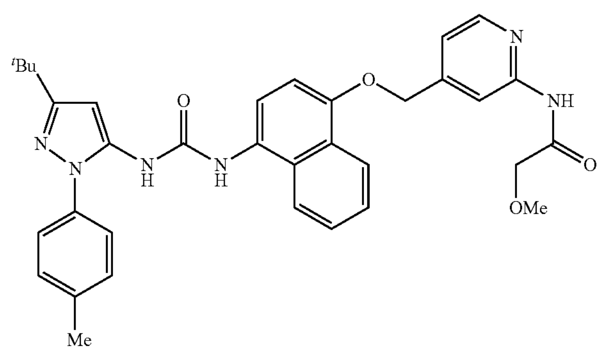 [SMILES: COCC(=O)Nc1cc(COc2ccc(NC(=O)Nc3cc(C(C)(C)C)nn3-c3ccc(C)cc3)c3ccccc23)ccn1] | N-(4-((4-(3-(3-tert-Butyl-1-p-tolyl-1H-pyrazol-5-yl)ureido) naphthalen-1-yloxy)methyl) pyridin-2-yl)-2-methoxy acetamide. |
| 2 | 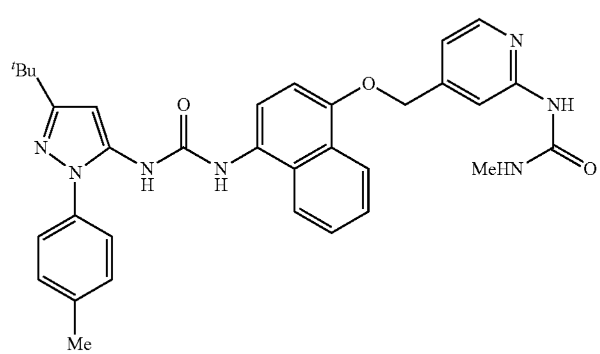 [SMILES: CNC(=O)Nc1cc(COc2ccc(NC(=O)Nc3cc(C(C)(C)C)nn3-c3ccc(C)cc3)c3ccccc23)ccn1] | Methyl 4-((4-(3-(3-tert-butyl-1-p-tolyl-1H-pyrazol-5-yl)ureido) naphthalen-1-yloxy)methyl) pyridin-2-ylurea. |

TABLE 1-continued

| Ex. No. | Structure | Name |
|---|---|---|
| 3 | 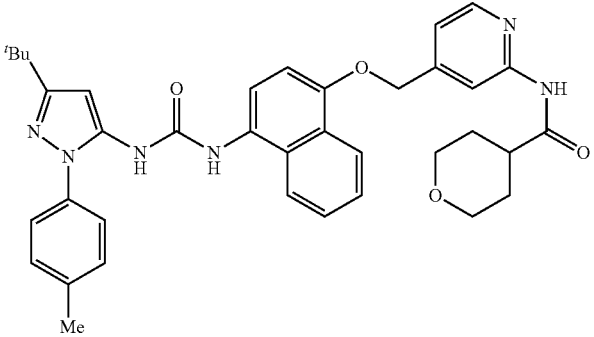 [SMILES: Cc1ccc(-n2nc(C(C)(C)C)cc2NC(=O)Nc2ccc(OCc3ccnc(NC(=O)C4CCOCC4)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide. |
| 4 | 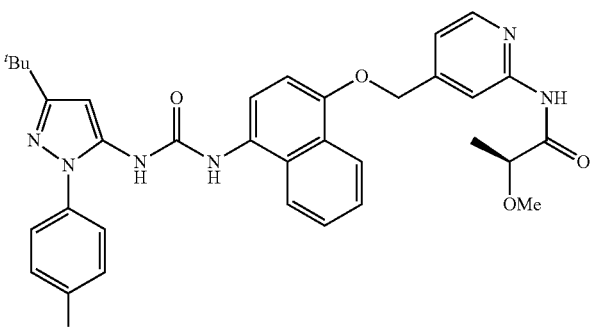 | (S)-N-(4-((4-(3-(3-tert-Butyl-1-p-tolyl-1H-pyrazol-5-yl)ureido)naphthalen-1-yloxy)methyl)pyridin-2-yl)-2-methoxypropanamide. |
| 5 | 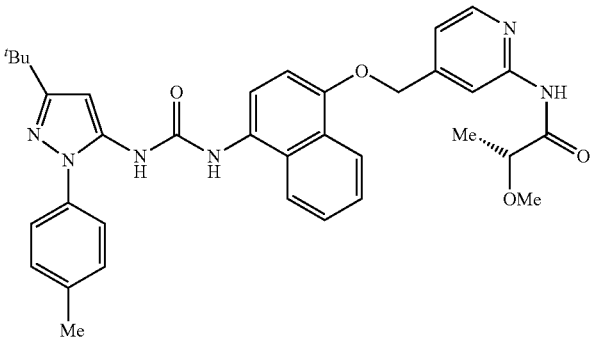 [SMILES: CO[C@H](C)C(=O)Nc1cc(COc2ccc(NC(=O)Nc3cc(C(C)(C)C)nn3-c3ccc(C)cc3)c3ccccc23)ccn1] | (R)-N-(4-((4-(3-(3-tert-Butyl-1-p-tolyl-1H-pyrazol-5-yl)ureido)naphthalen-1-yloxy)methyl)pyridin-2-yl)-2-methoxypropanamide. |
| 6 | 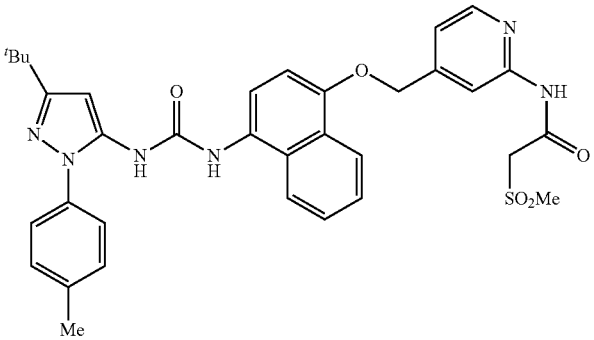 [SMILES: Cc1ccc(-n2nc(C(C)(C)C)cc2NC(=O)Nc2ccc(OCc3ccnc(NC(=O)CS(C)(=O)=O)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-2-(methylsulfonyl)acetamide. |

TABLE 1-continued

| Ex. No. | Structure | Name |
|---|---|---|
| 7 | 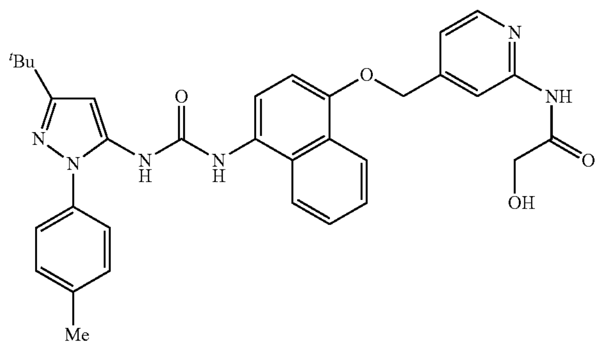 [SMILES: Cc1ccc(-n2nc(C(C)(C)C)cc2NC(=O)Nc2ccc(OCc3ccnc(NC(=O)CO)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-2-hydroxyacetamide. |
| 8 | 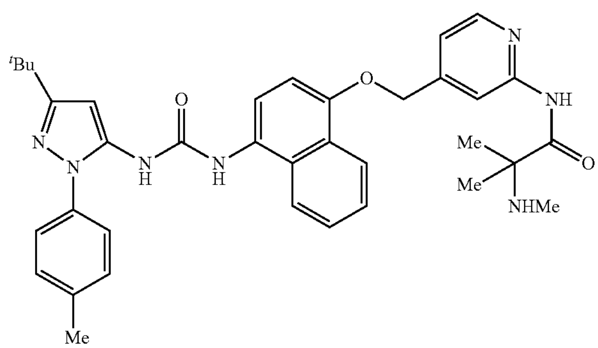 [SMILES: CNC(C)(C)C(=O)Nc1cc(COc2ccc(NC(=O)Nc3cc(C(C)(C)C)nn3-c3ccc(C)cc3)c3ccccc23)ccn1] | N-(4-((4-(3-(3-tert-Butyl-1-p-tolyl-1H-pyrazol-5-yl)ureido)naphthalen-1-yloxy)methyl)pyridin-2-yl)-2-methyl-2-(methylamino)propanamide. |
| 9 | 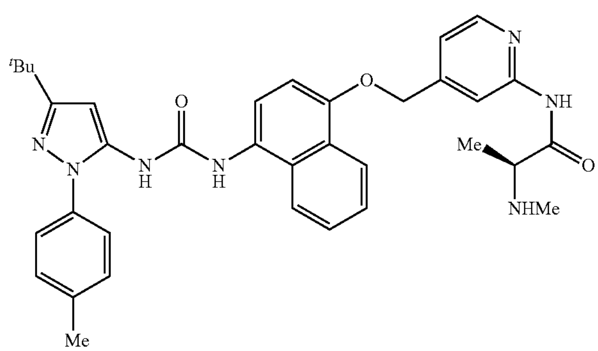 [SMILES: CN[C@@H](C)C(=O)Nc1cc(COc2ccc(NC(=O)Nc3cc(C(C)(C)C)nn3-c3ccc(C)cc3)c3ccccc23)ccn1] | (S)-N-(4-((4-(3-(3-tert-Butyl-1-p-tolyl-1H-pyrazol-5-yl)ureido)naphthalen-1-yloxy)methyl)pyridin-2-yl)-2-(methylamino)propanamide. |
| 10 | 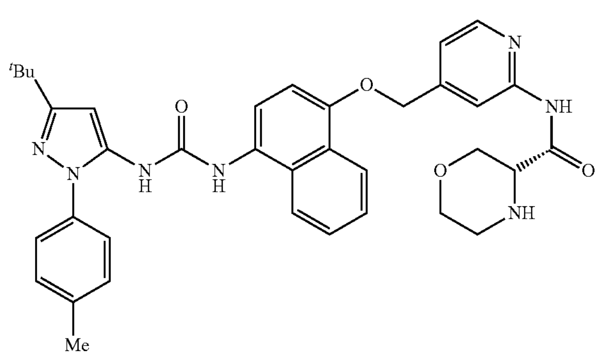 | (R)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide. |

TABLE 1-continued

| Ex. No. | Structure | Name |
|---|---|---|
| 11 | 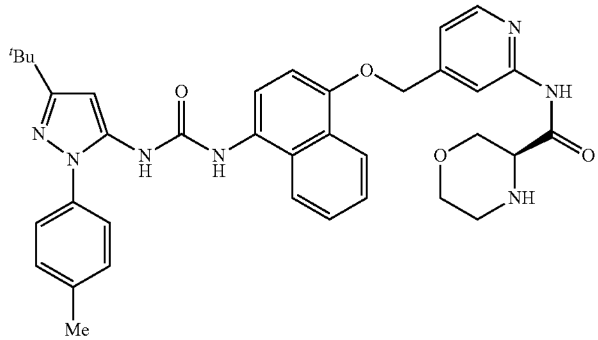 [SMILES: Cc1ccc(-n2nc(C(C)(C)C)cc2NC(=O)Nc2ccc(OCc3ccnc(NC(=O)[C@@H]4COCCN4)c3)c3ccccc23)cc1] | (S)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide. |
| 12 | 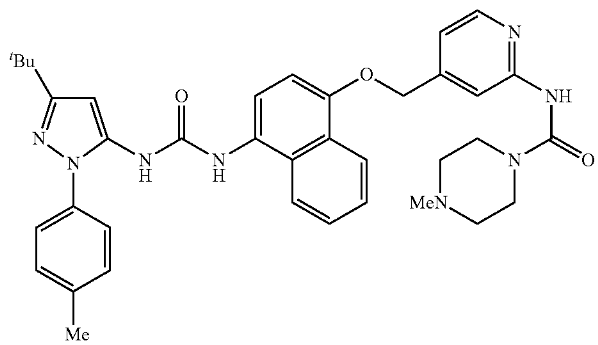 [SMILES: Cc1ccc(-n2nc(C(C)(C)C)cc2NC(=O)Nc2ccc(OCc3ccnc(NC(=O)N4CCN(C)CC4)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-4-methyl piperazine-1-carboxamide. |
| 13 | 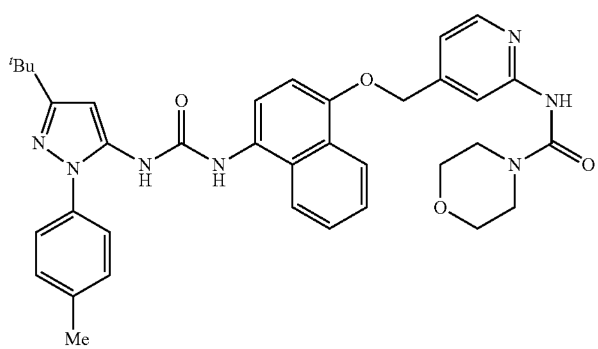 | N-(4-((4-(3-(3-tert-Butyl-1-p-tolyl-1H-pyrazol-5-yl)ureido)naphthalen-1-yloxy)methyl)pyridin-2-yl)morpholine-4-carboxamide. |
| 14 | 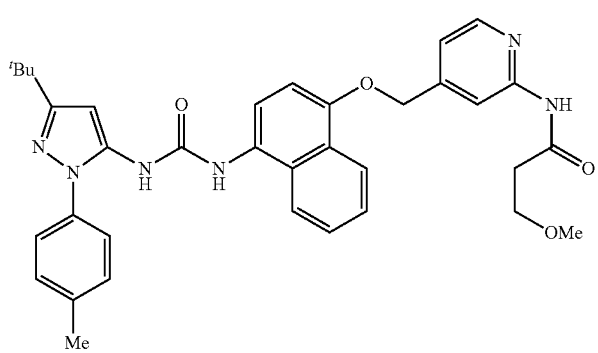 [SMILES: COCCC(=O)Nc1cc(COc2ccc(NC(=O)Nc3cc(C(C)(C)C)nn3-c3ccc(C)cc3)c3ccccc23)ccn1] | N-(4-((4-(3-(3-tert-Butyl-1-p-tolyl-1H-pyrazol-5-yl)ureido)naphthalen-1-yloxy)methyl)pyridin-2-yl)-3-methoxy propanamide. |

TABLE 1-continued

| Ex. No. | Structure | Name |
|---|---|---|
| 15 | 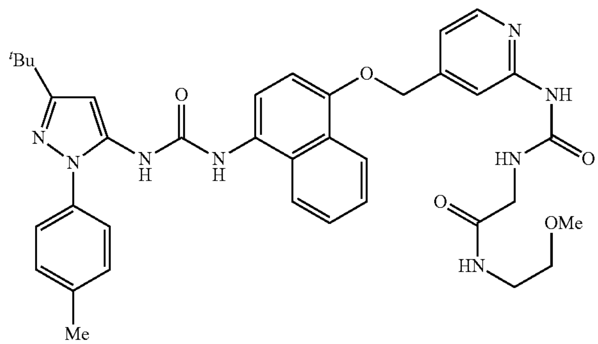 [SMILES: COCCNC(=O)CNC(=O)Nc1cc(COc2ccc(NC(=O)Nc3cc(C(C)(C)C)nn3-c3ccc(C)cc3)c3ccccc23)ccn1] | 2-(3-(4-((4-(3-(3-tert-Butyl-1-p-tolyl-1H-pyrazol-5-yl)ureido)naphthalen-1-yloxy)methyl)pyridin-2-yl)ureido)-N-(2-methoxyethyl)acetamide. |
| 16 | 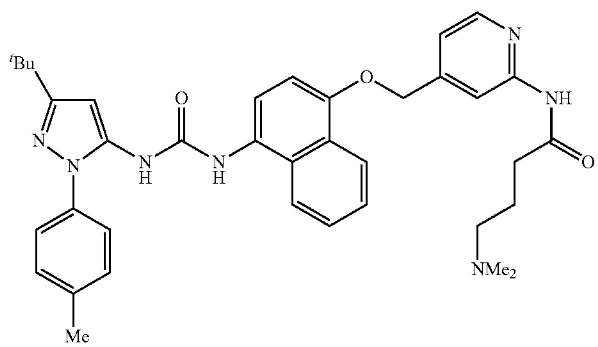 [SMILES: Cc1ccc(-n2nc(C(C)(C)C)cc2NC(=O)Nc2ccc(OCc3ccnc(NC(=O)CCCN(C)C)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-4-(dimethylamino)butanamide. |
| 17 | 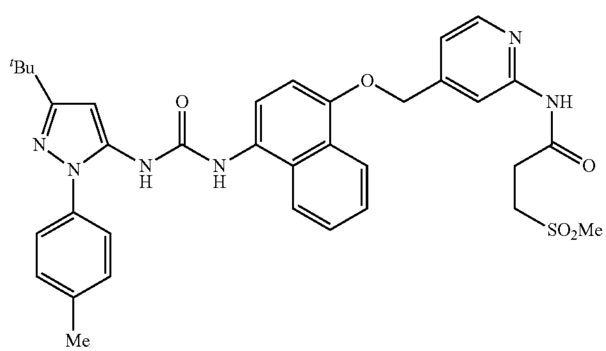 [SMILES: Cc1ccc(-n2nc(C(C)(C)C)cc2NC(=O)Nc2ccc(OCc3ccnc(NC(=O)CCS(C)(=O)=O)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-3-(methylsulfonyl)propanamide. |
| 18 | 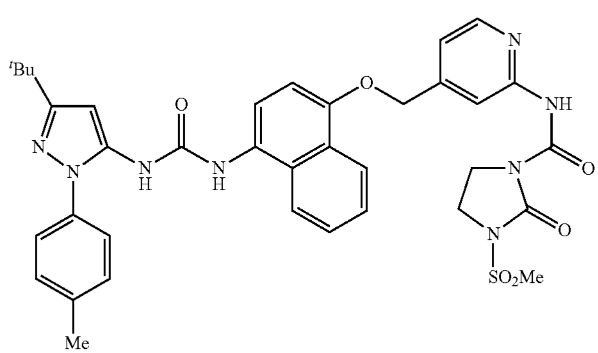 [SMILES: Cc1ccc(-n2nc(C(C)(C)C)cc2NC(=O)Nc2ccc(OCc3ccnc(NC(=O)N4CCN(S(C)(=O)=O)C4=O)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-3-(methylsulfonyl)-2-oxoimidazolidine-1-carboxamide. |

TABLE 1-continued

| Ex. No. | Structure | Name |
|---|---|---|
| 19 | 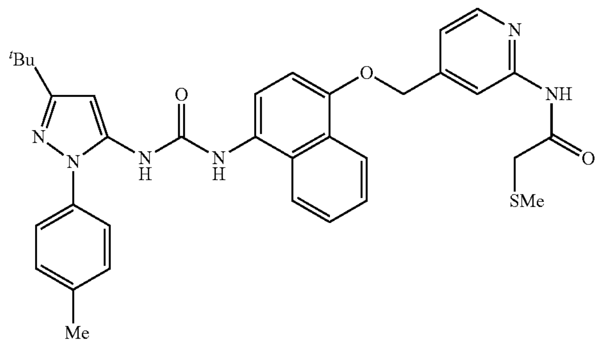 | N-(4-((4-(3-(3-tert-Butyl-1-p-tolyl-1H-pyrazol-5-yl)ureido)naphthalen-1-yloxy)methyl)pyridin-2-yl)-2-(methylthio)acetamide. |
| 20 | 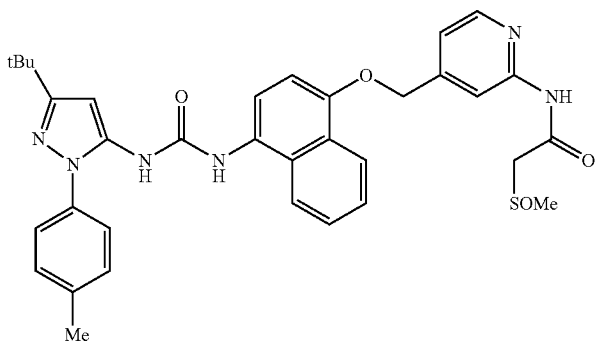 | N-(4-((4-(3-(3-tert-Butyl-1-p-tolyl-1H-pyrazol-5-yl)ureido)naphthalen-1-yloxy)methyl)pyridin-2-yl)-2-(methylsulfinyl)acetamide. |
| 21 | 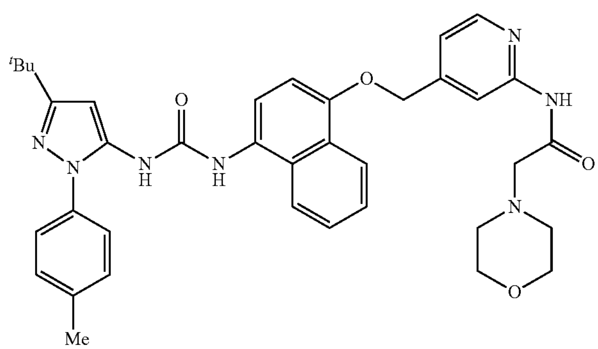 [SMILES: Cc1ccc(-n2nc(C(C)(C)C)cc2NC(=O)Nc2ccc(OCc3ccnc(NC(=O)CN4CCOCC4)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-2-morpholinoacetamide. |
| 22 | 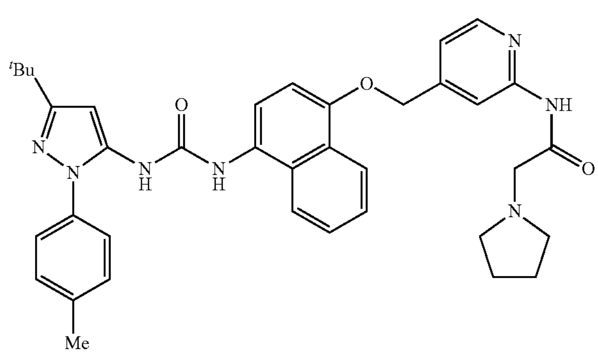 [SMILES: Cc1ccc(-n2nc(C(C)(C)C)cc2NC(=O)Nc2ccc(OCc3ccnc(NC(=O)CN4CCCC4)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide. |

TABLE 1-continued

| Ex. No. | Structure | Name |
|---|---|---|
| 23 | 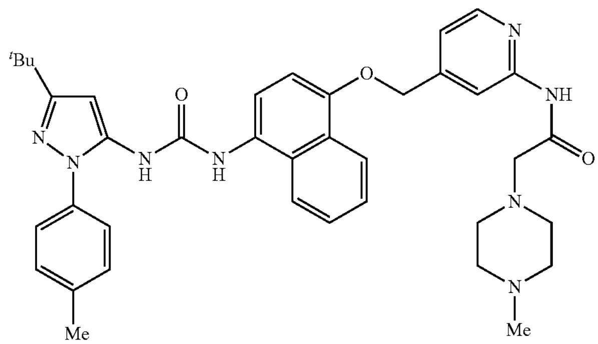 [SMILES: Cc1ccc(-n2nc(C(C)(C)C)cc2NC(=O)Nc2ccc(OCc3ccnc(NC(=O)CN4CCN(C)CC4)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-2-(4-methyl piperazin-1-yl)acetamide. |
| 24 | 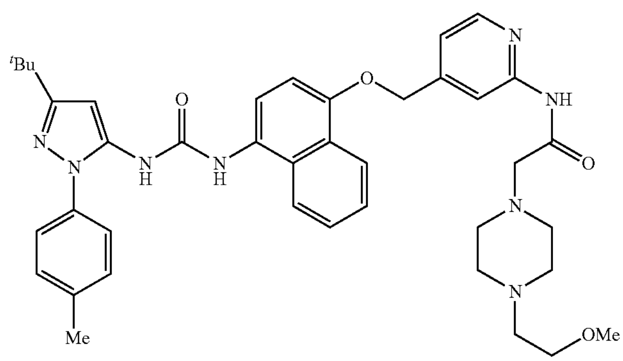 [SMILES: COCCN1CCN(CC(=O)Nc2cc(COc3ccc(NC(=O)Nc4cc(C(C)(C)C)nn4-c4ccc(C)cc4)c4ccccc34)ccn2)CC1] | N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide. |
| 25 | 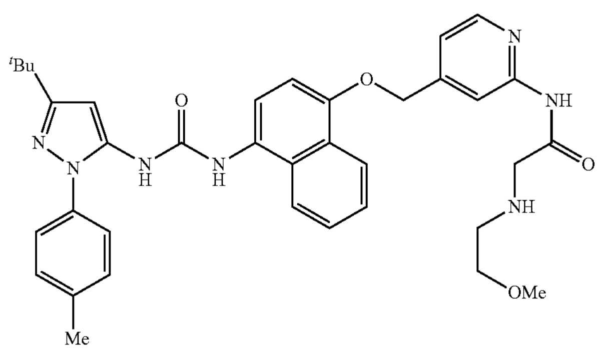 [SMILES: COCCNCC(=O)Nc1cc(COc2ccc(NC(=O)Nc3cc(C(C)(C)C)nn3-c3ccc(C)cc3)c3ccccc23)ccn1] | N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide. |
| 26 | 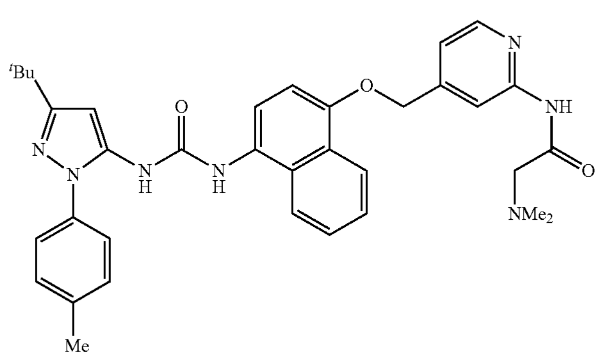 | N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide. |

TABLE 1-continued

| Ex. No. | Structure | Name |
|---|---|---|
| 27 | 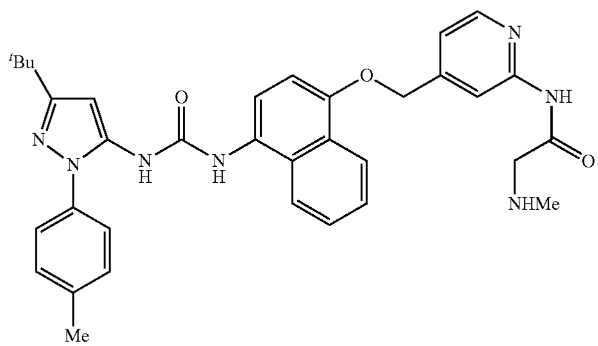 [SMILES: CNCC(=O)Nc1cc(COc2ccc(NC(=O)Nc3cc(C(C)(C)C)nn3-c3ccc(C)cc3)c3ccccc23)ccn1] | N-(4-((4-(3-(3-tert-Butyl-1-p-tolyl-1H-pyrazol-5-yl)ureido)naphthalen-1-yloxy)methyl)pyridin-2-yl)-2-(methylamino)acetamide |
| 28 | 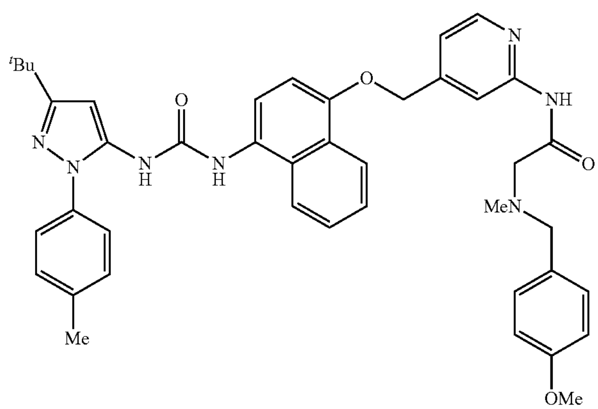 [SMILES: COc1ccc(CN(C)CC(=O)Nc2cc(COc3ccc(NC(=O)Nc4cc(C(C)(C)C)nn4-c4ccc(C)cc4)c4ccccc34)ccn2)cc1] | N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide. |
| 29 | 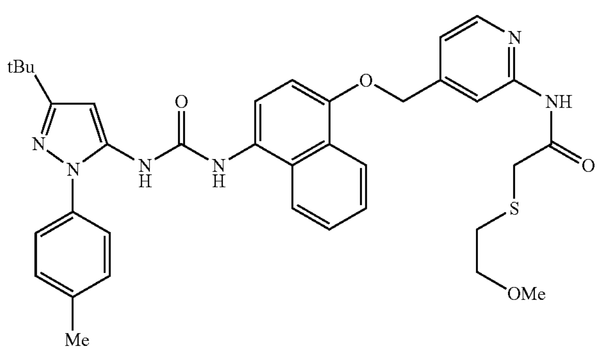 [SMILES: COCCSCC(=O)Nc1cc(COc2ccc(NC(=O)Nc3cc(C(C)(C)C)nn3-c3ccc(C)cc3)c3ccccc23)ccn1] | N-(4-((4-(3-(3-tert-Butyl-1-p-tolyl-1H-pyrazol-5-yl)ureido)naphthalen-1-yloxy)methyl)pyridin-2-yl)-2-(2-methoxyethylthio)acetamide. |
| 30 | 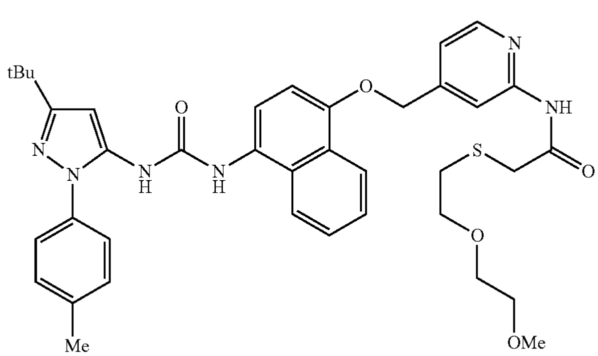 [SMILES: COCCOCCSCC(=O)Nc1cc(COc2ccc(NC(=O)Nc3cc(C(C)(C)C)nn3-c3ccc(C)cc3)c3ccccc23)ccn1] | N-(4-((4-(3-(3-tert-Butyl-1-p-tolyl-1H-pyrazol-5-yl)ureido)naphthalen-1-yloxy)methyl)pyridin-2-yl)-2-(2-(2-methoxyethoxy)ethylthio)acetamide. |

TABLE 1-continued

| Ex. No. | Structure | Name |
|---|---|---|
| 31 | 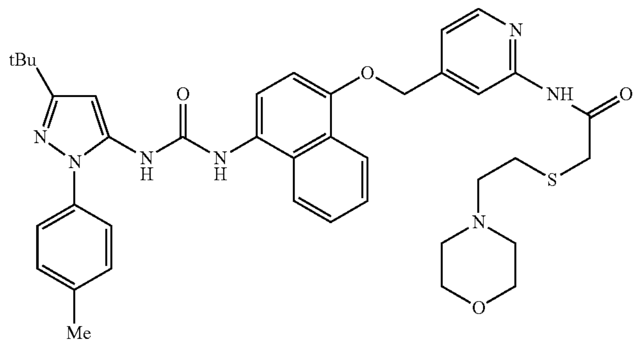 [SMILES: Cc1ccc(-n2nc(C(C)(C)C)cc2NC(=O)Nc2ccc(OCc3ccnc(NC(=O)CSCCN4CCOCC4)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-2-(2-morpholinoethylthio)acetamide. |
| 32 | 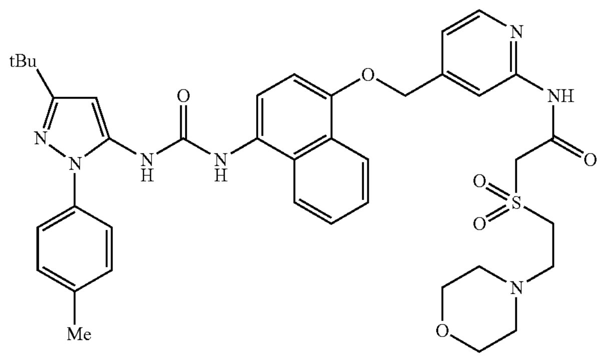 [SMILES: Cc1ccc(-n2nc(C(C)(C)C)cc2NC(=O)Nc2ccc(OCc3ccnc(NC(=O)CS(=O)(=O)CCN4CCOCC4)c3)c3ccccc23)cc1] | N-(4-((4-(3-(3-tert-Butyl-1-p-tolyl-1H-pyrazol-5-yl)ureido)naphthalen-1-yloxy)methyl)pyridin-2-yl)-2-(2-morpholinoethylsulfonyl)acetamide. |
| 33 | 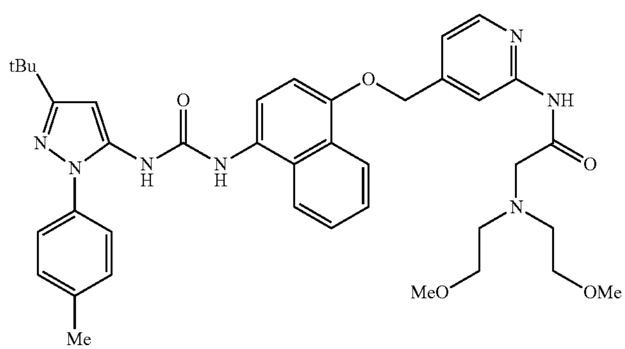 [SMILES: COCCN(CCOC)CC(=O)Nc1cc(COc2ccc(NC(=O)Nc3cc(C(C)(C)C)nn3-c3ccc(C)cc3)c3ccccc23)ccn1] | 2-(Bis(2-methoxyethyl)amino)-N-(4-((4-(3-(3-tert-butyl-1-p-tolyl-1H-pyrazol-5-yl)ureido)naphthalen-1-yloxy)methyl)pyridin-2-yl)acetamide. |
| 34 | 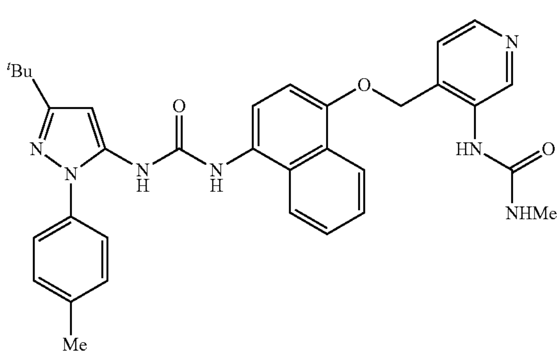 [SMILES: CNC(=O)Nc1cnccc1COc1ccc(NC(=O)Nc2cc(C(C)(C)C)nn2-c2ccc(C)cc2)c2ccccc12] | 1-(4-((3-Methylureidopyridin-4-yl)methoxy)naphthalen-1-yl)-3-(3-tert-butyl-1-p-tolyl-1H-pyrazol-5-yl)urea. |

TABLE 1-continued

| Ex. No. | Structure | Name |
|---|---|---|
| 35 | 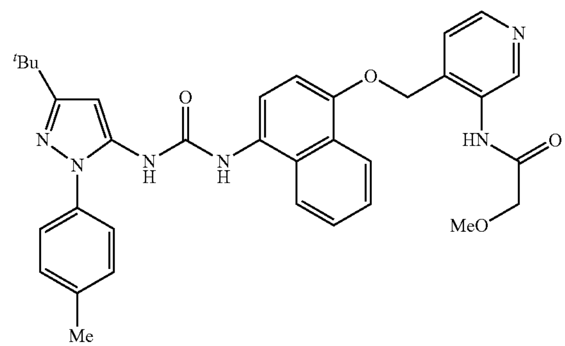 [SMILES: COCC(=O)Nc1cnccc1COc1ccc(NC(=O)Nc2cc(C(C)(C)C)nn2-c2ccc(C)cc2)c2ccccc12] | N-(4-((4-(3-(3-tert-Butyl-1-p-tolyl-1H-pyrazol-5-yl)ureido)naphthalen-1-yloxy)methyl)pyridin-3-yl)-2-methoxyacetamide. |
| 36 | 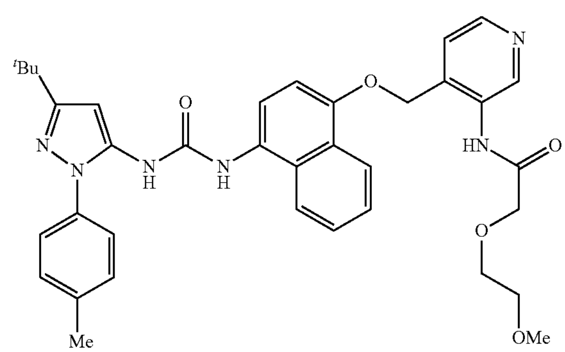 [SMILES: COCCOCC(=O)Nc1cnccc1COc1ccc(NC(=O)Nc2cc(C(C)(C)C)nn2-c2ccc(C)cc2)c2ccccc12] | N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide. |
| 37 | 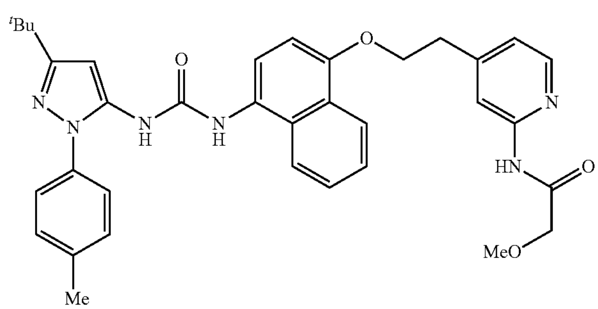 [SMILES: COCC(=O)Nc1cc(CCOc2ccc(NC(=O)Nc3cc(C(C)(C)C)nn3-c3ccc(C)cc3)c3ccccc23)ccn1] | N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide. |
| 38 | 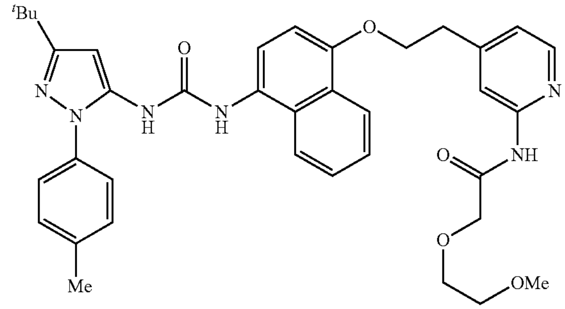 [SMILES: COCCOCC(=O)Nc1cc(CCOc2ccc(NC(=O)Nc3cc(C(C)(C)C)nn3-c3ccc(C)cc3)c3ccccc23)ccn1] | N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide. |

TABLE 1-continued

| Ex. No. | Structure | Name |
|---|---|---|
| 39 | 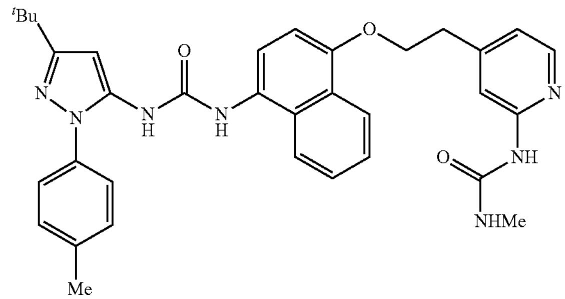 [SMILES: CNC(=O)Nc1cc(CCOc2ccc(NC(=O)Nc3cc(C(C)(C)C)nn3-c3ccc(C)cc3)c3ccccc23)ccn1] | 4-(2-(4-(3-(3-tert-Butyl-1-p-tolyl-1H-pyrazol-5-yl)ureido)naphthalen-1-yloxy)ethyl)-1-methyl-3-(pyridin-2-yl)urea. |
| 40 | 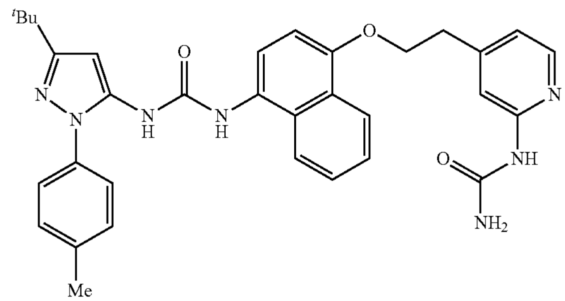 [SMILES: Cc1ccc(-n2nc(C(C)(C)C)cc2NC(=O)Nc2ccc(OCCc3ccnc(NC(N)=O)c3)c3ccccc23)cc1] | 4-(2-(4-(3-(3-tert-Butyl-1-p-tolyl-1H-pyrazol-5-yl)ureido)naphthalen-1-yloxy)ethyl)-3-(pyridin-2-yl)urea. |
| 41 | 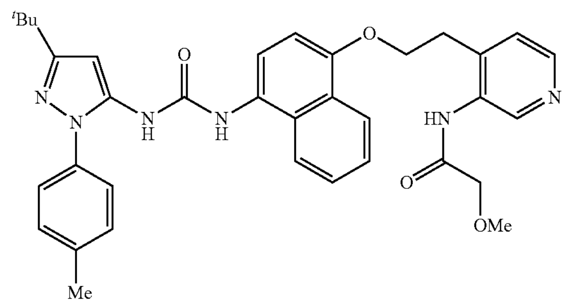 [SMILES: COCC(=O)Nc1cnccc1CCOc1ccc(NC(=O)Nc2cc(C(C)(C)C)nn2-c2ccc(C)cc2)c2ccccc12] | N-(4-(2-(4-(3-(3-tert-Butyl-1-p-tolyl-1H-pyrazol-5-yl)ureido)naphthalen-1-yloxy)ethyl)pyridin-3-yl)-2-methoxyacetamide. |
| 42 | 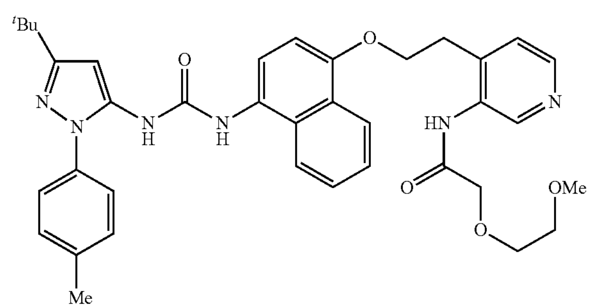 [SMILES: COCCOCC(=O)Nc1cnccc1CCOc1ccc(NC(=O)Nc2cc(C(C)(C)C)nn2-c2ccc(C)cc2)c2ccccc12] | N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide. |
| 43 | 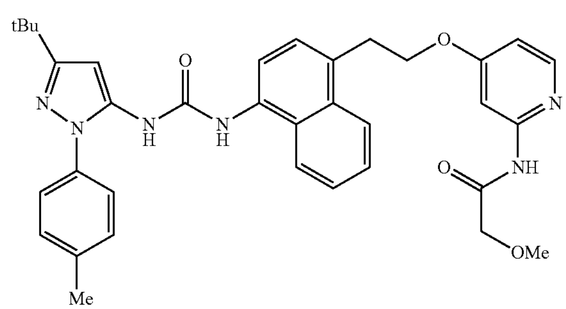 [SMILES: COCC(=O)Nc1cc(OCCc2ccc(NC(=O)Nc3cc(C(C)(C)C)nn3-c3ccc(C)cc3)c3ccccc23)ccn1] | N-(4-(2-(4-(3-(3-tert-butyl-1-p-tolyl-1H-pyrazol-5-yl)ureido)naphthalen-1-yl)ethoxy)pyridin-2-yl)-2-methoxyacetamide. |

TABLE 1-continued

| Ex. No. | Structure | Name |
|---|---|---|
| 44 | 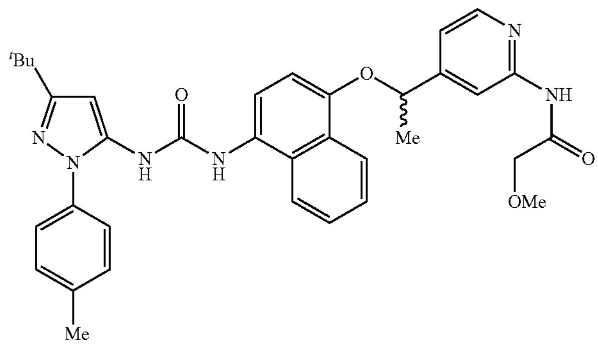 [SMILES: COCC(=O)Nc1cc(C(C)Oc2ccc(NC(=O)Nc3cc(C(C)(C)C)nn3-c3ccc(C)cc3)c3ccccc23)ccn1] | N-(4-(1-(4-(3-(3-tert-Butyl-1-p-tolyl-1H-pyrazol-5-yl)ureido)naphthalen-1-yloxy)ethyl)pyridin-2-yl)-2-methoxy acetamide. |
| 45 | 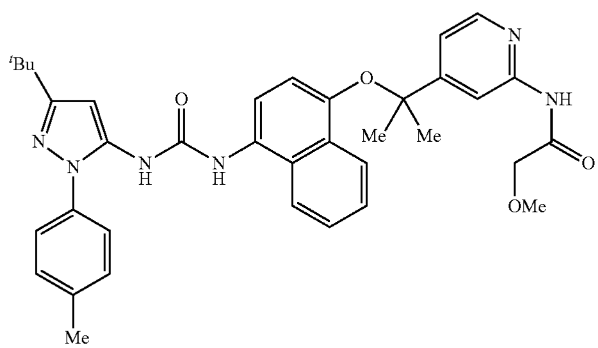 [SMILES: COCC(=O)Nc1cc(C(C)(C)Oc2ccc(NC(=O)Nc3cc(C(C)(C)C)nn3-c3ccc(C)cc3)c3ccccc23)ccn1] | N-(4-(2-(4-(3-(3-tert-Butyl-1-p-tolyl-1H-pyrazol-5-yl)ureido)naphthalen-1-yloxy)-2-methyl propyl)pyridin-2-yl)-2-methoxy acetamide. |
| 46 | 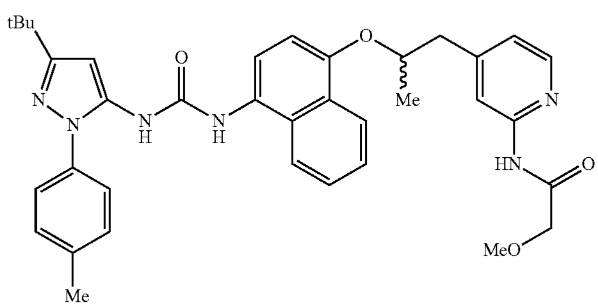 [SMILES: COCC(=O)Nc1cc(CC(C)Oc2ccc(NC(=O)Nc3cc(C(C)(C)C)nn3-c3ccc(C)cc3)c3ccccc23)ccn1] | N-(4-(2-(4-(3-(3-tert-Butyl-1-p-tolyl-1H-pyrazol-5-yl)ureido)naphthalen-1-yloxy)propyl)pyridin-2-yl)-2-methoxy acetamide. |
| 47 | 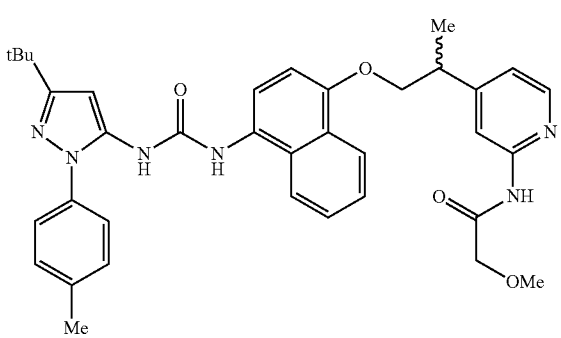 [SMILES: COCC(=O)Nc1cc(C(C)COc2ccc(NC(=O)Nc3cc(C(C)(C)C)nn3-c3ccc(C)cc3)c3ccccc23)ccn1] | N-(4-(1-(4-(3-(3-tert-Butyl-1-p-tolyl-1H-pyrazol-5-yl)ureido)naphthalen-1-yloxy)propan-2-yl)pyridin-2-yl)-2-methoxy acetamide. |

TABLE 1-continued

| Ex. No. | Structure | Name |
|---|---|---|
| 48 | 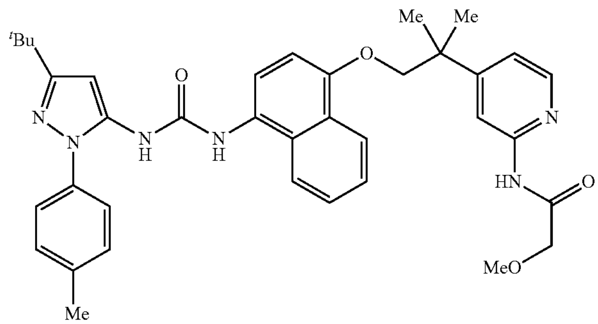 [SMILES: COCC(=O)Nc1cc(C(C)(C)COc2ccc(NC(=O)Nc3cc(C(C)(C)C)nn3-c3ccc(C)cc3)c3ccccc23)ccn1] | N-(4-(1-(4-(3-(3-tert-Butyl-1-p-tolyl-1-pyrazol-5-yl)ureido)naphthalen-1-yloxy)-2-methyl propan-2-yl)pyridin-2-yl)-2-methoxyacetamide. |
| 49 | 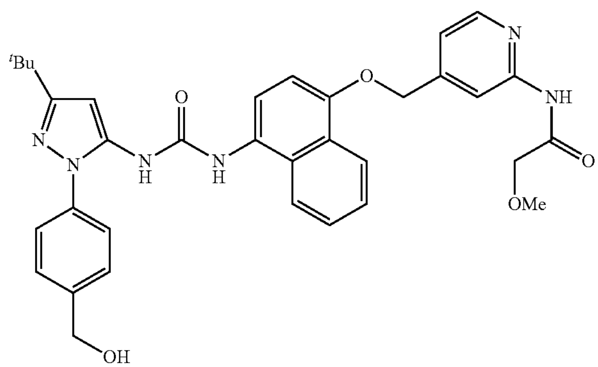 [SMILES: COCC(=O)Nc1cc(COc2ccc(NC(=O)Nc3cc(C(C)(C)C)nn3-c3ccc(CO)cc3)c3ccccc23)ccn1] | N-(4-((4-(3-(3-tert-Butyl-1-(4-(hydroxymethyl)phenyl)-1H-pyrazol-5-yl)ureido)naphthalen-1-yloxy)methyl)pyridin-2-yl)-2-methoxyacetamide. |
| 50 | 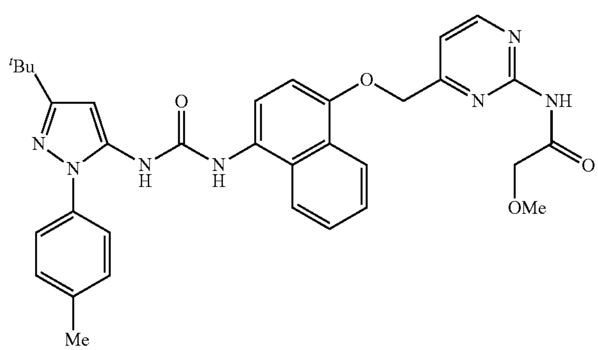 [SMILES: COCC(=O)Nc1nccc(COc2ccc(NC(=O)Nc3cc(C(C)(C)C)nn3-c3ccc(C)cc3)c3ccccc23)n1] | N-(4-((4-(3-(3-tert-Butyl-1-p-tolyl-1H-pyrazol-5-yl)ureido)naphthalen-1-yloxy)methyl)pyrimidin-2-yl)-2-methoxy acetamide |
| 51 | 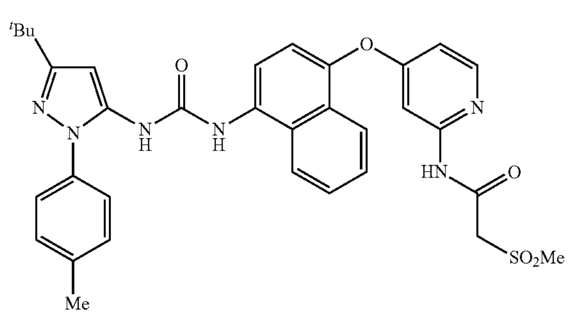 [SMILES: Cc1ccc(-n2nc(C(C)(C)C)cc2NC(=O)Nc2ccc(Oc3ccnc(NC(=O)CS(C)(=O)=O)c3)c3ccccc23)cc1] | N-(4-(4-(3-(3-tert-Butyl-1-p-tolyl-1H-pyrazol-5-yl)ureido)naphthalen-1-yloxy)pyridin-2-yl)-2-(methylsulfonyl)acetamide. |

Those compound examples of the invention listed below (Table 2) were prepared as previously disclosed [Ito K. et al., WO 2010/067130, PCT/GB2009/051702, 17 Jun. 2010].

TABLE 2

| 52 | | N-(4-(4-(3-(3-tert-Butyl-1-p-tolyl-1H-pyrazol-5-yl)ureido) naphthalen-1-yloxy)pyridin-2-yl)-2-(2-methoxyethoxy) acetamide. |
|---|---|---|
| 53 | | N-(4-(4-(3-(3-tert-Butyl-1-p-tolyl-1H-pyrazol-5-yl)ureido) naphthalen-1-yloxy)pyridin-2-yl)tetrahydro-2H-pyran-4-carboxamide. |
| 54 | | N-(4-(4-(3-(3-tert-Butyl-1-p-tolyl-1H-pyrazol-5-yl)ureido) naphthalen-1-yloxy)pyridin-2-yl)-2-(methylthio)acetamide. |
| 55 | | N-(4-(4-(3-(3-tert-Butyl-1-p-tolyl-1H-pyrazol-5-yl)ureido) naphthalen-1-yloxy)pyridin-2-yl)-3-methoxypropanamide. |
| 56 | | N-(4-(4-(3-(3-tert-Butyl-1-p-tolyl-1H-pyrazol-5-yl)ureido) naphthalen-1-yloxy)pyridin-2-yl)-2-hydroxyacetamide. |

TABLE 2-continued

| 57 | 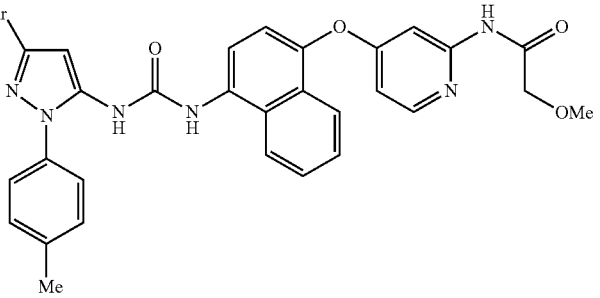 | N-(4-(4-(3-(3-Isopropyl-1-p-tolyl-1H-pyrazol-5-yl)ureido)naphthalen-1-yloxy)pyridin-2-yl)-2-methoxyacetamide. |
| 58 | 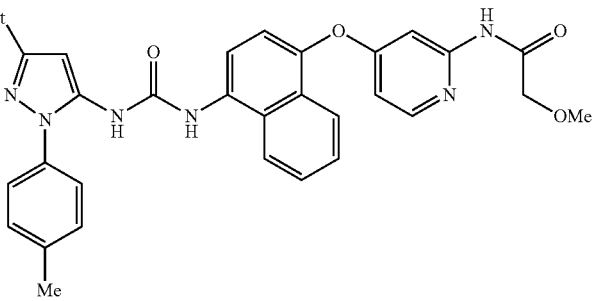 | N-(4-(4-(3-(3-Ethyl-1-p-tolyl-1H-pyrazol-5-yl)ureido)naphthalen-1-yloxy)pyridin-2-yl)-2-methoxy acetamide. |
| 59 | 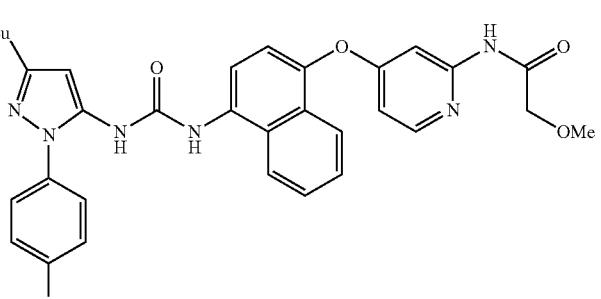 | N-(4-(4-(3-(3-tert-Butyl-1-p-tolyl-1H-pyrazol-5-yl)ureido)naphthalen-1-yloxy)pyridin-2-yl)-2-methoxyacetamide. |
| 60 | 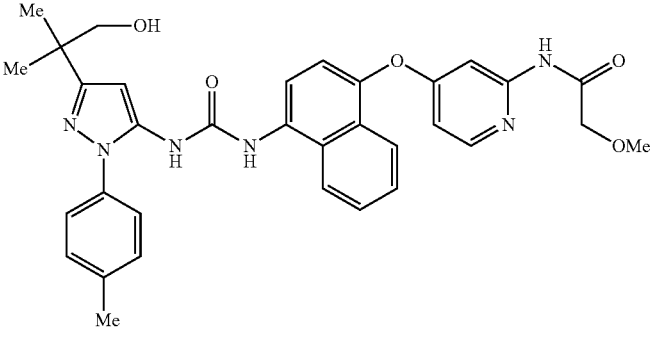 [SMILES: COCC(=O)Nc1cc(Oc2ccc(NC(=O)Nc3cc(C(C)(C)CO)nn3-c3ccc(C)cc3)c3ccccc23)ccn1] | N-(4-(4-(3-(3-(1-Hydroxy-2-methylpropan-2-yl)-1-p-tolyl-1H-pyrazol-5-yl)ureido)naphthalen-1-yloxy)pyridin-2-yl)-2-methoxyacetamide. |
| 61 | 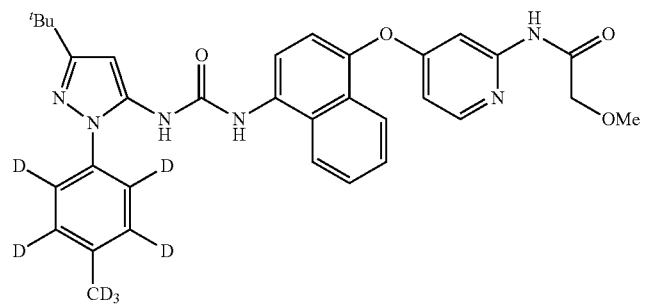 [SMILES: [2H]c1c([2H])c(C([2H])([2H])[2H])c([2H])c([2H])c1-n1nc(C(C)(C)C)cc1NC(=O)Nc1ccc(Oc2ccnc(NC(=O)COC)c2)c2ccccc12] | N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide. |

TABLE 2-continued

| 62 | [structure] | N-(4-(4-(3-(3-tert-Butyl-1-p-tolyl-1H-pyrazol-5-yl)ureido)naphthalen-1-yloxy)pyridin-2-yl)-2-morpholinoacetamide |
| 63 | [structure] | N-(4-(4-(3-(3-tert-Butyl-1-p-tolyl-1H-pyrazol-5-yl)ureido)naphthalen-1-yloxy)pyridin-2-yl)-(dimethylamino)acetamide |
| 64 | [structure] | N-(4-(4-(3-(3-tert-Butyl-1-p-tolyl-1H-pyrazol-5-yl)ureido)naphthalen-1-yloxy)pyridin-2-yl)-2-(2-methoxyethylamino)acetamide. |
| 65 | [structure] | N-(4-(4-(3-(3-tert-Butyl-1-p-tolyl-1H-pyrazol-5-yl)ureido)naphthalen-1-yloxy)pyridin-2-yl)pyrrolidine-1-carboxamide. |
| 66 | [structure] | N-(4-(4-(3-(3-tert-Butyl-1-p-tolyl-1H-pyrazol-5-yl)ureido)naphthalen-1-yloxy)pyridin-2-yl)-2-ureidoacetamide. |

TABLE 2-continued

| # | Structure | Name |
|---|---|---|
| 67 | 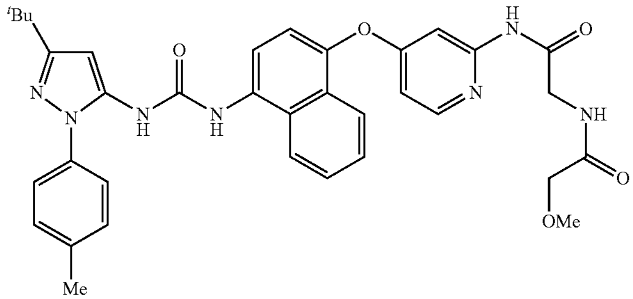 [SMILES: COCC(=O)NCC(=O)Nc1cc(Oc2ccc(NC(=O)Nc3cc(C(C)(C)C)nn3-c3ccc(C)cc3)c3ccccc23)ccn1] | N-(4-(4-(3-(3-tert-Butyl-1-p-tolyl-1H-pyraozl-5-yl)ureido)napththalen-1-yloxy)pyridin-2-yl)-2-(2-methoxyacetamido)acetamide. |
| 68 | 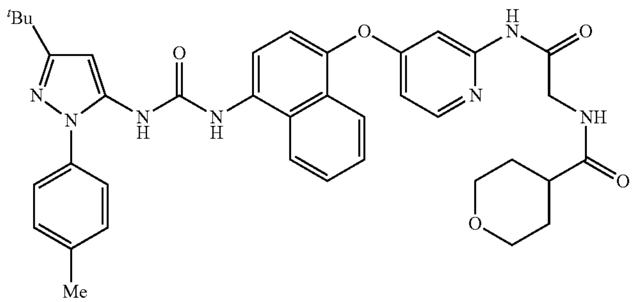 [SMILES: Cc1ccc(-n2nc(C(C)(C)C)cc2NC(=O)Nc2ccc(Oc3ccnc(NC(=O)CNC(=O)C4CCOCC4)c3)c3ccccc23)cc1] | N-(2-(4-(4-(3-(3-tert-Butyl-1-p-tolyl-1H-pyrazol-5-yl)ureido)naphthalen-1-yloxy)pyridin-2-ylamino)-2-oxoethyl)tetrahydro-2H-pyran-4-carboxamide. |
| 69 | 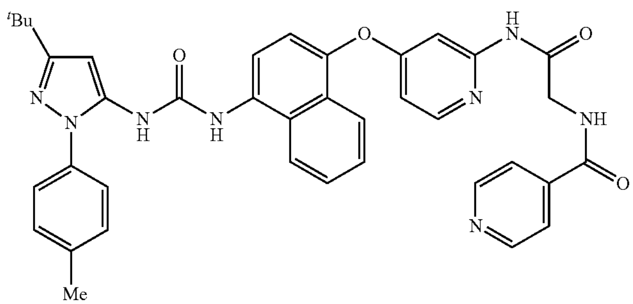 [SMILES: Cc1ccc(-n2nc(C(C)(C)C)cc2NC(=O)Nc2ccc(Oc3ccnc(NC(=O)CNC(=O)c4ccncc4)c3)c3ccccc23)cc1] | N-(2-(4-(4-(3-(3-tert-Butyl-1-p-tolyl-1H-pyrazol-5-yl)ureido)naphthalen-1-yloxy)pyridin-2-ylamino)-2-oxoethyl)isonicotinamide |
| 70 | 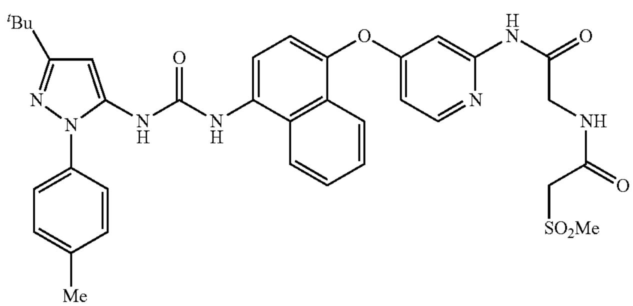 [SMILES: Cc1ccc(-n2nc(C(C)(C)C)cc2NC(=O)Nc2ccc(Oc3ccnc(NC(=O)CNC(=O)CS(C)(=O)=O)c3)c3ccccc23)cc1] | N-(4-(4-(3-(3-tert-Butyl-1-p-tolyl-1H-pyrazol-5-yl)ureido)naphthalen-1-yloxy)pyridin-2-yl)-2-(2-(methylsulfonyl)acetamido)acetamide. |
| 71 | 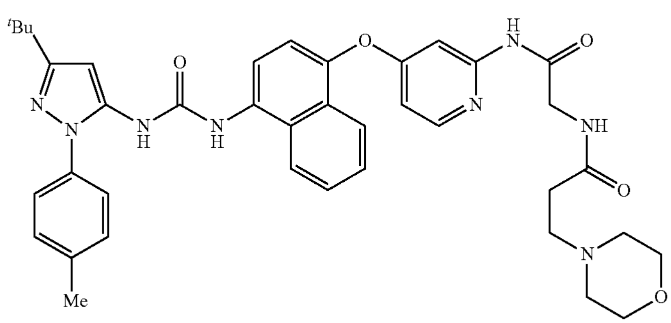 [SMILES: Cc1ccc(-n2nc(C(C)(C)C)cc2NC(=O)Nc2ccc(Oc3ccnc(NC(=O)CNC(=O)CCN4CCOCC4)c3)c3ccccc23)cc1] | N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide. |

TABLE 2-continued

| 72 | 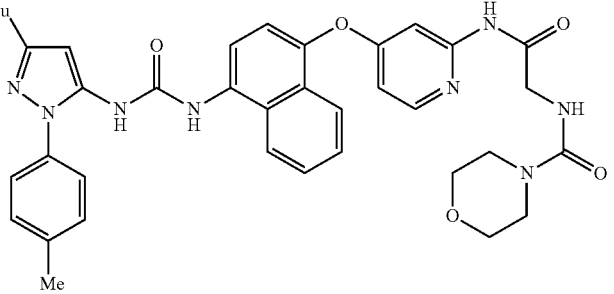 | N-(2-(4-(4-(3-(3-tert-Butyl-1-p-tolyl-1H-pyrazol-5-yl)ureido)naphthalen-1-yloxy)pyridin-2-ylamino)-2-oxoethyl)morpholine-4-carboxamide. |
| --- | --- | --- |
| 73 | 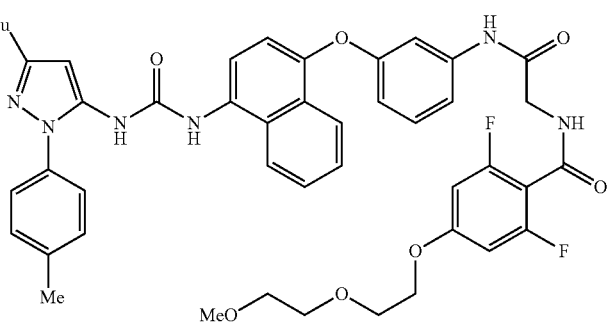 | N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide. |
| 74 | 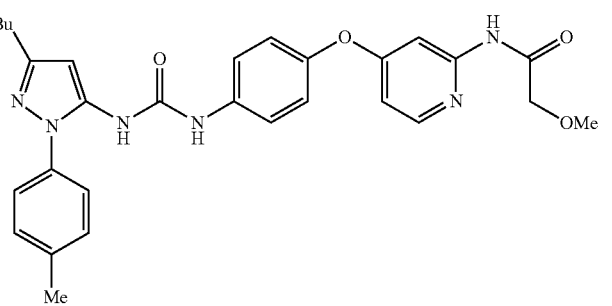 | N-(4-(4-(3-(3-tert-Butyl-1-p-tolyl-1H-pyrazol-5-yl)ureido)phenoxy)pyridin-2-yl)-2-methoxyacetamide. |
| 75 | 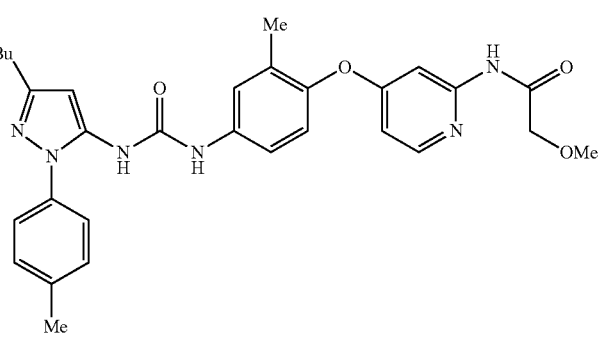 | N-(4-(4-(3-(3-tert-Butyl-1-p-tolyl-1H-pyrazol-5-yl)ureido)-2-methylphenoxy)pyridin-2-yl)-2-methoxyacetamide. |
| 76 | 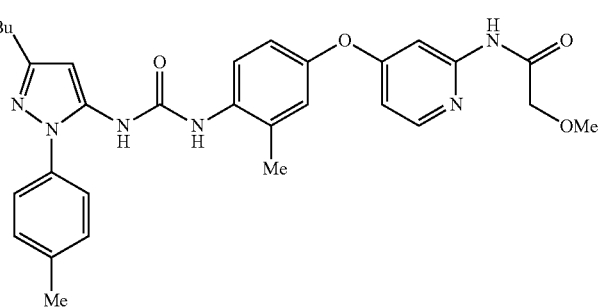 | N-(4-(4-(3-(3-tert-Butyl-1-p-tolyl-1H-pyrazol-5-yl)ureido)-3-methylphenoxy)pyridin-2-yl)-2-methoxyacetamide. |

TABLE 2-continued

| # | Structure | Name |
|---|---|---|
| 77 | 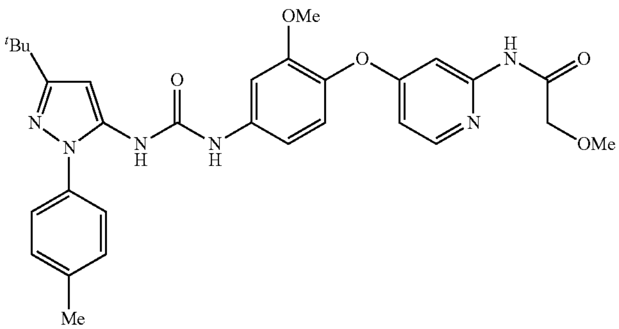 [SMILES: COCC(=O)Nc1cc(Oc2ccc(NC(=O)Nc3cc(C(C)(C)C)nn3-c3ccc(C)cc3)cc2OC)ccn1] | N-(4-(4-(3-(3-tert-Butyl-1-p-tolyl-1H-pyrazol-5-yl)ureido)-2-methoxyphenoxy)pyridin-2-yl)-2-methoxyacetamide. |
| 78 | 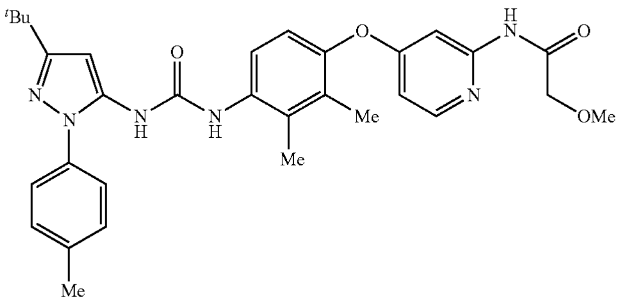 [SMILES: COCC(=O)Nc1cc(Oc2ccc(NC(=O)Nc3cc(C(C)(C)C)nn3-c3ccc(C)cc3)c(C)c2C)ccn1] | N-(4-(4-(3-(3-tert-Butyl-1-p-tolyl-1H-pyrazol-5-yl)ureido)-2,3-dimethylphenoxy)pyridin-2-yl)-2-methoxyacetamide. |
| 79 | 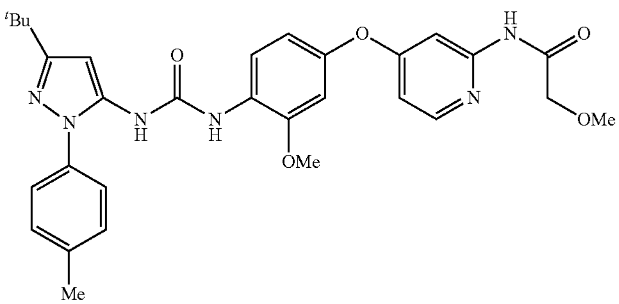 [SMILES: COCC(=O)Nc1cc(Oc2ccc(NC(=O)Nc3cc(C(C)(C)C)nn3-c3ccc(C)cc3)c(OC)c2)ccn1] | N-(4-(4-(3-(3-tert-Butyl-1-p-tolyl-1H-pyrazol-5-yl)ureido)-3-methoxyphenoxy)pyridin-2-yl)-2-methoxyacetamide. |
| 80 | 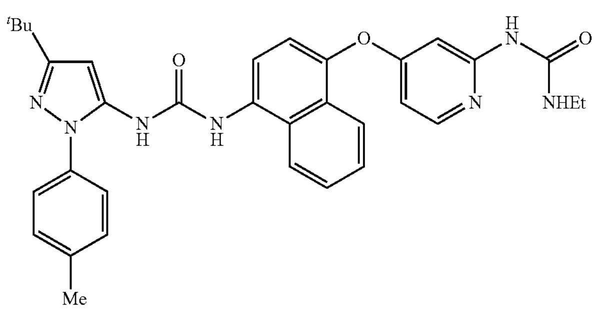 | N-Ethyl-N'-4-(4-(3-(3-tert-butyl-1-p-tolyl-1H-pyrazol-5-yl)ureido)naphthalen-1-yloxy)pyridin-2-ylurea. |
| 81 | 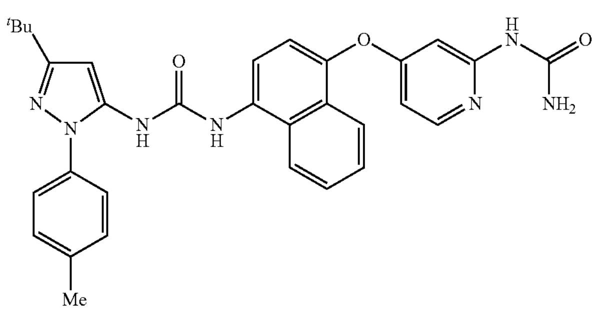 [SMILES: Cc1ccc(-n2nc(C(C)(C)C)cc2NC(=O)Nc2ccc(Oc3ccnc(NC(N)=O)c3)c3ccccc23)cc1] | 4-(4-(3-(3-tert-Butyl-1-p-tolyl-1H-pyrazol-5-yl)ureido)naphthalen-1-yloxy)pyridin-2-ylurea. |

TABLE 2-continued

| | | |
|---|---|---|
| 82 | 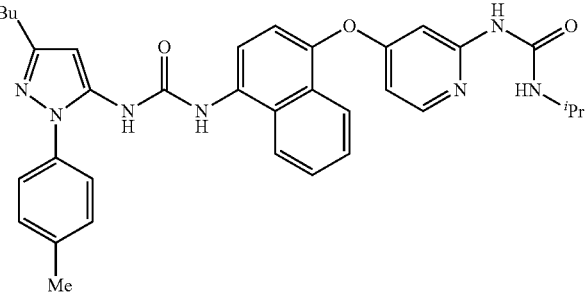 | N-Propan-2-yl-N'-4-(4-(3-(3-tert-butyl-1-p-tolyl-1H-pyrazol-5-yl)ureido)naphthalen-1-yloxy)pyridin-2-ylurea. |
| 83 | 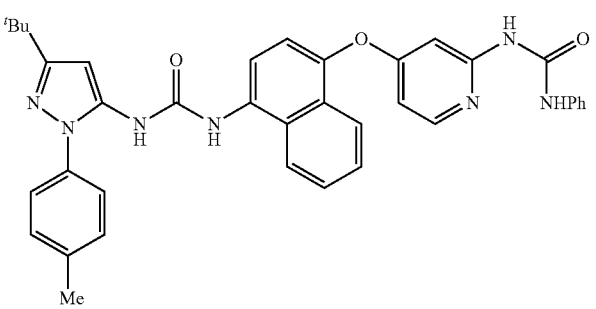 | 1-(3-(tert-Butyl)-1-(p-tolyl)-1H-pyrazol-5-yl)-3-(4-((2-(3-phenylureido)pyridin-4-yl)oxy)naphthalen-1-yl)urea. |
| 84 | 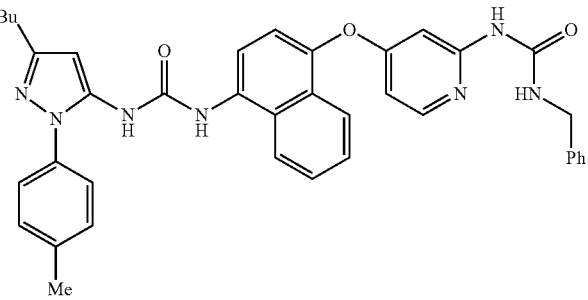 | 1-(4-((2-(3-Benzylureido)pyridin-4-yl)oxy)naphthalen-1-yl)-3-(3-(tert-butyl)-1-(p-tolyl)-1H-pyrazol-5-yl)urea. |
| 85 | 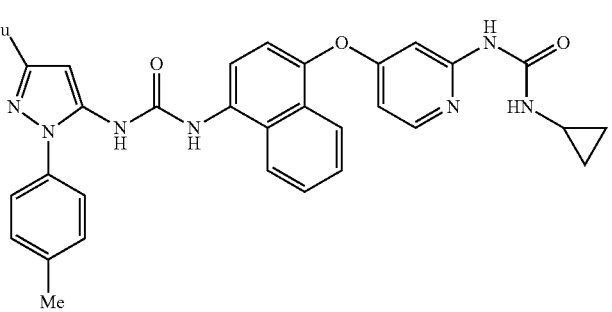 | 1-(4-((2-(3-Cyclopropylureido)pyridin-4-yl)oxy)naphthalen-1-yl)-3-(3-(tert-butyl)-1-(p-tolyl)-1H-pyrazol-5-yl)urea. |
| 86 | 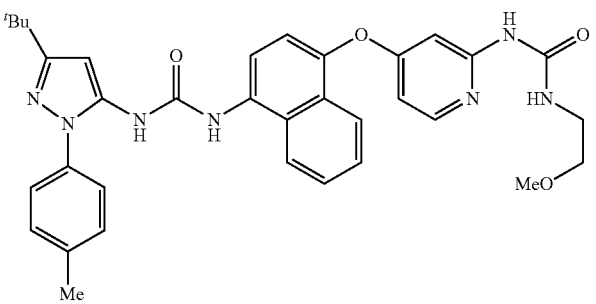 [SMILES: COCCNC(=O)Nc1cc(Oc2ccc(NC(=O)Nc3cc(C(C)(C)C)nn3-c3ccc(C)cc3)c3ccccc23)ccn1] | 1-(3-(tert-Butyl)-1-(p-tolyl)-1H-pyrazol-5-yl)-3-(4-((2-(3-(2-methoxyethyl)ureido)pyridin-4-yl)oxy)naphthalen-1-yl)urea. |

TABLE 2-continued

| # | Structure | Name |
|---|---|---|
| 87 | | 1-(3-(tert-Butyl)-1-(p-tolyl)-1H-pyrazol-5-yl)-3-(4-((2-(3-cyclopentyl)ureido)pyridin-4-yl)oxy)naphthalen-1-yl)urea. |
| 88 | | 1-(3-(tert-Butyl)-1-(p-tolyl)-1H-pyrazol-5-yl)-3-(4-((2-(3-methyl)ureido)pyridin-4-yl)oxy)naphthalen-1-yl)urea. |
| 89 | | Ethyl 2-(3-(4-((4-(3-(3-(tert-butyl)-1-(p-tolyl)-1H-pyrazol-5-yl)ureido)naphthalen-1-yl)oxy)pyridin-2-yl)ureido)acetate. |
| 90 | | 4-(3-(4-(4-(3-(3-tert-Butyl-1-p-tolyl-1H-pyrazol-5-yl)ureido)naphthalen-1-yloxy)pyridin-2-yl)ureido)piperidine. |
| 91 | | N-Acetyl 4-(3-(4-(4-(3-(3-tert-butyl-1-p-tolyl-1H-pyrazol-5-yl)ureido)naphthalen-1-yloxy)pyridin-2-yl)ureido)piperidine. |

TABLE 2-continued

| | | |
|---|---|---|
| 92 | 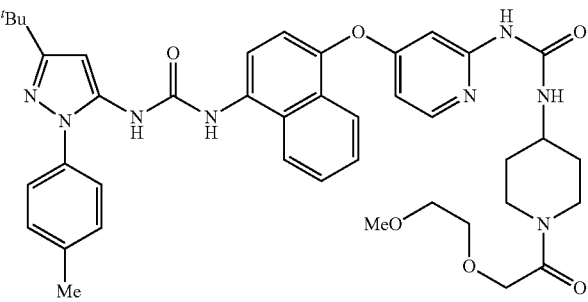 [SMILES: COCCOCC(=O)N1CCC(NC(=O)Nc2cc(Oc3ccc(NC(=O)Nc4cc(C(C)(C)C)nn4-c4ccc(C)cc4)c4ccccc34)ccn2)CC1] | 2-(2-Methoxyethoxy)-1-(4-(4-(3-(4-(3-(3-tert-butyl-1-p-tolyl-1H-pyrazol-5-yl)ureido)naphthalen-1-yloxy)pyridin-2-yl)ureido)piperidin-1-yl)ethanone. |
| 93 | 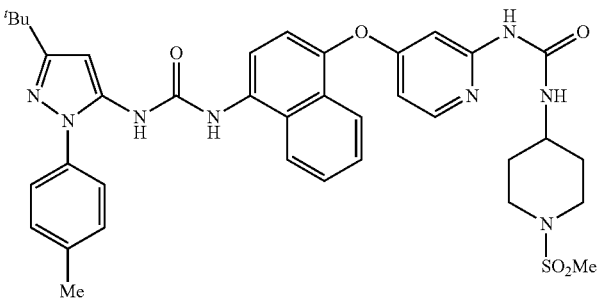 [SMILES: Cc1ccc(-n2nc(C(C)(C)C)cc2NC(=O)Nc2ccc(Oc3ccnc(NC(=O)NC4CCN(S(C)(=O)=O)CC4)c3)c3ccccc23)cc1] | N-Methylsulfonyl-4-(3-(4-(3-(3-tert-butyl-1-p-tolyl-1H-pyrazol-5-yl)ureido)naphthalen-1-yloxy)pyridin-2-yl)ureido)piperidine. |
| 94 | 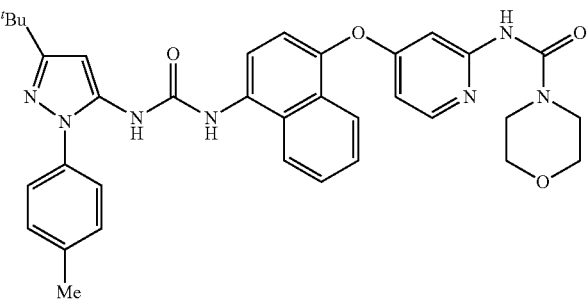 [SMILES: Cc1ccc(-n2nc(C(C)(C)C)cc2NC(=O)Nc2ccc(Oc3ccnc(NC(=O)N4CCOCC4)c3)c3ccccc23)cc1] | N-(4-(4-(3-(3-tert-Butyl-1-p-tolyl-1H-pyrazol-5-yl)ureido)naphthalen-1-yloxy)pyridin-2-yl)morpholine-4-carboxamide. |
| 95 | 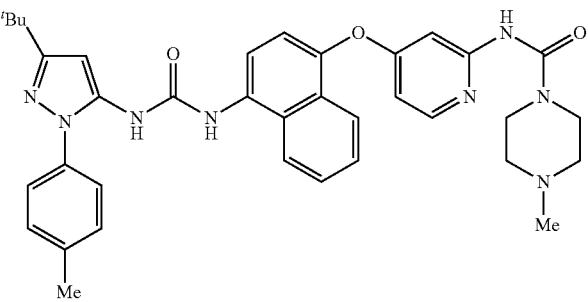 [SMILES: Cc1ccc(-n2nc(C(C)(C)C)cc2NC(=O)Nc2ccc(Oc3ccnc(NC(=O)N4CCN(C)CC4)c3)c3ccccc23)cc1] | N-(4-((4-(3-(3-(tert-Butyl)-1-(p-tolyl)-1H-pyrazol-5-yl)ureido)naphthalen-1-yl)oxy)pyridin-2-yl)-4-methylpiperazine-1-carboxamide. |
| 96 | 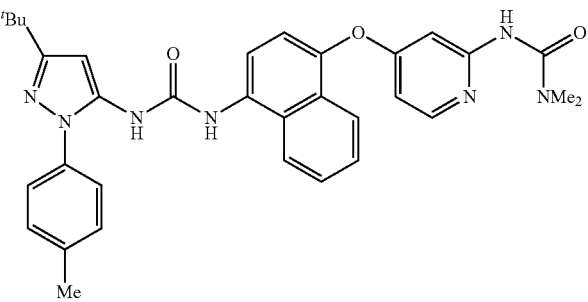 [SMILES: Cc1ccc(-n2nc(C(C)(C)C)cc2NC(=O)Nc2ccc(Oc3ccnc(NC(=O)N(C)C)c3)c3ccccc23)cc1] | 3-(4-((4-(3-(3-(tert-Butyl)-1-(p-tolyl)-1H-pyrazol-5-yl)ureido)naphthalen-1-yl)oxy)pyridin-2-yl)-1,1-dimethylurea. |

TABLE 2-continued

| # | Structure | Name |
|---|---|---|
| 97 | 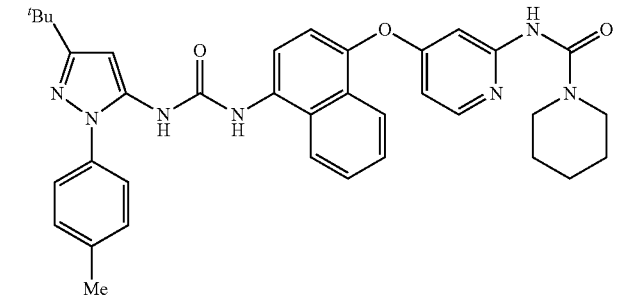 [SMILES: Cc1ccc(-n2nc(C(C)(C)C)cc2NC(=O)Nc2ccc(Oc3ccnc(NC(=O)N4CCCCC4)c3)c3ccccc23)cc1] | N-(4-((4-(3-(3-(tert-Butyl)-1-(p-tolyl)-1H-pyrazol-5-yl)ureido)naphthalen-1-yl)oxy)pyridin-2-yl)piperidine-1-carboxamide. |
| 98 | 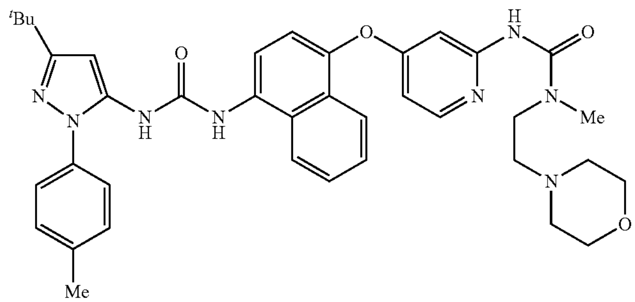 [SMILES: Cc1ccc(-n2nc(C(C)(C)C)cc2NC(=O)Nc2ccc(Oc3ccnc(NC(=O)N(C)CCN4CCOCC4)c3)c3ccccc23)cc1] | N-Methyl-N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea. |
| 99 | 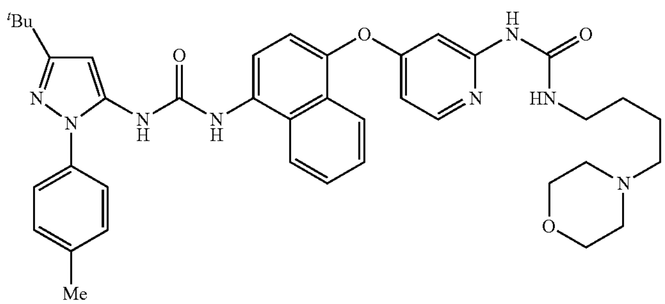 [SMILES: Cc1ccc(-n2nc(C(C)(C)C)cc2NC(=O)Nc2ccc(Oc3ccnc(NC(=O)NCCCCN4CCOCC4)c3)c3ccccc23)cc1] | N-(4-(morpholin-4-yl)butyl)-N'-4-(4-(3-(3-tert-butyl-1-p-tolyl-1H-pyrazol-5-yl)ureido)naphthalen-1-yloxy)pyridin-2-ylurea. |
| 100 | 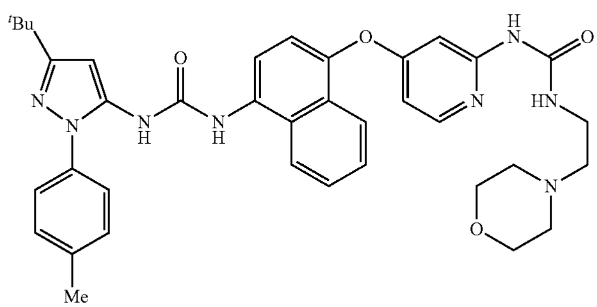 [SMILES: Cc1ccc(-n2nc(C(C)(C)C)cc2NC(=O)Nc2ccc(Oc3ccnc(NC(=O)NCCN4CCOCC4)c3)c3ccccc23)cc1] | N-(2-(Morpholin-4-yl)ethyl)-N'-4-(4-(3-(3-tert-butyl-1-p-tolyl-1H-pyrazol-5-yl)ureido)naphthalen-1-yloxy)pyridin-2-ylurea. |
| 101 | 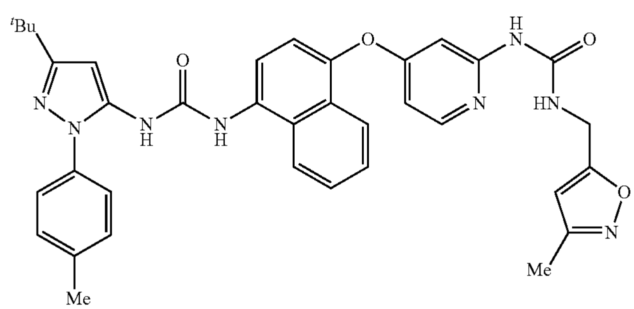 [SMILES: Cc1ccc(-n2nc(C(C)(C)C)cc2NC(=O)Nc2ccc(Oc3ccnc(NC(=O)NCc4cc(C)no4)c3)c3ccccc23)cc1] | N-(3-Methylisoxazol-5-yl)methyl-N'-4-(4-(3-(3-tert-butyl-1-p-tolyl-1H-pyrazol-5-yl)ureido)naphthalen-1-yloxy)pyridin-2-ylurea. |

TABLE 2-continued

| | | |
|---|---|---|
| 102 | [structure] | N-(1-Methyl)piperidin-4-yl-N'-4-(4-(3-(3-tert-butyl-1-p-tolyl-1H-pyrazol-5-yl)ureido)naphthalen-1-yloxy)pyridin-2-ylurea. |
| 103 | [structure] | N-(4-(4-(3-(3-tert-Butyl-1-p-tolyl-1H-pyrazol-5-yl)ureido)naphthalen-1-yloxy)pyridin-2-yl)-4-hydroxypiperidine-1-carboxamide. |
| 104 | [structure] | N-(3-(Imidazol-1-yl)propyl)-N'-4-(4-(3-(3-tert-butyl-1-p-tolyl-1H-pyrazol-5-yl)ureido)naphthalen-1-yloxy)pyridin-2-ylurea. |
| 105 | [structure] | N-(2-(3-(4-(4-(3-(3-tert-Butyl-1-p-tolyl-1H-pyrazol-5-yl)ureido)naphthalen-1-yloxy)pyridin-2-yl)ureido)acetyl)pyrrolidine. |
| 106 | [structure] | (R)-N-(4-(4-(3-(3-tert-Butyl-1-p-tolyl-1H-pyrazol-5-yl)ureido)naphthalen-1-yloxy)pyridin-2-yl)-3-(dimethylamino)pyrrolidine-1-carboxamide. |

TABLE 2-continued

| # | Name |
|---|---|
| 107 | 2-(3-(4-(4-(3-(3-tert-Butyl-1-p-tolyl-1H-pyrazol-5-yl)ureido)naphthalen-1-yloxy)pyridin-2-yl)ureido)-N-methylacetamide. |
| 108 | 2-(3-(4-(4-(3-(3-tert-Butyl-1-p-tolyl-1H-pyrazol-5-yl)ureido)naphthalen-1-yloxy)pyridin-2-yl)ureido)-N-(2-morpholino ethyl)acetamide. |
| 109 | 2-(3-(4-(4-(3-(3-tert-Butyl-1-p-tolyl-1H-pyrazol-5-yl)ureido)naphthalen-1-yloxy)pyridin-2-yl)ureido)acetyl morpholine. |
| 110 | 2-(3-(4-(4-(3-(3-tert-Butyl-1-p-tolyl-1H-pyrazol-5-yl)ureido)naphthalen-1-yloxy)pyridin-2-yl)ureido)-N-(2-(pyridin-4-yl)ethyl)acetamide. |
| 111 | N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide. |

TABLE 2-continued

| # | Structure | Name |
|---|---|---|
| 112 | 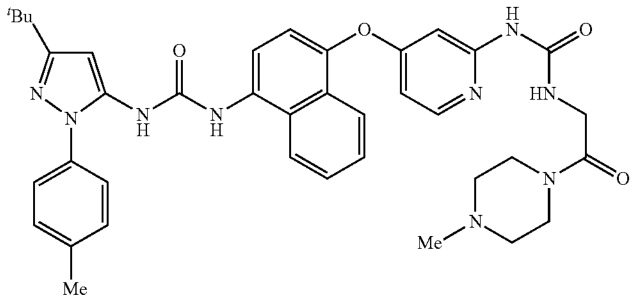 [SMILES: Cc1ccc(-n2nc(C(C)(C)C)cc2NC(=O)Nc2ccc(Oc3ccnc(NC(=O)NCC(=O)N4CCN(C)CC4)c3)c3ccccc23)cc1] | 1-(2-(3-(4-(4-(3-(3-tert-Butyl-1-p-tolyl-1H-pyrazol-5-yl)ureido)naphthalen-1-yloxy)pyridin-2-yl)ureido)acetyl)-4-methyl piperazine. |
| 113 | 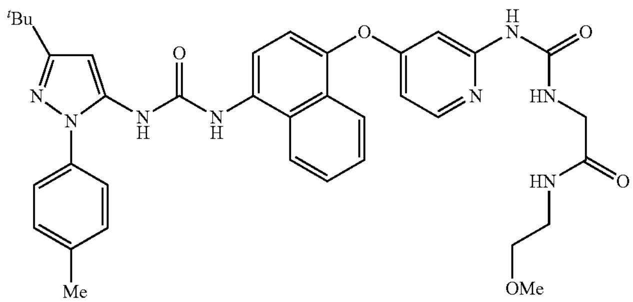 [SMILES: COCCNC(=O)CNC(=O)Nc1cc(Oc2ccc(NC(=O)Nc3cc(C(C)(C)C)nn3-c3ccc(C)cc3)c3ccccc23)ccn1] | N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide. |
| 114 | 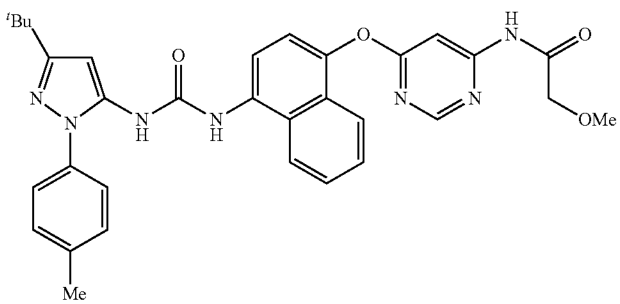 [SMILES: COCC(=O)Nc1cc(Oc2ccc(NC(=O)Nc3cc(C(C)(C)C)nn3-c3ccc(C)cc3)c3ccccc23)ncn1] | N-(6-(4-(3-(3-tert-Butyl-1-p-tolyl-1H-pyrazol-5-yl)ureido)naphthalen-1-yloxy)pyrimidin-4-yl)-2-methoxyacetamide. |
| 115 | 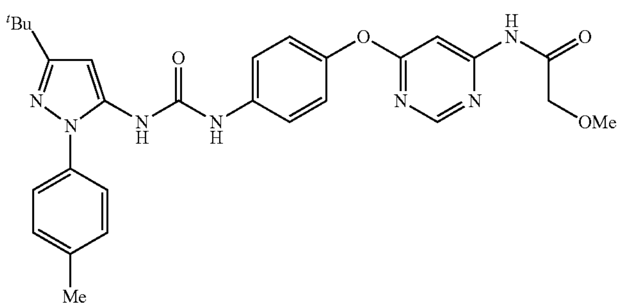 [SMILES: COCC(=O)Nc1cc(Oc2ccc(NC(=O)Nc3cc(C(C)(C)C)nn3-c3ccc(C)cc3)cc2)ncn1] | N-(6-(4-(3-(3-tert-Butyl-1-p-tolyl-1H-pyrazol-5-yl)ureido)phenoxy)pyrimidin-4-yl)-2-methoxyacetamide. |
| 116 | 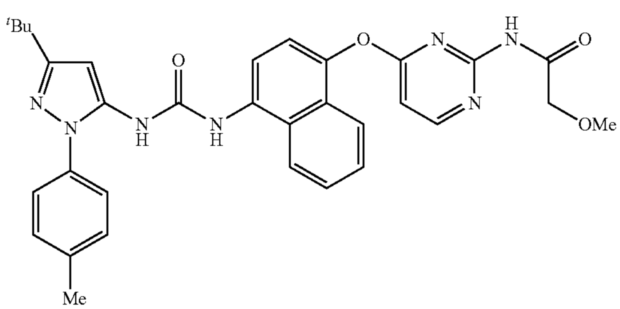 [SMILES: COCC(=O)Nc1nccc(Oc2ccc(NC(=O)Nc3cc(C(C)(C)C)nn3-c3ccc(C)cc3)c3ccccc23)n1] | N-(4-(4-(3-(3-tert-Butyl-1-p-tolyl-1H-pyrazol-5-yl)ureido)naphthalen-1-yloxy)pyrimidin-2-yl)-2-methoxyacetamide. |

TABLE 2-continued

| # | Structure | Name |
|---|---|---|
| 117 | 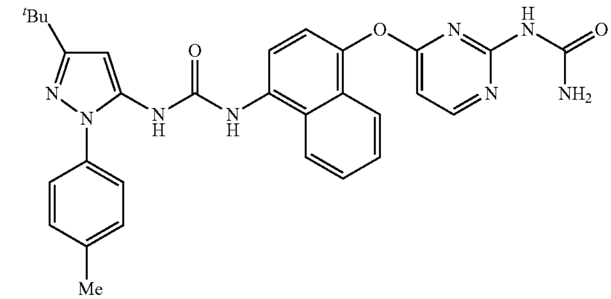 [SMILES: Cc1ccc(-n2nc(C(C)(C)C)cc2NC(=O)Nc2ccc(Oc3ccnc(NC(N)=O)n3)c3ccccc23)cc1] | 3-(4-(4-(3-(3-tert-Butyl-1-p-tolyl-1H-pyrazol-5-yl)ureido)naphthalen1-yloxy)pyrimidin-2-yl)urea. |
| 118 | 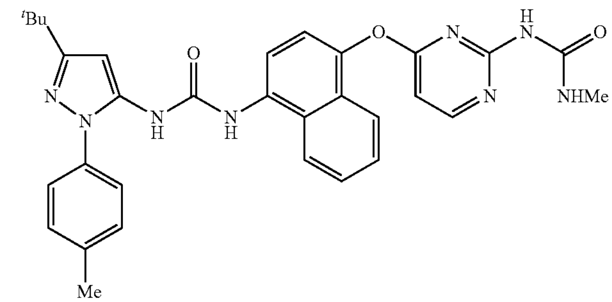 [SMILES: CNC(=O)Nc1nccc(Oc2ccc(NC(=O)Nc3cc(C(C)(C)C)nn3-c3ccc(C)cc3)c3ccccc23)n1] | 1-Methyl-3-(4-(4-(3-(3-tert-butyl-1-p-tolyl-1H-pyrazol-5-yl)ureido)naphthalen-1-yloxy)pyrimidin-2-yl)urea. |
| 119 | 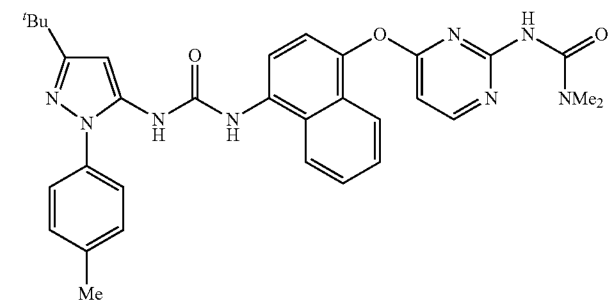 [SMILES: Cc1ccc(-n2nc(C(C)(C)C)cc2NC(=O)Nc2ccc(Oc3ccnc(NC(=O)N(C)C)n3)c3ccccc23)cc1] | 1,1-Dimethyl-3-(4-(4-(3-(3-tert-butyl-1-p-tolyl-1H-pyrazol-5-yl)ureido)naphthalen-1-yloxy)pyrimidin-2-yl)urea. |
| 120 | 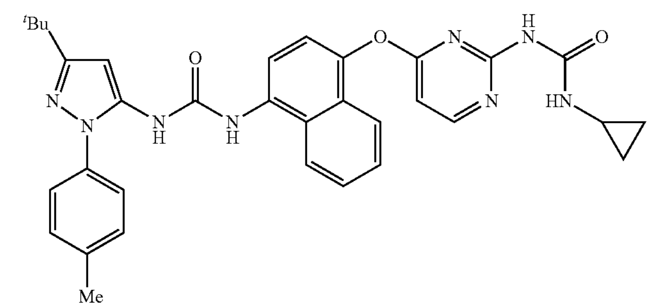 [SMILES: Cc1ccc(-n2nc(C(C)(C)C)cc2NC(=O)Nc2ccc(Oc3ccnc(NC(=O)NC4CC4)n3)c3ccccc23)cc1] | Cyclopropyl-3-(4-(4-(3-(3-tert-butyl-1-p-tolyl-1H-pyrazol-5-yl)ureido)naphthalen-1-yloxy)pyrimidin-2-yl)urea. |
| 121 | 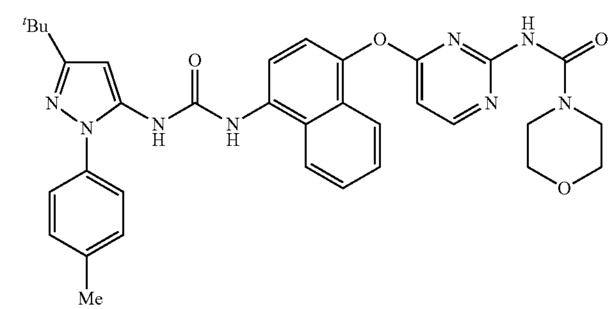 [SMILES: Cc1ccc(-n2nc(C(C)(C)C)cc2NC(=O)Nc2ccc(Oc3ccnc(NC(=O)N4CCOCC4)n3)c3ccccc23)cc1] | (4-(4-(3-(3-tert-Butyl-1-p-tolyl-1H-pyrazol-5-yl)ureido)naphthalen-1-yloxy)pyrimidin-2-yl)morpholine-4-carboxamide. |

TABLE 2-continued

| 122 | [structure of compound: tBu-pyrazole-tolyl with ureido-naphthalenyloxy-pyrimidinyl-urea] | 3-(6-(4-(3-(3-tert-Butyl-1-p-tolyl-1H-pyrazol-5-yl)ureido)naphthalen-1-yloxy)pyrimidin-4-yl)urea. |
|---|---|---|

Biological Testing

In Vitro RSV Virus Load in Primary Bronchial Epithelial Cells

Normal human bronchial epithelial cells (NHBEC) grown in 96 well plates, were infected at a multiplicity of infection (MOI) of 0.001 with RSV A2 (Strain A2, HPA, Salisbury, UK;) in LHC8 Media: RPMI-1640 (50:50) containing 15 mM magnesium chloride, and incubated for 1 hr at 37° C. to promote adsorption. The cells were then washed with PBS to remove non-infected virus particle and incubated for 4 days in fresh media. As appropriate, cells were pre-incubated with the test compound or DMSO for 2 hr, and then added again after wash with PBS as shown above.

The cells were fixed with 4% formaldehyde in PBS solution for 20 min, washed with washing buffer: PBS including 0.5% BSA and 0.05% Tween-20) (WB) and incubated with blocking solution (5% condensed milk in PBS) for 1 hr. Cells were then washed with WB and incubated for 1 hr at RT with anti-RSV (2F7) F-fusion protein antibody (mouse monoclonal) (lot 798760, Cat. No. ab43812, Abcam). After washing, cells were incubated with an HRP-conjugated secondary antibody (lot 00053170, Cat. No. P0447, Dako) and then TMB substrate (substrate reagent pack (lot 269472, Cat. No. DY999, R&D Systems, Inc.) was added.

The reaction was stopped by the addition of $2NH_2SO_4$ (50 µL) and the resultant signal was determined colorimetrically (OD: 450 nm with a reference wavelength of 655 nm) in a microplate reader (Varioskan® Flash, ThermoFisher Scientific). Cells were then washed and a 2.5% crystal violet solution (lot 8656, Cat. No. PL7000, Pro-Lab Diagnostics) was applied for 30 mins. After washing with WB, 100 µL of 1% SDS was added to each well, and plates were shaken lightly on the shaker for 1 hr prior to reading the absorbance at 595 nm. The measured OD450-655 readings were corrected to the cell number by dividing the OD450-655 by the OD595 readings. The percentage inhibition for each well was calculated and the $IC_{50}$ value was calculated from the concentration-response curve generated by the serial dilutions of compound. The compounds listed in Table 3 showed marked inhibition on RSV F-protein expression.

TABLE 3

Effects of treatment with selected compounds on RSV F-protein expression four days after infection with RSV, 0.001MOI in NHBEC.

| Compound Example No. | % inhibition (at 0.04 µg/mL) | $IC_{50}$ (nM) |
|---|---|---|
| 1 | 46.8 | 40.8 |
| 59 | 67.5 | 22.0 |

TABLE 3-continued

Effects of treatment with selected compounds on RSV F-protein expression four days after infection with RSV, 0.001MOI in NHBEC.

| Compound Example No. | % inhibition (at 0.04 µg/mL) | $IC_{50}$ (nM) |
|---|---|---|
| 88 | 71.7 | |
| 65 | 56.5 | |
| 40 | 24.9 | 102.8 |

HBECs obtained from patients with cystic fibrosis (CF-BEC) and Hep2 cells (human larynx epidermoid carcinoma cell line) were also used. Although anti-virus agent, Ribavirin, worked better in Hep2, virus friendly cancer cells, but compound Example 1 and compound Example 59 showed better efficacy in NHBEC and CF-BEC than in Hep2 cells (Table 4).

TABLE 4

Comparative effects of treatment with selected compounds on RSV F-protein expression 4 days after infection with RSV, at 0.001MOI in Hep2 cells, NHBEC and CF-BEC.

| Test Compound Example No (Test Conc µg/mL) | n value | Cell Type | | | | | |
|---|---|---|---|---|---|---|---|
| | | Hep2 | | NHBEC | | CF-BEC | |
| | | $IC_{50}$ (nM) | E-max (%) | $IC_{50}$ (nM) | E-max (%) | $IC_{50}$ (nM) | E-max (%) |
| 1 (0.0016-0.2) | 4 | | 24 | 41 | 51 | 69 | 84 |
| 59 (0.0016-0.2) | 4 | 289 | 58 | 22 | 78 | 58 | 87 |
| Fluticasone propionate (0.04-0.2) | 3 | ND[b] | | | −38 | | 10 |
| Ribavirin (10) | 3 | 9[a] | 93 | | 78 | | 53 |

[a] µM;
[b] Not determined

RSV Titre Assay Using Air-Liquid Interface Cultured Bronchial Epithelial Cells

Primary nasal epithelial cells, cultured using an air-liquid interface, were purchased from Epithelix Sarl (Geneva, Switzerland). Fresh, warmed media (200 µL) containing either the test compound at the selected concentration or vehicle (DMSO; final concentration of 0.5%) was transferred to the apical chamber, and fresh, warmed media (700 µL) containing either the test compound at the selected concentration or vehicle (DMSO; final concentration of 0.5%) were transferred to the bottom chamber. After incubation for 2 hr, the media in upper well was removed carefully. The following day, fresh, warmed media (200 µL) containing either the test compound at the selected concentration or vehicle (DMSO; final concentration of 0.5%) was transferred to the apical chamber again, and after incubation for 2 hr, the media was removed. On the third day, cells were treated again for 2 hr, and the media was removed.

The cells in the apical well were infected with 50 µL of RSV Memphis 37 virus (Meridian) 2 (producing an MOI of approximately 0.1 at the estimated cell number of $1 \times 10^6$/well) and incubated for 1 hr. The apical media was then removed by aspiration and the wells were washed twice with warmed PBS. The plate was incubated at 37° C. At 1 hr, and at timepoints: 1, 2, 3, 5, 6, 7, 8, 9, 10 days after infection, of warmed (37° C.) PBS (300 µL) was added to the apical chamber and the preparation left for 10 min. The supernatant was collected from the apical chamber. An aliquot of the supernatant (150 µL) was retained and kept at –20° C. for IL-8 cytokine assay and a second aliquot (150 µL) of the supernatant was mixed with 50 uL of media containing 15% sucrose (final 3.75%) and then kept at –20° C. for a virus titre assay.

IL-8 concentrations were determined using a Duoset ELISA development kit (R&D Systems, Minneapolis, Minn.; FIG. 1)

The virus titre was estimated by CPE assay in Hep2 cells as follows: Supernatant (20 µL) was collected and 10-fold serial dilutions were prepared in 5%-FBS DMEM. All titrations were performed by infecting confluent Hep2 cell monolayers (in 96 well plates) with the serially diluted supernatant preparations ($10^{-1}$-$10^{-5}$). The resultant cytopathic effects (CPE) were assessed by visual inspection 3 days after infection. The amount of virus required to infect 50% of Hep2 cells was calculated for each treatment and is reported as log [$TCID_{50}$] (U/20 µL) (FIG. 2).

Figure 2:
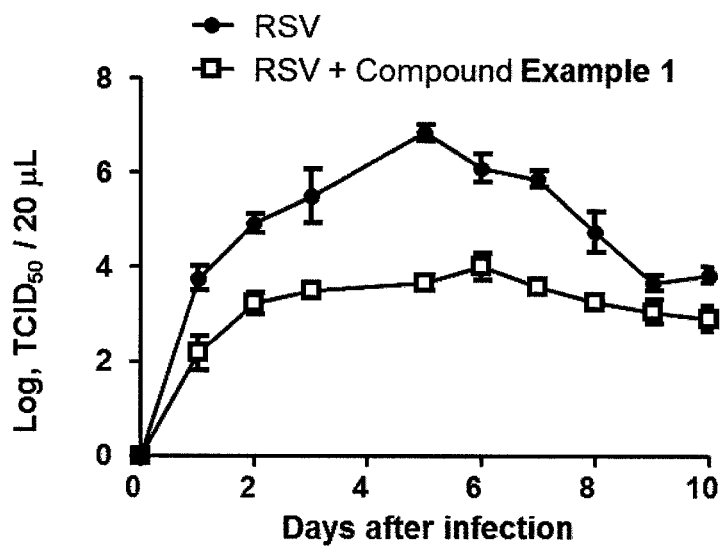
FIG. 2 shows the effects of compound Example 1 on RSV Memphis 37 viral load in primary 3D cultured nasal epithelial cells.

As shown in FIGS. 1 and 2, compound Example 1 showed strong inhibition on RSV-induced IL-8 production and RSV viral load.

RSV Virus Load in Mouse Lung

Wild type, specific pathogen-free male Balb/c mice aged 8 weeks and weighing approximately 25 g were obtained from the Animal Resource Centre Pty. Ltd., Australia. On day zero, appropriate animal groups were anaesthetised with the inhalation anaesthetic methoxyfluorane and nasally inoculated with either virus diluent (low protein serum free VPSSM from Invitrogen) or $10^6$ $TCID_{50}$ units of human RSV A2 in a volume of 50 µL. The compounds of Example 1 and Example 59 were dosed intra-tracheally (20 µL of a 0.1 mg/mL solution) on day 1 and for 7 subsequent days. Eleven to thirteen animals from each group were sacrificed on days 3, 5, 7 and 9 to enable lung viral load to be determined using a plaque assay (Table 5). In vehicle-dosed animals, virus titre peaked at Day 5 post-infection, and treatment with either compound Example 1 or compound Example 59 inhibited viral load by 67% and 90%, respectively. Treatment with either compound Example 1 or compound Example 59 did not augment viral load at Day 9 when virus had been eliminated in vehicle-treated mice.

TABLE 5

Effects of treatment with Example 1 and 59 on pulmonary virus load following inoculation with RSV.

| Treatment following RSV inoculation | Treatment time post RSV infection (days) | | | |
|---|---|---|---|---|
| | 3 | 5 | 7 | 9 |
| | Lung virus load ($TCID_{50}$/g lung tissue $\times 10^3$) | | | |
| Vehicle | 395 ± 244 | 4,695 ± 4,363 | 3.2 ± 1.2 | 0.5 ± 0.3 |
| Example 1 | 66 ± 18 | 1,545 ± 918 | 7.1 ± 5.2 | ND |
| Example 59 | 81 ±29 | 448 ± 268 | 2.4 ± 0.8 | 0.3 ± 0.1 |

Results are presented as the mean ± SEM (n = 11-13), ND not determined

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A method of treatment or prophylaxis of respiratory syncytial virus (RSV) infection and/or the exacerbation of respiratory disorders by RSV infection which comprises administering to a subject in need thereof an effective amount of a compound of formula

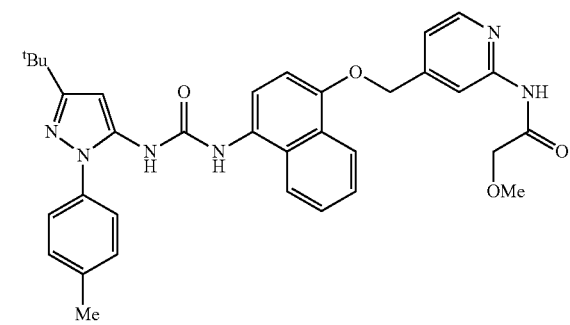

a pharmaceutically acceptable salt thereof, including all stereoisomers, tautomers and isotopic derivatives thereof.

* * * * *